US011155606B2

(12) United States Patent
Tkaczyk et al.

(10) Patent No.: US 11,155,606 B2
(45) Date of Patent: Oct. 26, 2021

(54) **ANTIBODY DIRECTED AGAINST *S. AUREUS* CLUMPING FACTOR A (CLFA)**

(71) Applicants: MedImmune, LLC, Gaithersburg, MD (US); Humabs BioMed SA, Bellinzona (CH)

(72) Inventors: Christine Tkaczyk, Gaithersburg, MD (US); Bret Sellman, Gaithersburg, MD (US); Martin Borrok, III, Gaithersburg, MD (US); Davide Corti, Bellinzona (CH); Andrea Minola, Bellinzona (CH)

(73) Assignees: MedImmune, LLC, Gaithersburg, MD (US); Humabs BioMed SA, Bellinzona (CH)

( * ) Notice: Subject to any disclaimer, the term of this patent is extended or adjusted under 35 U.S.C. 154(b) by 0 days.

(21) Appl. No.: 16/521,223

(22) Filed: Jul. 24, 2019

(65) Prior Publication Data

US 2020/0048330 A1 Feb. 13, 2020

Related U.S. Application Data

(60) Provisional application No. 62/702,762, filed on Jul. 24, 2018.

(51) Int. Cl.
*C07K 16/12* (2006.01)

(52) U.S. Cl.
CPC ...... *C07K 16/1271* (2013.01); *C07K 2317/31* (2013.01); *C07K 2317/34* (2013.01); *C07K 2317/51* (2013.01); *C07K 2317/515* (2013.01)

(58) Field of Classification Search
None
See application file for complete search history.

(56) References Cited

U.S. PATENT DOCUMENTS

| | | | |
|---|---|---|---|
| 7,364,738 | B2 | 4/2008 | Patti |
| 9,527,905 | B2 | 12/2016 | Sellman et al. |
| 9,845,348 | B2 | 12/2017 | Sellman et al. |
| 9,879,070 | B2 | 1/2018 | Sellman et al. |
| 10,457,724 | B2 | 10/2019 | Sellman et al. |
| 2017/0129943 | A1 | 5/2017 | Sellman et al. |
| 2019/0016787 | A1 | 1/2019 | Sellman et al. |
| 2019/0077851 | A1 | 3/2019 | Jafri et al. |
| 2020/0109189 | A1 | 4/2020 | Tkaczyk et al. |

FOREIGN PATENT DOCUMENTS

| | | |
|---|---|---|
| WO | WO 02/072600 A2 | 9/2002 |
| WO | WO 2012/109285 A2 | 8/2012 |
| WO | WO 2014/074540 A2 | 5/2014 |
| WO | WO 2015/175874 A2 | 11/2015 |
| WO | WO-2016166223 A1 | 10/2016 |
| WO | WO-2017075188 A2 | 5/2017 |
| WO | WO-2020076789 A2 | 4/2020 |

OTHER PUBLICATIONS

Skolnick et al. (Trends in Biotechnology 18: 34-39, 2000).*
Greenspan et al. (Nature Biotechnology 7: 936-937, 1999).*
Giusti et al. (Proc. Natl. Acad. Sci. USA. May 1987 84 (9): 2926-2930).*
Winkler et al (J. Imm., 265:4505-4514, 2000).*
Chien et al. (Proc. Natl. Acad. Sci. USA. Jul. 1989 86 (14): 5532-5536).*
Caldas et al. (Mol. Immunol. May 2003 39 (15): 941-952).*
Casadevall et al. (PNAS vol. 109 No. 31, p. 12272-12273).*
Borrok et al., "pH-dependent Binding Engineering Reveals an FcRn Affinity Threshold That Governs IgG Recycling," J. Biol. Chem. 290(7): 4282-4290, The American Society for Biochemistry and Molecular Biology, United States (2015).
Coloma, M.J. and Morrison, S.L., "Design and production of novel tetravalent bispecific antibodies," Nat. Biotechnol., 15: 159-163, The Nature Publishing Group, England (1997).
Digiandomenico, A., and Sellman, B.R., "Antibacterial monoclonal antibodies: the next generation?" Curr. Opin. Microbiol., 27: 78-85, Elsevier, Netherlands (2015).
Dimasi et al., "The Design and Characterization of Oligospecific Antibodies for Simultaneous Targeting of Multiple Disease Mediators," J. Mol. Biol., 393: 672-692 (2009).
Foletti et al., "Mechanism of Action and In Vivo Efficacy of a Human-Derived Antibody against *Staphylococcus aureus* α-Hemolysin," J. Mol. Biol., 425(10): 1641-1654 (2013).
Hazenbos et al., "Novel Staphylococcal Glycosyltransferases SdgA and SdgB Mediate Immunogenicity and Protection of Virulence-Associated Cell Wall Proteins," PLoS Pathog., 9(10):e1003653, 18 pages, Public Library of Science, United States (2013).
Hua et al., "Assessment of an anti-alpha-toxin monoclonal antibody for prevention and treatment of *Staphylococcus aureus*-induced pneumonia," Antimicrob. Agents. Chemother., 58(2): 1108-1117, American Society for Microbiology, United States (2014).
Karauzum et al., "Synthetic Human Monoclonal Antibodies toward Staphylococcal Enterotoxin B (SEB) Protective against Toxic Shock Syndrome," J Biol Chem., 287(30): 25203-15, American Society for Biochemistry and Molecular Biology, United States (2012).
Lowy, F.D., "*Staphylococcus aureus* Infections," N. Engl. J. Med., 339(8): 520-32, Massachusetts Medical Society, United States (1998).
Mendes et al., "Characterization of Methicillin-Resistant *Staphylococcus aureus* Strains Recovered from a Phase IV Clinical Trial for Linezolid versus Vancomycin for Treatment of Nosocomial Pneumonia," J. Clin. Microbiol., 50: 3694-3702, American Society for Microbiology, United States (2012).

(Continued)

*Primary Examiner* — Robert A Zeman
(74) *Attorney, Agent, or Firm* — Sterne, Kessler, Goldstein & Fox P.L.L.C.

(57) ABSTRACT

The present disclosure is directed to a monoclonal antibody, or antigen-binding fragment thereof, that specifically binds to a *Staphylococcus aureus* clumping factor A protein (ClfA), as well as compositions comprising the monoclonal antibody. The disclosure also is directed to methods of treating a *Staphylococcus aureus* infection by administering the anti-ClfA monoclonal antibody alone, or in combination with a monoclonal antibody that specifically binds to *S. aureus* alpha toxin (AT) protein to a subject. Bispecific monoclonal antibodies that specifically bind to both ClfA and AT and methods of using the same also are provided.

18 Claims, 21 Drawing Sheets

Specification includes a Sequence Listing.

(56) References Cited

OTHER PUBLICATIONS

Monnet C., et al., "Selection of IgG variants with increased FcRn binding using random and directed mutagenesis: impact on effector functions," Frontiers Immunol. 6: 39, pp. 1-14, Frontiers Media S.A., Switzerland (2015).

Ragle, B.E., and Wardenburg, J. B., "Anti-Alpha-Hemolysin Monoclonal Antibodies Mediate Protection against *Staphylococcus aureus* Pneumonia," Infect. Immun 77: 2712-2718, American Society for Microbiology (2009).

Rouha, H., "Five birds, one stone: neutralization of α-hemolysin and 4 bi-component leukocidins of *Staphylococcus aureus* with a single human monoclonal antibody," MAbs, 7(1): 243-254 (2015).

Sharma-Kuinkel et al., "Characterization of Alpha-Toxin hla Gene Variants, Alpha-Toxin Expression Levels, and Levels of Antibody to Alpha-Toxin in Hemodialysis and Postsurgical Patients with *Staphylococcus aureus* Bacteremia," J. Clin. Microbiol., 53: 227-236, American Society for Microbiology, United States (2015).

Tkaczyk et al., "Identification of Anti-Alpha Toxin Monoclonal Antibodies That Reduce the Severity of *Staphylococcus aureus* Dermonecrosis and Exhibit a Correlation between Affinity and Potency," Clin. Vaccine Immunol., 19: 377-385, American Society for Microbiology, United States (2012).

Tkaczyk et al., "Targeting Alpha Toxin and ClfA with a Multimechanistic Monoclonal Antibody-Based Approach for Prophylaxis of Serious *Staphylococcus aureus* Disease," mBio., 7(3): e00528-16, 11 pages, American Society for Microbiology, United States (2016).

Traggiai et al., "An efficient method to make human monoclonal antibodies from memory B cells: potent neutralization of SARS coronavirus," Nat. Med., 10: 871-875, Nature Publishing Group, England (2004).

Wardenburg, J.B. and Schneewind, O., "Vaccine protection against *Staphylococcus aureus* pneumonia," J. Exp. Med., 205: 287-294, Rockefeller University Press, United States (2008).

Tkaczyk et al., "Multimechanistic Monoclonal Antibodies (MAbs) Targeting *Staphylococcus aureus* Alpha-Toxin and Clumping Factor A: Activity and Efficacy Comparisons of a MAb Combination and an Engineered Bispecific Antibody Approach," Antimicrobial Agents and Chemotherapy 61(8): e00629-17, 14 pages, American Society for Microbiology, United States (2017).

Ortines, R. et al., "Neutralizing Alpha-Toxin Accelerates Healing of *Staphylococcus aureus*-Infected Wounds in Nondiabetic and Diabetic Mice," Antimicrobial Agents and Chemotherapy 62(3): e02288-17, 14 pages, American Society for Microbiology, United States (2018).

Co-Pending Application, U.S. Appl. No. 16/596,388, inventors Tkaczyk; C. et al., filed Oct. 8, 2019 (Not Published).

Co-Pending Application, U.S. Appl. No. 16/596,445, inventors Tkaczyk; C. et al., filed Oct. 8, 2019 (Not Published).

Co-Pending Application, U.S. Appl. No. 16/599,595, inventors Sellman; B., et al., filed Oct. 11, 2019 (Not Published).

Yeung, Y.A. et al., "Engineering Human IgG1 Affinity to Human Neonatal Fc Receptor: Impact of Affinity Improvement on Pharmacokinetics in Primates," J. Immunology, 182:12 7663-7671 (2009).

NPL25 International Search Report and Written Opinion dated Feb. 13, 2020, in PCT/US2019/043254, European Patent Office, Netherlands, 21 pages.

Gershoni, J., et al., Epitope mapping—the first step in developing epitope based vaccines, BioDrugs 21(3):145-156, Adis Data Information, United States (2007).

Hall, A.E., et al., "Characterization of a Protective Monoclonal Antibody Recognizing *Staphylococcus aureus* MSCRAMM Protein Clumping Factor A," Infection and Immunity 71(12):6864-6870, American Society for Microbiology, United States (2003).

International Search Report and Written Opinion dated Sep. 23, 2020, in International Application No. PCT/US2019/055143, EPO, Netherlands, 22 pages.

Ortines, R.V., et al., "Efficacy of a Multimechanistic Monoclonal Antibody Combination against *Staphylococcus aureus* Surgical Site Infections in Mice," Antimicrobial Agents and Chemotherapy 63(8):e00346-19, 6 pages, American Society for Microbiology, United States (Aug. 2019).

Yu, X.-Q., et al., " Safety, Tolerability, and Pharmacokinetics of MEDI4893, an Investigational, Extended-Half-Life, Anti-*Staphylococcus aureus* Alpha-Toxin Human Monoclonal Antibody, in Healthy Adults," Antimicrobial Agents and Chemotherapy 61(1):e01020-16, 9 pages, American Society for Microbiology, United States (Jan. 2017).

Vernachio, J., et al., "Anti-Clumping Factor A Immunoglobulin Reduces the Duration of Methicillin-Resistant *Staphylococcus aureus* Bacteremia in an Experimental Model of Infective Endocarditis," Antimicrobial Agents and Chemotherapy 47(11):3400-3406, American Society for Microbiology, United States (2003).

Yanjie, M., et al., "713. Preventive Administration of MEDI6389, a Combination of Monoclonal Antibodies (mAbs) Targeting Alpha-Toxin (AT), Panton-Valentine Leukocidin (PVL), Leukocidin ED (LukED), Gamma-Hemolysin and Clumping Factor A (ClfA), in a Rabbit Model of USA300 MRSA Prosthetic Joint Infection (PJI)," Open Forum Infect Dis 6(S2):S320-S321, Oxford Academic, England (Oct. 2019).

Office Action dated Oct. 2, 2020 in U.S. Appl. No. 16/596,388, inventors Tkaczyk, C., et al., filed Oct. 8, 2019, 17 pages.

* cited by examiner

Figure 1
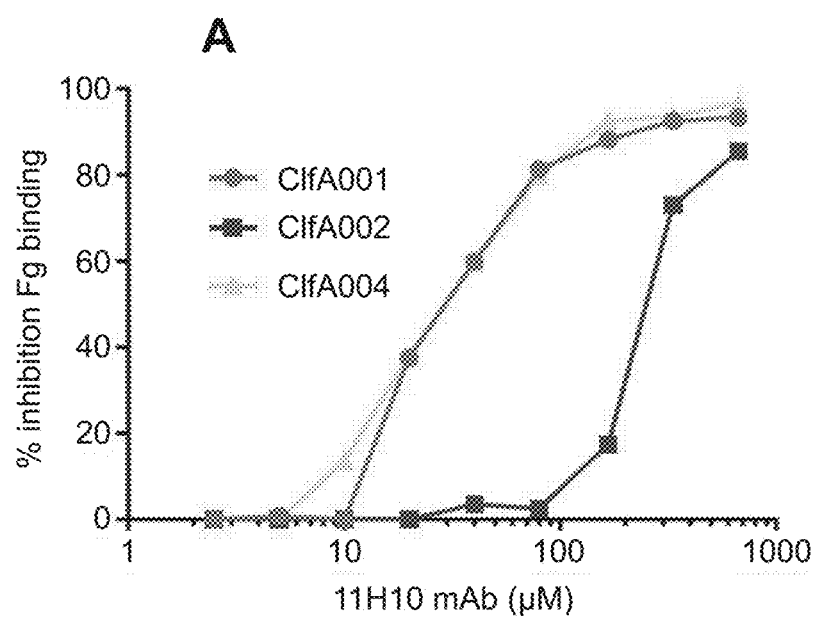
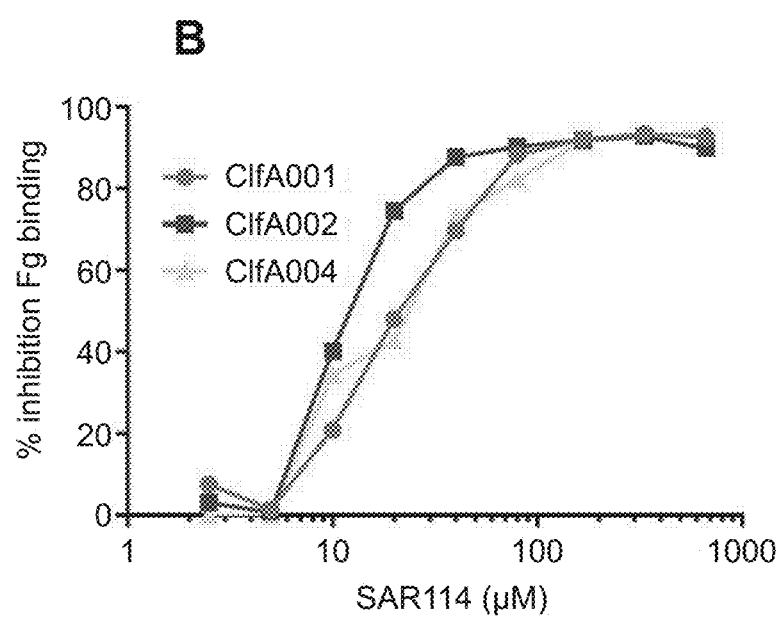

Figure 6
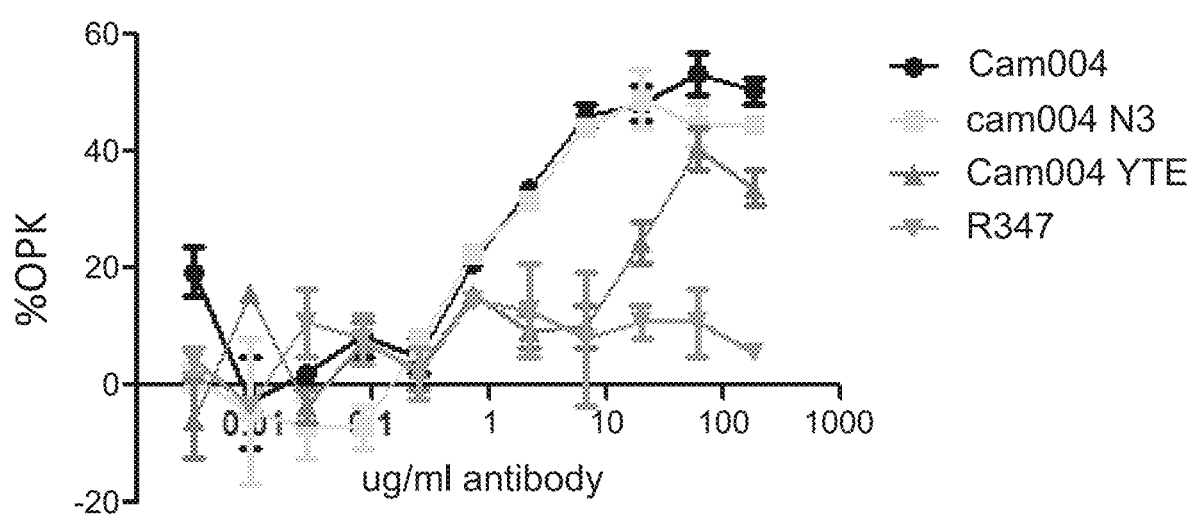
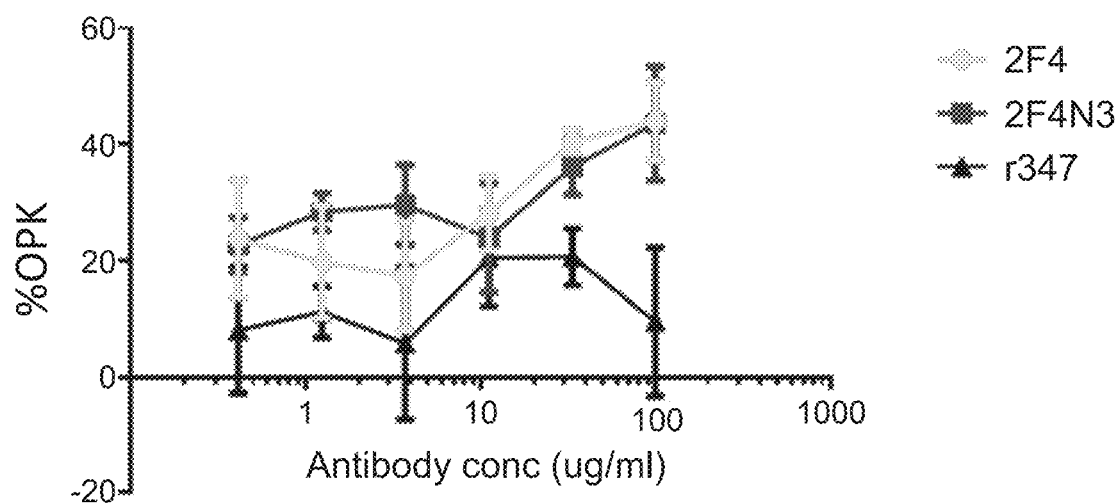

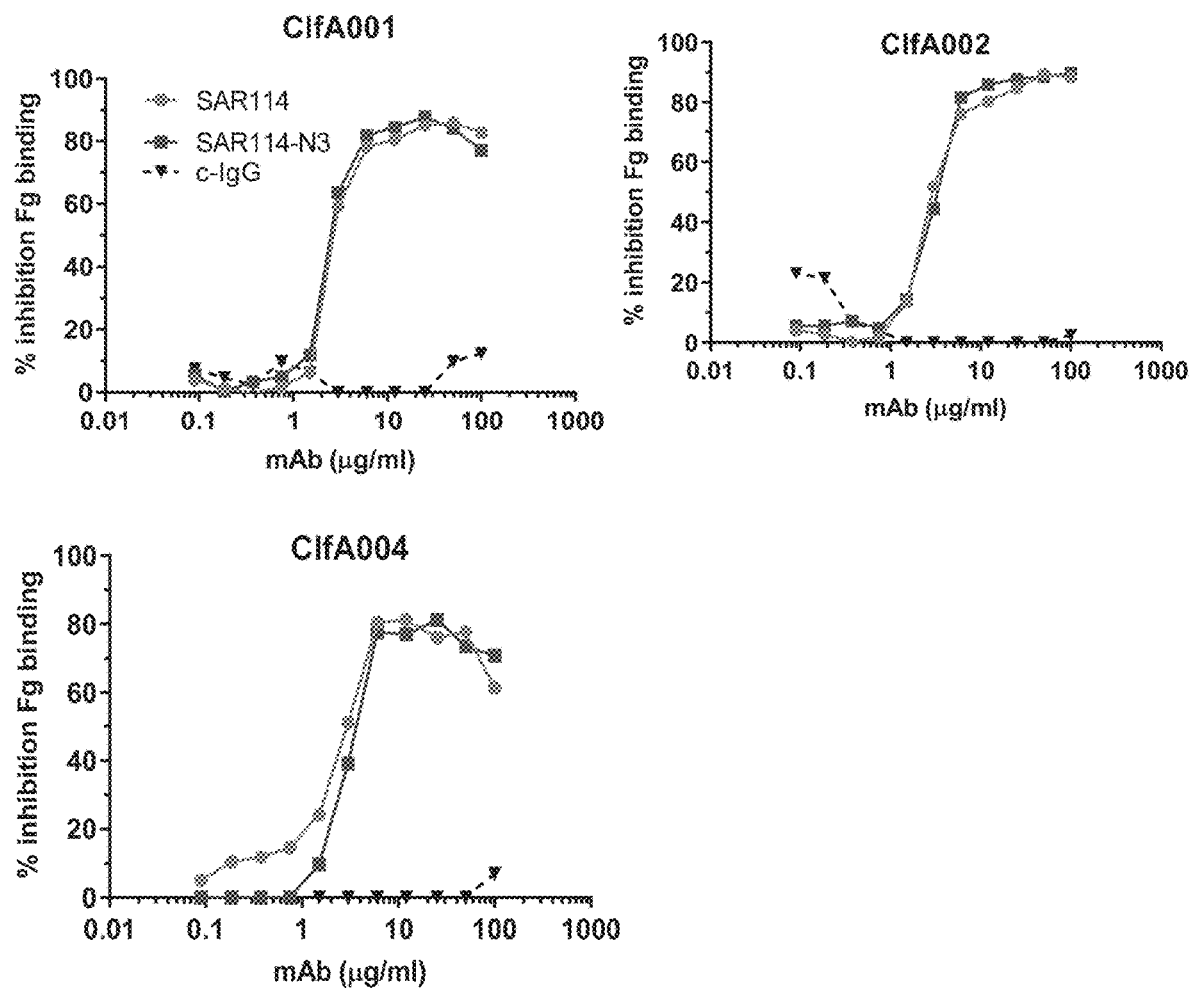

Figure 9
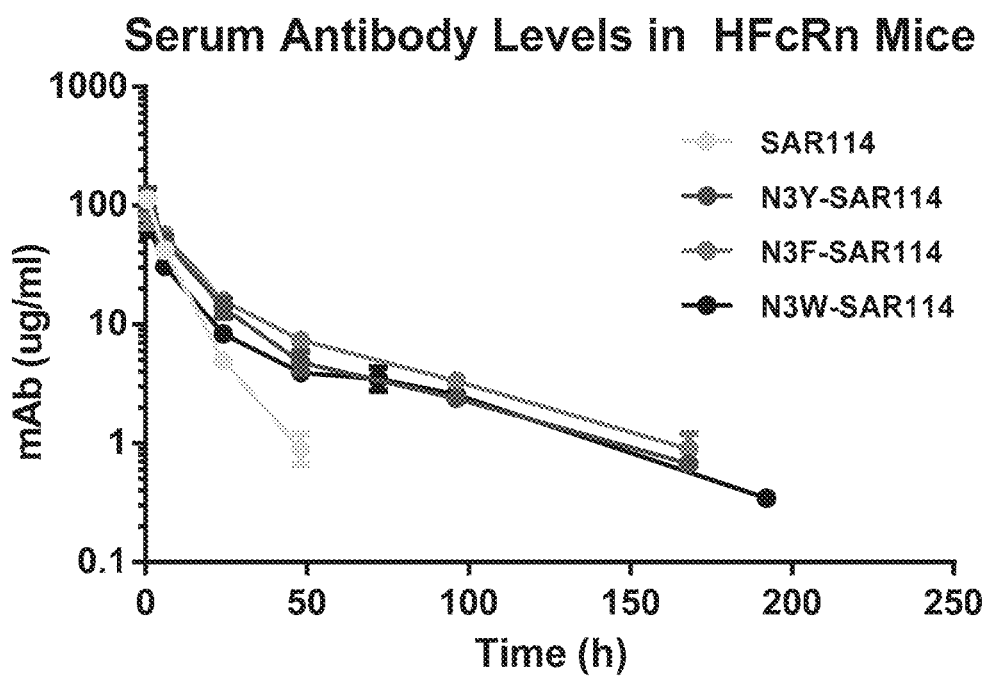
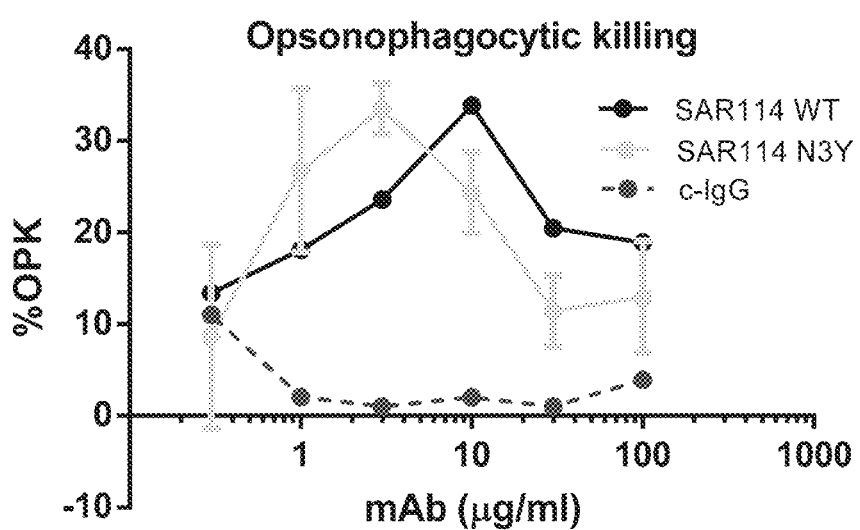

Figure 14
A
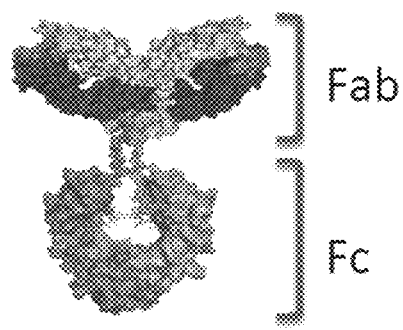
IgG1 : α-ClfA
B
scFv: α-AT    scFv: α-AT
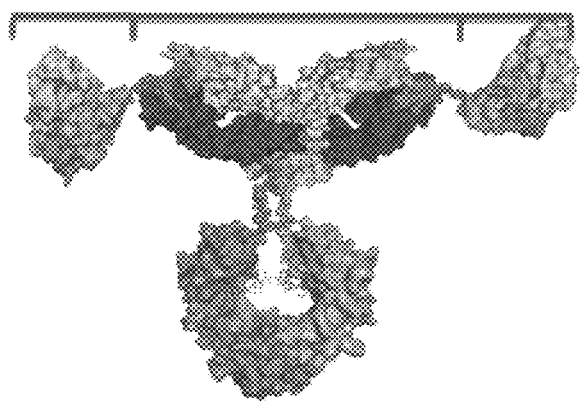
BiS$_2$
C
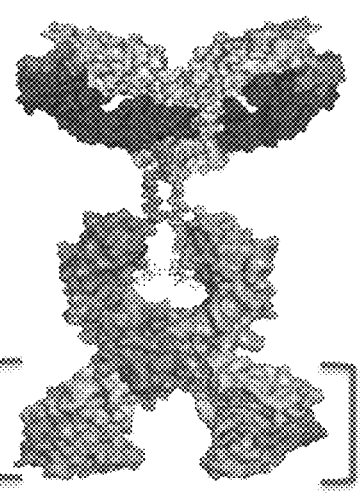
scFv: α-AT
BiS$_3$ Figure 17
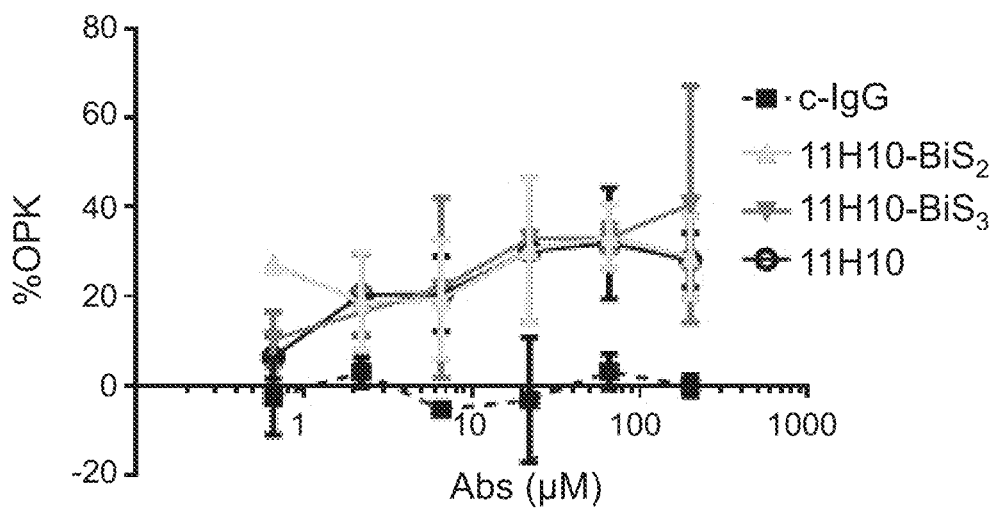
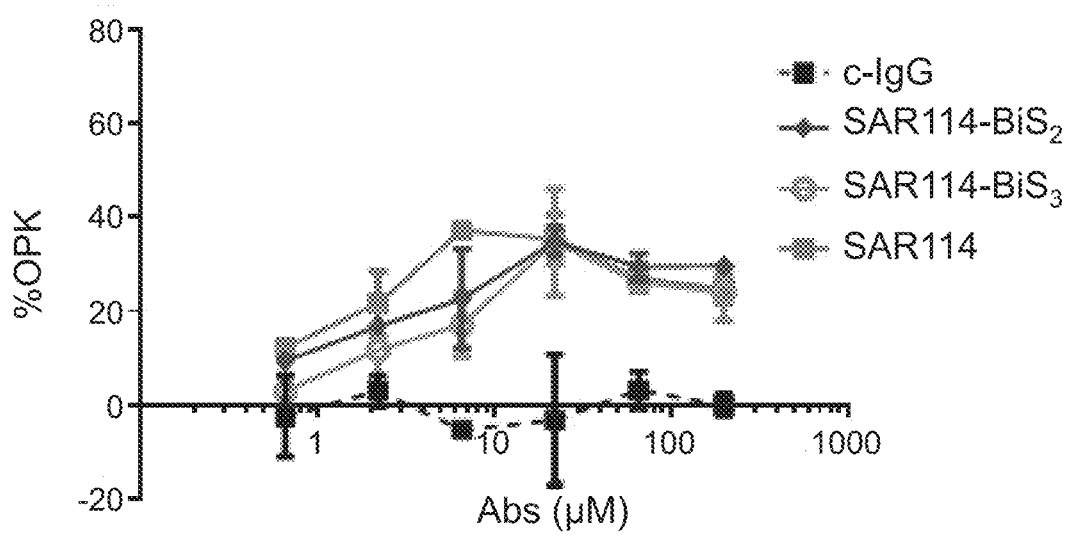

Figure 19
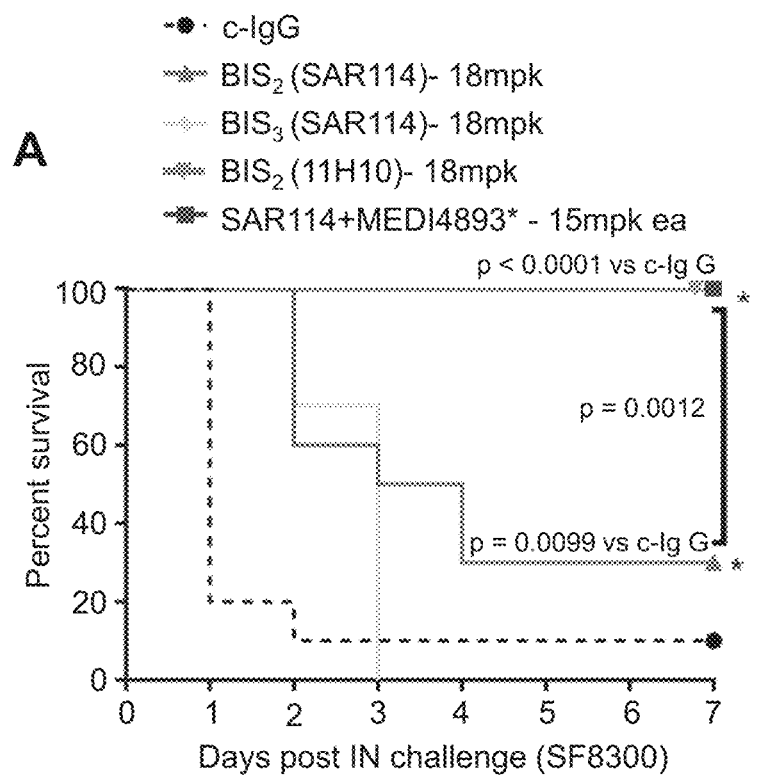
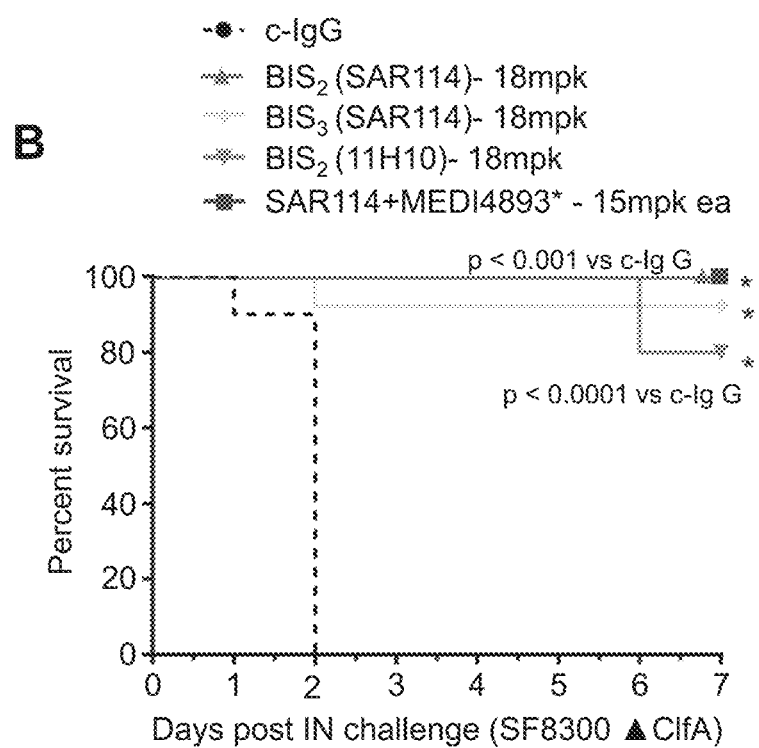

ANTIBODY DIRECTED AGAINST S. AUREUS CLUMPING FACTOR A (CLFA)

CROSS REFERENCE TO RELATED APPLICATIONS

This application claims the priority benefit of U.S. Provisional Application No. 62/702,762, filed Jul. 24, 2018, which is hereby incorporated by reference herein in its entirety.

SEQUENCE LISTING

The content of the electronically submitted sequence listing (Name: 2943_1000001_SeqListing_ST25.txt; Size: 60,649 bytes; and Date of Creation: Jul. 22, 2019) is hereby incorporated by reference.

BACKGROUND OF THE INVENTION

Infections caused by antimicrobial resistant (AMR) bacterial pathogens are an increasing threat to public health. The ongoing AMR epidemic has been fueled, in part, by empiric broad spectrum antibiotic therapy. This has led to the exploration of pathogen specific methods, including monoclonal antibodies (mAbs), to prevent or treat serious bacterial infections. Numerous monoclonal antibodies are currently in development for the prevention or treatment of antibiotic resistant bacterial infections (see, e.g., DiGiandomenico, A., and B. R. Sellman, Curr. Opin. Microbiol., 27: 78-85 (2015)). Such passive immunization strategies provide an immediate and potent immunoglobulin response against the target pathogen. Ideally, the monoclonal antibody or monoclonal antibody cocktail provides multiple mechanisms of action to neutralize key bacterial virulence mechanisms and augment the host innate immune response, thus providing the greatest opportunity for clinical success.

Staphylococcus aureus is a bacterial pathogen that causes a wide array of diseases including skin and soft tissue infections, endocarditis, osteomyelitis, pneumonia, and bacteremia (Lowy, F. D., N. Engl. J. Med., 339(8): 520-32 (1998)). Preclinical studies indicate monoclonal antibody-based approaches hold promise for prophylaxis and adjunctive therapy against S. aureus infections (see, e.g., Hazenbos et al., PLoS Pathog., 9(10):e1003653. doi: 10.1371/journal.ppat.10036532013 (2013); Rouha, H., MAbs, 7(1): 243-254 (2015); Foletti et al., J. Mol. Biol., 425(10): 1641-1654 (2013); Karauzum et al., J Biol Chem., 287(30): 25203-15 (2012); and Hua et al., Antimicrob Agents Chemother., 58(2): 1108-17 (2014)). A multi-mechanistic monoclonal antibody combination targeting S. aureus alpha toxin (AT) and clumping factor A (ClfA) was shown to enhance protection and improve strain coverage relative to each individual monoclonal antibody in a S. aureus lethal bacteremia model (Tkaczyk et al., MBio., 7(3). pii: e00528-16 (2016)); however, the tested ClfA monoclonal antibody exhibits reduced binding affinity and functional activity against the ClfA founder sequence ClfA002 relative to two other founder sequences (ClfA001 and ClfA004).

Thus, there remains a need for compositions and methods for treating Staphylococcus aureus infections, particularly infections that are resistant to currently-available antibiotics. The present disclosure provides such compositions and methods.

BRIEF SUMMARY OF THE INVENTION

Provided herein are antibodies or antigen-binding fragments that bind to Staphylococcus aureus (S. aureus) clumping factor A (ClfA) protein. In certain instances, an antibody or antigen-binding fragment thereof that specifically binds to a S. aureus ClfA protein, comprises a variable heavy chain (VH) complementarity determining region (CDR) 1 comprising the amino acid sequence of SEQ ID NO: 1, a VH CDR2 comprising the amino acid sequence of SEQ ID NO: 2, a VH CDR3 comprising the amino acid sequence of SEQ ID NO: 3, a variable light chain (VL) CDR1 comprising the amino acid sequence of SEQ ID NO: 4, a VL CDR2 comprising the amino acid sequence of SEQ ID NO: 5, and a VL CDR3 comprising the amino acid sequence of SEQ ID NO: 6, and the antibody or antigen-binding fragment comprises a heavy chain constant domain comprising the amino acid sequence of CSYHLC (SEQ ID NO: 21). In certain instances, the antibody or antigen-binding fragment thereof comprises a VH comprising the amino acid sequence of SEQ ID NO: 13. In certain instances, the antibody or antigen-binding fragment thereof comprises a VL comprising the amino acid sequence of SEQ ID NO: 14.

In certain instances, an antibody or antigen-binding fragment thereof that specifically binds to a S. aureus ClfA protein comprises a VH, a VL, and a heavy chain constant domain comprising the amino acid sequence of CSYHLC (SEQ ID NO: 21), wherein the VH comprises the amino acid sequence of SEQ ID NO: 13.

In certain instances, an antibody or antigen-binding fragment thereof that specifically binds to a S. aureus ClfA protein comprises a VH, a VL, and a heavy chain constant domain comprising the amino acid sequence of CSYHLC (SEQ ID NO: 21), wherein the VL comprises the amino acid sequence of SEQ ID NO: 14.

In certain instances, an antibody or antigen-binding fragment thereof that specifically binds to a S. aureus ClfA protein comprises the VH CDR1, VH CDR2, VH CDR3, VL CDR1, VL CDR2, and VL CDR3 of SAR114. In certain instances, the CDRs are the Kabat-defined CDRs, the Chothia-defined CDRs, or the AbM-defined CDRs. In certain instances, the antibody or antigen-binding fragment comprises a heavy chain constant domain comprising the amino acid sequence of CSYHLC (SEQ ID NO: 21).

In certain instances, the heavy chain constant domain comprises the amino acid sequence of MHEACSYHLCQKSLSLS (SEQ ID NO: 23). In certain instances, the heavy chain constant domain comprises the amino acid sequence of SEQ ID NO: 24. In certain instances, the antibody or antigen-binding fragment thereof comprises a heavy chain comprising the amino acid sequence of SEQ ID NO: 50. In certain instances, the antibody or antigen-binding fragment thereof comprises a light chain comprising the amino acid sequence of SEQ ID NO: 26.

In certain instances, the IC50's of the antibody or antigen-binding fragment thereof for ClfA001, ClfA002, and ClfA004 in a fibrinogen binding inhibition assay are within 2 µg/ml of each other. In certain instances, the $IC_{50}$'s of the antibody or antigen-binding fragment thereof for ClfA001, ClfA002, and ClfA004 in a fibrinogen binding inhibition assay are all between 1 µg/ml and 5 µg/ml. In certain instances, the binding affinities ($K_D$) of the antibody or antigen-binding fragment thereof for ClfA001, ClfA002, and ClfA004 are all between 200 and 350 pM.

In certain instances, the antibody or antigen-binding fragment thereof has a monomer purity that decreases by no more than 5% after exposure of the antibody or antigen-binding fragment to conventional white light at 2 kLux/hr at 23° C. for 14 days. In certain instances, the antibody or antigen-binding fragment comprises a mutation that extends half-life relative to the same antibody without the mutation in human FcRn mice. In certain instances, the antibody or antigen-binding fragment comprises a mutation that extends half-life relative to the same antibody without the mutation, and wherein the mutation does not inhibit OPK activity relative to the same antibody or antigen-binding fragment the mutation.

Provided herein are also bispecific antibodies and antigen-binding fragments thereof that specifically bind to S. aureus ClfA protein and S. aureus alpha toxin (AT) protein. In certain instances, a bispecific antibody or antigen-binding fragment thereof that specifically binds to a S. aureus ClfA protein and a S. aureus alpha toxin (AT) protein comprises a VH CDR1 comprising the amino acid sequence of SEQ ID NO: 1, a VH CDR2 comprising the amino acid sequence of SEQ ID NO: 2, a VH CDR3 comprising the amino acid sequence of SEQ ID NO: 3, a VL CDR1 comprising the amino acid sequence of SEQ ID NO: 4, a VL CDR2 comprising the amino acid sequence of SEQ ID NO: 5, and a VL CDR3 comprising the amino acid sequence of SEQ ID NO: 6. In certain instances, the antibody or antigen binding fragment thereof comprises a VH comprising the amino acid sequence of SEQ ID NO: 13. In certain instances, the antibody or antigen-binding fragment thereof comprises a VL comprising the amino acid sequence of SEQ ID NO: 14. In certain instances, the antibody or antigen-binding fragment thereof further comprises a VH CDR1 comprising the amino acid sequence of SEQ ID NO: 7, a VH CDR2 comprising the amino acid sequence of SEQ ID NO: 8, a VH CDR3 comprising the amino acid sequence of SEQ ID NO: 9, a VL CDR1 comprising the amino acid sequence of SEQ ID NO: 10, a VL CDR2 comprising the amino acid sequence of SEQ ID NO: 11, and a VL CDR3 comprising the amino acid sequence of SEQ ID NO: 12. In certain instances, the antibody or antigen-binding fragment comprises a VH comprising the amino acid sequence of SEQ ID NO: 15. In certain instances, the antibody or antigen-binding fragment comprises a VL comprising the amino acid sequence of SEQ ID NO: 16.

In certain instances, an antibody or antigen-binding fragment thereof that specifically binds to a S. aureus ClfA protein, comprises the VH CDR1, VH CDR2, VH CDR3, VL CDR1, VL CDR2, and VL CDR3 of SAR72, SAR80, SAR113, SAR132, SAR352, SAR372, SAR510, SAR547, SAS1, SAS19, or SAS203. In certain instances, the CDRs are the Kabat-defined CDRs, the Chothia-defined CDRs, or the AbM-defined CDRs. In certain instances, the antibody or antigen-binding fragment comprises variable heavy chain and variable light chain sequences comprising the amino acid sequences set forth in (a) SEQ ID NOs: 17 and 18, respectively (b) SEQ ID NOs: 30 and 31, respectively, (c) SEQ ID NOs: 32 and 33, respectively, (d) SEQ ID NOs: 34 and 35, respectively, (e) SEQ ID NOs: 36 and 37, respectively, (f) SEQ ID NOs: 38 and 39, respectively, (g) SEQ ID NOs: 40 and 41, respectively, (h) SEQ ID NOs: 42 and 43 respectively (i) SEQ ID NOs: 44 and 45, respectively, (j) SEQ ID NOs: 46 and 47, respectively, or (k) SEQ ID NOs: 48 and 49, respectively.

In certain instances, an antibody or antigen-binding fragment thereof that specifically binds to a S. aureus ClfA protein, comprises a VH and a VL, wherein the VH comprises the amino acid sequence set forth in SEQ ID NO: 17, 30, 32, 34, 36, 38, 40, 42, 44, 46, or 48.

In certain instances, an antibody or antigen-binding fragment thereof that specifically binds to a S. aureus ClfA protein comprises a VH and a VL, wherein the VL comprises the amino acid sequence set forth in SEQ ID NO: 18, 31, 33, 35, 37, 39, 41, 43, 45, 47, or 49.

In certain instances, the antibody or antigen-binding fragment thereof further comprises a heavy chain constant region. In certain instances, the heavy chain constant region is selected from the group consisting of human immunoglobulin $IgG_1$, $IgG_2$, $IgG_3$, $IgG_4$, $IgA_1$, and $IgA_2$ heavy chain constant regions. In certain instances, the heavy chain constant region is a human $IgG_1$ constant region. In certain instances, the heavy chain constant region comprises an N3, N3E, or N3F mutation. In certain instances, the heavy chain constant region comprises a YTE mutation.

In certain instances, the antibody or antigen-binding fragment thereof further comprises a light chain constant region. In certain instances, the light chain constant region is selected from the group consisting of human immunoglobulin IgGκ and IgGλ light chain constant regions. In certain instances, the light chain constant region is a human IgGκ light chain constant region.

In certain instances, the antibody or antigen-binding fragment is a monoclonal antibody or antigen-binding fragment.

In certain instances, the antibody or antigen-binding fragment is a full-length antibody. In certain instances, the antibody or antigen-binding fragment is an antigen-binding fragment. In certain instances, the antigen-binding fragment comprises a Fab, Fab', F(ab')$_2$, single chain Fv (scFv), disulfide linked Fv, intrabody, IgGΔCH2, minibody, F(ab')$_3$, tetrabody, triabody, diabody, DVD-Ig, Fcab, mAb$^2$, (scFv)$_2$, or scFv-Fc.

In certain instances, an antibody that specifically binds to a S. aureus ClfA protein comprises a heavy chain comprising the amino acid sequence set forth in SEQ ID NO: 50 and a light chain comprising the amino acid sequence set forth in SEQ ID NO: 26.

In certain instances, the antibody or antigen-binding fragment thereof further comprises a detectable label.

Provided herein are also compositions comprising an antibody provided herein. In certain instances, a composition comprises an antibody provided herein and a pharmaceutically-acceptable carrier.

In certain instances, a composition comprises an antibody provided herein and an antibody or antigen-binding fragment that specifically binds to a S. aureus AT protein, and optionally a pharmaceutically-acceptable carrier. In certain instances, the antibody or antigen-binding fragment that specifically binds to a S. aureus AT protein comprises a VH CDR1 comprising the amino acid sequence of SEQ ID NO: 7, a VH CDR2 comprising the amino acid sequence of SEQ ID NO: 8, a VH CDR3 comprising the amino acid sequence of SEQ ID NO: 9, a VL CDR1 comprising the amino acid sequence of SEQ ID NO: 10, a VL CDR2 comprising the amino acid sequence of SEQ ID NO: 11, and a VL CDR3 comprising the amino acid sequence of SEQ ID NO: 12. In certain instances, the antibody or antigen-binding fragment that specifically binds to a S. aureus AT protein comprises a VH comprising the amino acid sequence of SEQ ID NO: 15. In certain instances, the antibody or antigen-binding fragment that specifically binds to a S. aureus AT protein comprises a VL comprising the amino acid sequence of SEQ ID NO: 16. In certain instances, the antibody or antigen-binding fragment that specifically binds to S. aureus AT protein comprises a heavy chain comprising the amino acid sequence of SEQ ID NO: 27. In certain instances, the antibody or antigen-binding fragment that specifically binds to S. aureus AT protein comprises a light chain comprising the amino acid sequence of SEQ ID NO: 28.

Provided herein are also methods of using an antibody provided herein. In certain instances, a method of treating or preventing a *S. aureus* infection in a subject comprises administering to the subject an antibody or antigen-binding fragment provided herein or a composition provided herein.

In certain instances, a method of treating or preventing a *S. aureus* infection in a subject comprises administering to the subject an antibody or antigen-binding fragment provided herein and an antibody or antigen-binding fragment that specifically binds to a *S. aureus* alpha toxin (AT) protein. In certain instances, the antibody or antigen-binding fragment that specifically binds to a *S. aureus* AT protein comprises a VH CDR1 comprising the amino acid sequence of SEQ ID NO: 7, a VH CDR2 comprising the amino acid sequence of SEQ ID NO: 8, a VH CDR3 comprising the amino acid sequence of SEQ ID NO: 9, a VL CDR1 comprising the amino acid sequence of SEQ ID NO: 10, a VL CDR2 comprising the amino acid sequence of SEQ ID NO: 11, and a VL CDR3 comprising the amino acid sequence of SEQ ID NO: 12. In certain instances, the antibody or antigen-binding fragment that specifically binds to a *S. aureus* AT protein comprises a VH comprising the amino acid sequence of SEQ ID NO: 15. In certain instances, the antibody or antigen-binding fragment that specifically binds to a *S. aureus* AT protein comprises a VL comprising the amino acid sequence of SEQ ID NO: 16. In certain instances, the antibody or antigen-binding fragment that specifically binds to *S. aureus* AT protein comprises a heavy chain comprising the amino acid sequence of SEQ ID NO: 27. In certain instances, the antibody or antigen-binding fragment that specifically binds to *S. aureus* AT protein comprises a light chain comprising the amino acid sequence of SEQ ID NO: 28. In certain instances, the anti-*S. aureus* ClfA antibody or antigen-binding fragment provided herein and the antibody or antigen-binding fragment that specifically binds to a *S. aureus* AT protein are administered simultaneously. In certain instances, the anti-*S. aureus* ClfA antibody or antigen-binding fragment provided herein and the antibody or antigen-binding fragment that specifically binds to a *S. aureus* AT protein are administered sequentially.

In certain instances, treating or preventing an *S. aureus* infection in a subject comprises inhibiting *S. aureus*-associated sepsis, inhibiting *S. aureus* agglutination, inhibiting thromboembolic lesion formation, toxin neutralization, inducing opsonophagocytosis, inhibiting *S. aureus* fibrinogen binding, inhibiting *S. aureus* agglutination, or any combination of the foregoing.

In certain instances, the subject has diabetes. In certain instances, the subject is human.

Provided herein are also polynucleotides. In certain instances, an isolated polynucleotide comprises a nucleic acid molecule encoding the VH or heavy chain of an antibody or antigen-binding fragment thereof provided herein. In certain instances, the nucleic acid molecule encodes the VH of SEQ ID NO: 13 or the heavy chain of SEQ ID NO: 25, 50, or 52.

In certain instances, an isolated polynucleotide comprises a nucleic acid molecule encoding the VL or light chain of an antibody or antigen-binding fragment thereof provided herein. In certain instances, the nucleic acid molecule encodes the VL of SEQ ID NO: 14 or the light chain of SEQ ID NO: 26.

In certain instances, an isolated polynucleotide comprises a nucleic acid molecule encoding the VH or heavy chain of an antibody or antigen-binding fragment thereof provided herein and the VH or light chain of the antibody or antigen-binding fragment thereof.

Also provided herein are vectors. In certain instances, an isolated vector comprises a polynucleotide provided herein.

Also provided herein are host cells. In certain instances, a host cell comprises a polynucleotide provided herein, a vector provided herein, or a first vector a polynucleotide provided herein and a second vector comprising a polynucleotide provided herein. In certain instances, the host cell is selected from the group consisting of CHO, NS0, PER-C6, HEK-293, and HeLa cells. In certain instances, the host cell is isolated.

Also provided herein are methods of producing antibodies or antigen-binding fragments. In certain instances, a method of producing an antibody or antigen-binding fragment thereof comprises culturing a host cell provided herein so that the antibody or antigen-binding fragment thereof is produced.

Also provided herein are methods for detecting detecting *S. aureus* or *S. aureus* ClfA. In certain instances, a method for detecting *S. aureus* or *S. aureus* ClfA in a sample comprises contacting the sample with an antibody or antigen-binding fragment thereof provided herein.

BRIEF DESCRIPTION OF THE SEVERAL VIEWS OF THE DRAWING(S)

FIG. 1 is a series of graphs which illustrate inhibition of fibrinogen binding to the three main ClfA genotypes as measured in the presence of serially diluted (from 666 µM to 2.55 µM) anti-ClfA mAb 11H10 (FIG. 1A) or SAR114 (FIG. 1B). Data are representative of three independent experiments.

FIG. 2 is a graph which illustrates agglutination of *S. aureus* clinical isolates in the presence of human plasma and anti-ClfA mAbs. FIG. 2 shows the minimum concentration of the 11H10 and SAR114 mAbs required to inhibit bacterial agglutination. Data are representative of two independent experiments. c-IgG was used as a negative control and did not show any inhibition at 200 µg/ml.

FIG. 3 is a series of graphs which illustrate opsonophagocytic killing (OPK) activity of the anti-ClfA monoclonal antibody SAR114 against the *S. aureus* clinical isolates ARC635(ST5) (FIG. 3A), SF8300 (ST8) (FIG. 3B), NRS383 (ST346) (FIG. 3C), NRS382 (ST5) (FIG. 3D), NRS384 (ST8) (FIG. 3E), and ARC2081 (ST30) (FIG. 3F). *S. aureus* strains were incubated with human HL-60 cells, human sera, and serial dilutions of SAR114 (squares) or c-IgC (circles). The graphs represent mean values±standard deviation (SD) of three independent experiments.

FIG. 4 is a graph which illustrates agglutination inhibition of multiple *S. aureus* types by the SAR114 monoclonal antibody. 112 *S. aureus* clinical isolates representing 40 different sequence types (ST) and some not found (NF) were tested as described in Example 1.

FIG. 5 shows graphs illustrating competition of SAR114 and 11H10 for binding to ClfA001 genotype. The graph in FIG. 5A shows results of an ELISA competition binding assay as described in Example 1. Data represent the mean values±standard deviation (SD). The graph in FIG. 5B shows results of the OCTECT® binding assay described in Example 1.

FIG. 6 provides graphs showing the effect of YTE and N3 mutations in anti-bacterial antibodies on opsonophagocytic killing (OPK). Cam004 (top panel) is an anti-*pseudomonas* antibody, and 2F4 (bottom panel) is an anti-S. aureus antibody. R347 antibody was used as a negative control. (See Example 2.)

FIG. 7 provides graphs showing that the N3 mutation does not reduce the ability of SAR114 in inhibiting of ClfA001, ClfA002, or ClfA1004 binding to fibrinogen. (See Example 2.)

FIG. 8 provides tables reporting the effects of N3F and N3Y mutations on SAR114 in agglutination and fibrinogen potency assays. (See Example 3.)

FIG. 9 provides graphs showing the effects of the N3 (N3W), N3F, and N3Y mutations on the pharmacokinetic (PK) in mice transgenic for human FcRn (top panel) and OPK (bottom panel) of SAR114. (See Example 3.)

FIGS. 10A-M are a series of graphs which illustrate that the combination of SAR114 and MEDI4893* monoclonal antibodies provides strain coverage in a lethal bacteremia mouse model as described in Example 4. The different S. aureus clinical isolates from diverse sequence types (ST), and ClfA genotypes tested included: NRS123 (ST1, ClfA012), NRS387 (ST5, ClfA002), ARC635 (ST5, ClfA002), 3049043 (ST5, ClfA002), 3049057 (ST8, ClfA001), SF8300 (ST8, Clf A001), 3049088 (ST30, ClfA004), 3049114 (ST30, ClfA004), ARC2784 (ST188, ClfA019), 9043, 9057, 9157, and 2784. The data shown are representative of three independent experiments. Dashed lines with a circle at the end represent mice treated with an IgG control antibody. Lines with a square at the end represent mice treated with SAR114 (15 mpk). Lines with an upward triangle at the end represent mice treated with MEDI4893* (15 mpk). Lines with a downward triangle at the end represent mice treated with SAR114 and MEDI4893* (7.5 mpk each). (See Example 4.)

FIG. 11 is a series of graphs illustrating that the combination of SAR114 and MEDI4893* monoclonal antibodies protects against CA-MRSA SF8300-induced IV lethal bacteremia in BKS.Cg-Dock7$^m$+/+Lepr$^{db}$/J diabetic mice (db/db). The horizontal bars in the bottom two panels represent the geometric mean CFU. The data are representative of three independent experiments. (See Example 5.)

FIG. 12 provides images demonstrating the effects of the combination of SAR114 and MEDI4893* monoclonal antibodies on liver damage in db/db mice exposed to CA-MRSA SF8300-induced IV lethal bacteremia, either by gross pathology (left) or after hematoxylin and eosin staining of section (right). (See Example 7.)

FIG. 13 is a series of graphs which illustrate that the combination of SAR114 and MEDI4893* monoclonal antibodies provides strain coverage for protection in a lethal bacteremia diabetic db/db mouse model. (See Example 8.)

FIG. 14 provides schematic representations of bispecific constructs using anti-ClfA mAb as a scaffold (FIG. 14A) or scFv of anti-AT mAb MEDI4893* linked via a 10-amino acid linker (GGGGx2) to the ClfA monoclonal antibody heavy chain N terminus (FIG. 14B) or heavy chain C terminus (FIG. 14C). (See Example 9.)

FIG. 15 is a series of graphs illustrating in vitro characterization of anti-ClfA SAR114 or 11H10/MEDI4893* BiS-Abs, as described in Example 9. FIGS. 15A and 15D illustrate BiS$_2$ and BiS$_3$ activities compared to MEDI4893* in an AT-mediated rabbit RBC hemolytic assay. Serial dilutions of BiSAbs and MEDI4893* were incubated with AT alone (FIG. 15A) or 10M excess of ClfA001 (FIG. 15D) and RBC. Percent hemolysis inhibition was calculated as follows: $100*(100-(OD_{AT+mAb})/(OD_{AT\ alone}))$. Data are representative of three independent experiments. FIGS. 15B and 15C illustrate the results of the immobilized fribrinogen binding assay described in Example 9. Serial dilutions of BiSAbs, SAR114 or 11H10 were incubated with ClfA alone (FIG. 15B) or with 10M excess of AT (FIG. 15C). Data represent the mean values standard deviation of three separate experiments. Percent inhibition binding was calculated as $100*(100-(OD_{ClfA+mAb})/(OD_{ClfA\ alone}))$.

FIG. 16 is a series of graphs illustrating inhibition of fibrinogen binding to the three main ClfA genotypes as described in Example 9. Inhibition of fibrinogen binding was measured in the presence of serial dilutions of the monoclonal antibodies 11H10 (FIG. 16A), SAR114 (FIG. 16B), or respective bispecific antibodies (FIG. 16C). A similar assay was conducted by saturating AT scFv in the presence of a 10M excess of AT (6.6 mM) (FIGS. 16D-F).

FIG. 17 is a series of graphs illustrating opsonophagocytic killing (OPK) activity of anti-ClfA/AT bispecific antibodies (BiS). S. aureus Newman isolate was incubated with human HL-60 cells, human sera, and serial dilutions of 11H10 parental monoclonal antibodies or 11H10-BiS molecules (FIG. 17A), or serial dilutions of SAR114 parental monoclonal antibodies or SAR114-BiS molecules (FIG. 17B). The graphs represent mean values±SD of two independent experiments. (See Example 9)

FIG. 18 is a series of graphs illustrating the efficacy of anti-ClfA mAb/MEDI4893* bispecific antibodies in a bacteremia mouse model. Balb/c mice (n=10) were passively immunized IP with SAR114/MEDI4893* BiS$_2$, BiS$_3$ or a combination of SAR114+MEDI4893* at the indicated concentrations, and IV infected 24 hours later with an LD$_{90}$ of S. aureus isolates SF8300 (6e$^7$ cfu) (FIG. 18A) or 3049057 (5e$^7$ cfu) (FIG. 18B). Protective efficacy for 11H10/MEDI4893* BiS$_2$, BiS$_3$ or 11H10+MEDI4893* mAbs was evaluated against SF8300 (FIG. 18C) or 30419057 (FIG. 18D) challenge. Survival was monitored for 2 weeks. Results were analyzed with a Log Rank (Mantel Cox) test. Statistical analysis versus c-IgG were considered statistically different if p<0.05, and indicated with an asterisk (*). Data are representative of three independent experiments. (See Example 10.)

FIG. 19 is a series of graphs illustrating that ClfA sequesters SAR114/MEDI4893* BiSAb in a lethal pneumonia mouse model. C57/B6 mice (n=10) were passively immunized IP with BiS$_2$, BiS$_3$, MEDI4893* or the SAR114+MEDI4893* mAb combination at the indicated concentrations, and intranasally (IN) infected 24 hours later with 1.5e$^6$ cfu of S. aureus isolates SF8300 (FIG. 19A) or SF8300 ΔclfA isogenic mutant (FIG. 19B). Survival was monitored for 6 days. Results were analyzed with a Log Rank (Mantel Cox) test. Statistical analysis versus c-IgG were considered statistically different if p<0.05. Data are representative of three independent experiments. (See Example 11.)

DETAILED DESCRIPTION OF THE INVENTION

Figure 2:
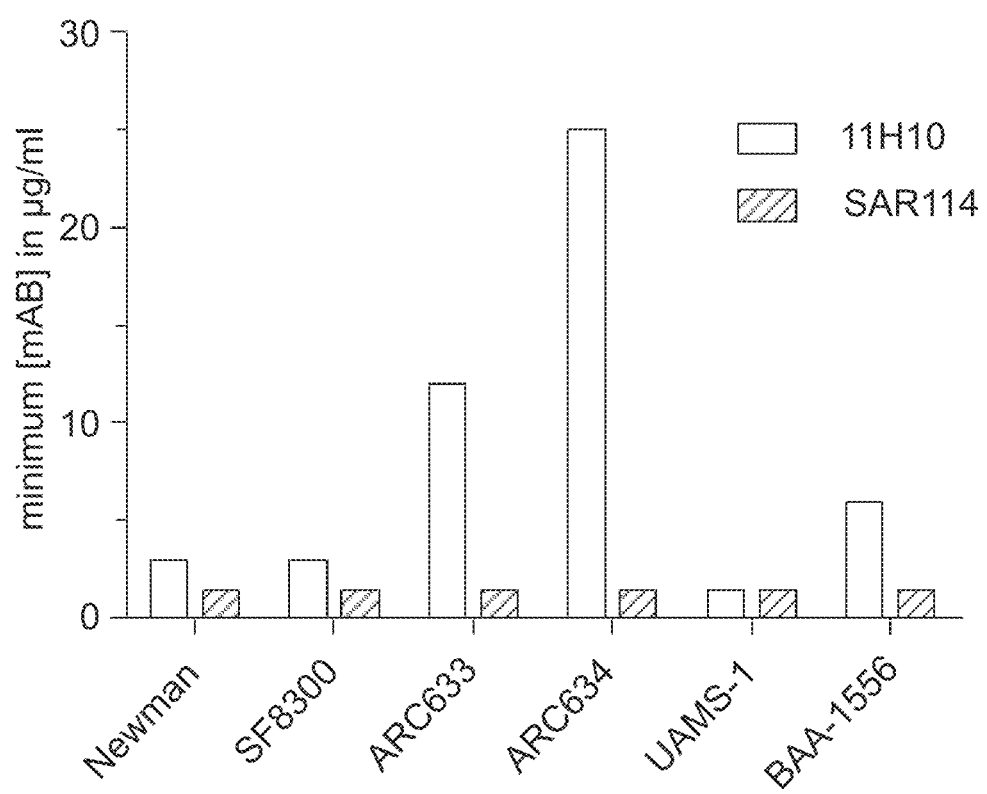
Figure 3:
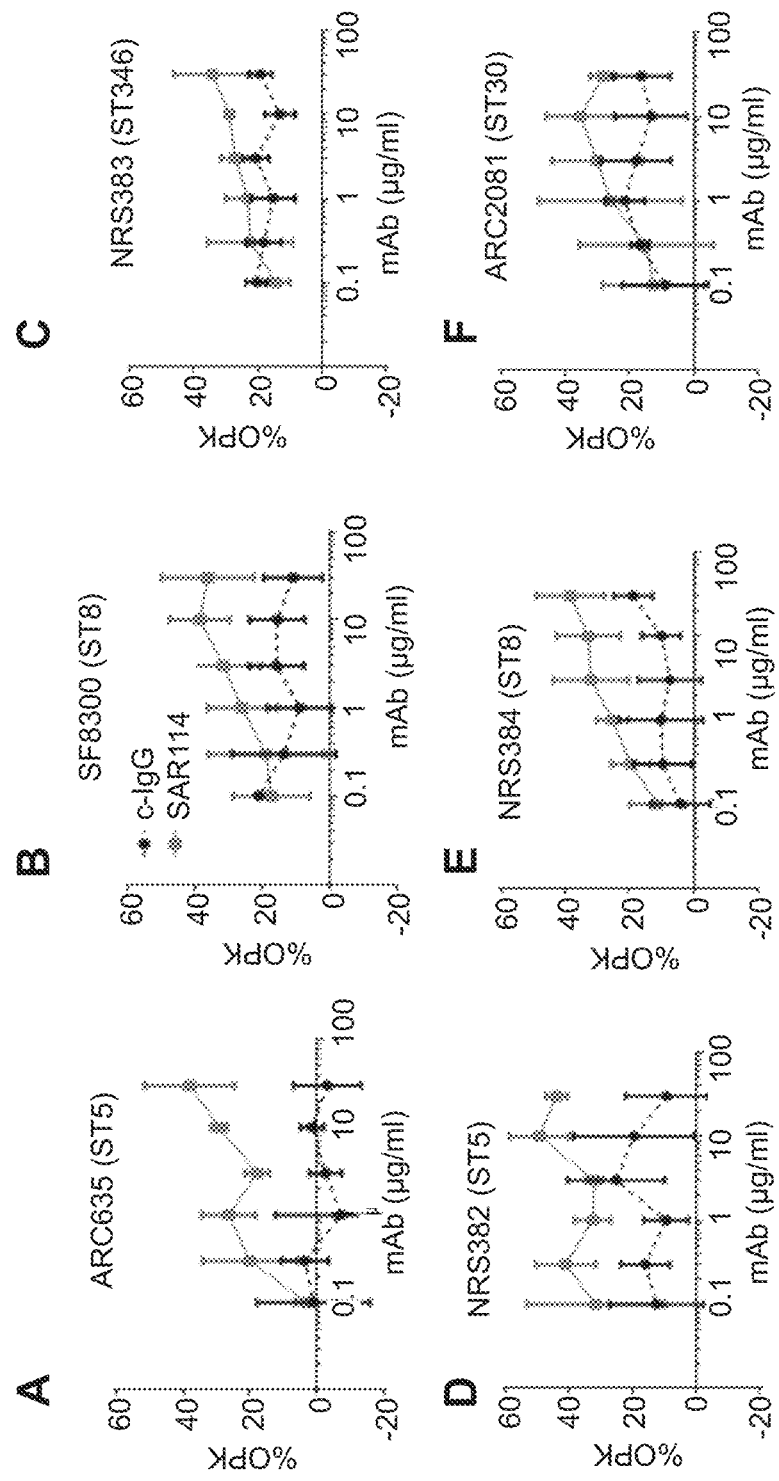

The present disclosure provides antibodies and antigen-binding fragments thereof (e.g., monoclonal antibodies and antigen-binding fragments thereof) that bind to Staphylococcus aureus (S. aureus) clumping factor A (ClfA) protein (and optionally also to S. aureus alpha toxin (AT) protein. The present disclosure also provides compositions comprising such antibodies or fragments thereof, as well as methods of using such antibodies, fragments thereof, or compositions.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, chimeric antibodies, humanized antibodies, human antibodies, fusion proteins comprising an antibody, and any other modified immunoglobulin molecule so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

The term "monoclonal antibodies," as used herein, refers to antibodies that are produced by a single clone of B-cells and bind to the same epitope. In contrast, the term "polyclonal antibodies" refers to a population of antibodies that are produced by different B-cells and bind to different epitopes of the same antigen.

The term "antibody fragment" refers to a portion of an intact antibody. An "antigen-binding fragment," "antigen-binding domain," or "antigen-binding region," refers to a portion of an intact antibody that binds to an antigen. An antigen-binding fragment can contain the antigenic determining regions of an intact antibody (e.g., the complementarity determining regions (CDR)). Examples of antigen-binding fragments of antibodies include, but are not limited to Fab, Fab', F(ab')2, and Fv fragments, linear antibodies, and single chain antibodies. An antigen-binding fragment of an antibody can be derived from any animal species, such as rodents (e.g., mouse, rat, or hamster) and humans or can be artificially produced.

A whole antibody typically consists of four polypeptides: two identical copies of a heavy (H) chain polypeptide and two identical copies of a light (L) chain polypeptide. Each of the heavy chains contains one N-terminal variable (VH) region and three C-terminal constant (CHI, CH2 and CH3) regions, and each light chain contains one N-terminal variable (VL) region and one C-terminal constant (CL) region. The variable regions of each pair of light and heavy chains form the antigen binding site of an antibody. The VH and VL regions have the same general structure, with each region comprising four framework regions, whose sequences are relatively conserved. The term "framework region," as used herein, refers to the relatively conserved amino acid sequences within the variable region which are located between the hypervariable or complementary determining regions (CDRs). There are four framework regions in each variable domain, which are designated FR1, FR2, FR3, and FR4. The framework regions form the β sheets that provide the structural framework of the variable region (see, e.g., C. A. Janeway et al. (eds.), *Immunobiology*, 5th Ed., Garland Publishing, New York, N.Y. (2001)). The three CDRs, known as CDR1, CDR2, and CDR3, form the "hypervariable region" of an antibody, which is responsible for antigen binding.

The term "Kabat numbering" and like terms are recognized in the art and refer to a system of numbering amino acid residues in the heavy and light chain variable regions of an antibody or an antigen-binding fragment thereof. In certain aspects, CDRs can be determined according to the Kabat numbering system (see, e.g., Kabat E A & Wu T T (1971) Ann NY Acad Sci 190: 382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In a specific embodiment, the CDRs of the antibodies described herein have been determined according to the Kabat numbering scheme.

Chothia refers instead to the location of the structural loops (Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

| Loop | Kabat | AbM | Chothia |
|------|-------|-----|---------|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 ... 34 |
| | | | (Kabat Numbering) |
| H1 | H31-H35 | H26-H35 | H26-H32 |
| | | | (Chothia Numbering) |
| H2 | H50-H65 | H50-H58 | H52-H56 |
| H3 | H95-H102 | H95-H102 | H95-H102 |

In one embodiment, the composition comprises a first antibody or antigen-binding fragment thereof (e.g. a monoclonal antibody or fragment) that specifically binds to a *Staphylococcus aureus* clumping factor A protein (ClfA) and a second antibody or antigen-binding fragment thereof (e.g. a monoclonal antibody or fragment) that specifically binds to a *S. aureus* alpha toxin (AT) protein. Among the many *S. aureus* surface adhesins, clumping factor A (ClfA) has been demonstrated to play an important role in serious bloodstream infections (Foster et al., *Nat. Rev. Microbiol.*, 12: 49-62 (2014); and Murphy et al., *Hum. Vaccin.*, 7(Suppl): 51-59 (2011)). ClfA binds fibrinogen and facilitates both bacterial adherence to fibrinogen and bacterial clumping, both of which are key attributes in the development of an *S. aureus* bloodstream infection (Vaudaux et al., *Infect. Immun.*, 63: 585-590 (1995); McDevitt et al., *Mol. Microbiol.*, 11: 237-248 (1994); and McDevitt et al., *Eur. J. Biochem.*, 247: 416-424 (1997)). ClfA bound to fibrin or fibrinogen at a site of injury or coated on an indwelling device can facilitate bacterial colonization (Foster et al., supra) and bacterial clumping, which is thought to enhance bacterial invasiveness (McDevitt et al., *Eur. J. Biochem.*, 247: 416-424 (1997); McAdow et al., *PLoS Pathog.*, 7:e1002307 (2011); Flick et al., *Blood*, 121: 1783-1794 (2013); and Rothfork et al., *J. Immunol.*, 171: 5389-5395 (2003)). ClfA also has been reported to impair complement deposition required for opsonophagocytic bacterial killing (OPK) (Hair et al., *Infect. Immun.,* 78: 1717-1727 (2010)). Consistent with these observations, isogenic ΔclfA mutants exhibited reduced virulence in infection models (McAdow et al., supra; Josefsson et al., *PLoS One,* 3: e2206 (2008); and Josefsson et al., *J Infect. Dis.,* 184: 1572-1580 (2001)). In addition, passive immunization with human anti-ClfA-enriched intravenous (i.v.) immunoglobulin (Ig) (INH-A21 or Veronate) or a monoclonal antibody (tefibazumab or Aurexis) improved disease outcomes for patients with *S. aureus* bloodstream infections (Vernachio et al., *Antimicrob. Agents Chemother.,* 47: 3400-3406 (2003); and Vernachio et al., *Antimicrob. Agents Chemother.,* 50: 511-518 (2006)). However, these antibody preparations failed to improve outcomes in clinical studies of prophylaxis or adjunctive therapy with vancomycin to prevent or treat *S. aureus* bacteremia in very-low-birth-weight infants (DeJonge et al., *J. Pediatr.,* 151: 260-265 (2007); Capparelli et al., *Antimicrob. Agents Chemother.,* 49: 4121-4127 (2005); and Bloom et al., *Pediatr. Infect. Dis.,* 24: 858-866 (2005)). ClfA structure and function is described in detail in, for example, McDevitt et al., *Mol. Microbiol.,* 11: 237-248 (1994)).

Alpha toxin (AT) is a key virulence factor in several *S. aureus* diseases, including pneumonia, skin and soft tissue infections (SSTI), and bacteremia (Bubeck Wardenburg, J. and O. Schneewind, *J. Exp. Med.,* 205: 287-294 (2008); Inoshima et al., *J. Invest. Dermatol.,* 132: 1513-1516 (2012); and Foletti et al., supra). Passive immunization with anti-AT monoclonal antibodies reduced disease severity in pneumonia and dermonecrosis models (Hua et al., *Antimicrob. Agents Chemother.,* 58: 1108-1117 (2014); Tkaczyk et al., *Clin. Vaccine Immunol.,* 19: 377-385 (2012); and Ragle, B. E. and J. Wardenburg Bubeck, *Infect. Immun.,* 77: 2712-2718 (2009)), and vaccination with an AT toxoid containing an H35L mutation (ATH35L) protected against death in mouse lethal bacteremia and pneumonia models (Bubeck Wardenburg, supra, Foletti et al., supra, Hua et al., supra, Ragle, supra, Menzies, B. E. and D. S Kernodle, *Infect. Immun.,* 77: 2712-2718 (2009); and Adhikari et al., *PLoS One,* 7: e38567 (2012)). AT contributes to multiple aspects of *S. aureus* pathogenesis during bacteremia and sepsis, including stimulating a hyperinflammatory response characteristic of sepsis and activating ADAM10-mediated cleavage of endothelial tight junctions, leading to a loss in vascular integrity (Powers et al., *J Infect. Dis.,* 206: 352-356 (2012); Wilke, G. A. and J. Bubeck Wardenburg, *Proc. Natl. Acad. Sci. USA,* 107: 13473-13478 (2010); and Becker et al., *J Innate Immun.,* 6: 619-631 (2014)). AT also has been demonstrated to target platelets, which prevents repair of the injured endothelial barrier and promotes organ dysfunction through platelet-neutrophil aggregate formation (Powers et al., *Cell Host Microbe,* 17: 775-787 (2015)). Alpha toxin structure and function is described in detail in, for example, Bhakdi, S. and J. Tranum-Jensen, *Microbiol. Mol. Biol. Rev.,* 55(4): 733-751 (1991).

Monoclonal and polyclonal antibodies which bind ClfA are known in the art (see, e.g., U.S. Pat. No. 7,364,738; Hall et al., *Infect. Immun.,* 71(12): 6864-6870 (2003); and Vernachio et al., *Antimicrob. Agents Chemother.,* 47(11): 3400-3406 (2003)) and are commercially available from sources such as, for example, Creative Biolabs (Shirley, N.Y.). As discussed above, while some anti-ClfA monoclonal antibodies (e.g., the 11H10 monoclonal antibody described in Tkaczyk et al., MBio., 7(3). pii: e00528-16 (2016)) have shown efficacy against *S. aureus* infections in bacteremia models, such antibodies have been found to exhibit reduced affinity for ClfA and impaired inhibition of fibrinogen binding to ClfA founder sequence (ClfA002) expressed by certain strains of methicillin-resistant *Staphylococcus aureus* (MRSA). As such, the present disclosure provides an antibody or antigen-binding fragment thereof (e.g., a monoclonal antibody or fragment) that specifically binds to ClfA with greater than 100-fold increased affinity for three prominent ClfA variants, including ClfA002, and potent inhibition of bacterial agglutination by 112 diverse clinical isolates. In this regard, in one embodiment the first antibody or antigen-binding fragment thereof (e.g., monoclonal antibody or fragment) of the composition described herein specifically binds to ClfA and comprises, consists essentially of, or consists of (i) a heavy chain polypeptide comprising a complementarity determining region 1 (CDR) amino acid sequence of SEQ ID NO: 1, a CDR2 amino acid sequence of SEQ ID NO: 2, and a CDR3 amino acid sequence of SEQ ID NO: 3, and (ii) a light chain polypeptide comprising a CDR1 amino acid sequence of SEQ ID NO: 4, a CDR2 amino acid sequence of SEQ ID NO: 5, and a CDR3 amino acid sequence of SEQ ID NO: 6. In another embodiment, the heavy chain polypeptide of the first antibody or antigen-binding fragment comprises (e.g., monoclonal antibody or fragment), consists essentially of, or consists of a variable region amino acid sequence of SEQ ID NO: 13 and the light chain polypeptide of the first antibody or antigen-binding fragment comprises, consists essentially of, or consists of, a variable region amino acid sequence of SEQ ID NO: 14. In certain instances, the antibody or antigen-binding fragment (e.g., monoclonal antibody or fragment) comprises a heavy chain constant domain comprising the amino acid sequence of CSYHLC (SEQ ID NO: 21), MHEACSYHLCQKSLSLS (SEQ ID NO: 23), or SEQ ID NO:24.

Monoclonal and polyclonal antibodies which bind AT also are known in the art (see, e.g., Hua et al., *Antimicrob. Agents Chemother.,* 58(2): 1108-1117 (2014); and Oganesyan et al., *J. Biol. Chem.,* 289: 29874-29880 (2014)) and are commercially available from sources such as, for example, Sigma Aldrich (St. Louis, Mo.) and AbCam (Cambridge, Mass.). In one embodiment, the second antibody or antigen-binding fragment (e.g., monoclonal antibody or fragment) of the composition described herein specifically binds to *S. aureus* alpha toxin (AT) protein and comprises, consists essentially of, or consists of (i) a heavy chain polypeptide comprising a CDR1 amino acid sequence of SEQ ID NO: 7, a CDR2 amino acid sequence of SEQ ID NO: 8, and a CDR3 amino acid sequence of SEQ ID NO: 9, and (ii) a light chain polypeptide comprising a CDR1 amino acid sequence of SEQ ID NO: 10, a CDR2 amino acid sequence of SEQ ID NO: 11, and a CDR3 amino acid sequence of SEQ ID NO: 12. In another embodiment, the heavy chain polypeptide of the second antibody or antigen-binding fragment (e.g., monoclonal antibody or fragment) comprises, consists essentially of, or consists of a variable region amino acid sequence of SEQ ID NO: 15 and/or the light chain polypeptide of the second monoclonal antibody comprises, consists essentially of, or consists of a variable region amino acid sequence of SEQ ID NO: 16.

Sequences of exemplary anti-ClfA and anti-AT antibodies are provided below. In certain instances, an antibody or antigen-binding fragment thereof described herein binds to ClfA and/or AT and comprises the six CDRs of an antibody listed in the two tables below (i.e., the three VH CDRs of the antibody listed in the first table and the three VL CDRs of the same antibody listed in the second table). The anti-AT antibody MEDI4893 is the half-life extended (YTE) version of "LC10" described previously in International Patent Application Publications WO 2012/109285 and WO 2014/074540 (both of which are herein incorporated by reference in their entireties). MEDI4893* does not contain the YTE mutation.

VH CDR Amino Acid Sequences

| Antibody | VH CDR1 (SEQ ID NO:) | VH CDR2 (SEQ ID NO:) | VH CDR3 (SEQ ID NO:) |
|---|---|---|---|
| SAR114 | NSYWS (SEQ ID NO: 1) | YLYSSGRTNYTPSLKS (SEQ ID NO: 2) | THLGGFHYGGGFWFDP (SEQ ID NO: 3) |
| MEDI4893 and MEDI4893* | SHDMH (SEQ ID NO: 7) | GIGTAGDTYYPDSVKG (SEQ ID NO: 8) | DRYSPTGHYYGMDV (SEQ ID NO: 9) |

VL CDR Amino Acid Sequences

| Antibody | VL CDR1 (SEQ ID NO:) | VL CDR2 (SEQ ID NO:) | VL CDR3 (SEQ ID NO:) |
|---|---|---|---|
| SAR114 | RASQSITSYLN (SEQ ID NO: 4) | ASSSLQS (SEQ ID NO: 5) | QESYSTPPT (SEQ ID NO: 6) |
| MEDI4893 and MEDI4893* | RASQSISSWLA (SEQ ID NO: 10) | KASSLES (SEQ ID NO: 11) | KQYADYWT (SEQ ID NO: 12) |

In certain instances, an antibody or antigen-binding fragment thereof described herein binds to ClfA and/or AT and comprises the VH of an antibody listed in the following table, e.g., in combination with a VL.

Variable Heavy Chain (VH) Amino Acid Sequence

| Antibody | VH Amino Acid Sequence (SEQ ID NO) |
|---|---|
| SAR114 | QVQLQESGPGLVKPSETLSLTCTVSGGSIQNSYWSWIRQPPGKGLEWIGYLYSSGRTNYTPSLKSRVTISVDTSKNQFSLKLSSVTAADTAVYYCARTHLGGFHYGGGFWFDPWGQGTLVTVSS (SEQ ID NO: 13) |
| MEDI4893 and MEDI4893* | EVQLVESGGGLVQPGGSLRLSCAASGFTFSSHDMHWVRQATGKGLEWVSGIGTAGDTYYPDSVKGRFTISRENAKNSLYLQMNSLRAGDTAVYYCARDRYSPTGHYYGMDVWGQGTTVTVSS (SEQ ID NO: 15) |
| SAR72 | EVQLVESGGGLVKPGGSLRVSCAASGFSFRNALMSWVRQAPGKGLEWVGRSKTDGGTTDYAAPVKGRFTISRDDSKNTLYLQMNSLKTEDTAVYYCTTGPGGGPPGDYYYDGMDVWGQGTTVTVSS (SEQ ID NO: 17) |
| SAR80 | EVQLVESGGDLVKPGGSLRLSCAASGFTFSDAWMTWVRQAPGKGLEWVGRIRSKTAGGTTDYAAPVKGRFTISRDDSKNTLYLQMTSLKIEDTALYYCMTDGLGLLNFGDSDPHHYWGQGTRVTVSS (SEQ ID NO: 30) |
| SAR113 | EVQLVQSGAEVKKPGESLKISCKAXGYXFTSYWIGWVRQVPGKGLEWMGIIYPGDSDTRHSPSFQGQVTISVDKSISTAYLQWSSLKASDSAMYYCARHQSGSHGFDAFEIWGQGTMVTVSS (SEQ ID NO: 32) |
| SAR132 | EVQLVQSGAEVKKPGESLKISCKGSGYNFTNYWIAWVRQMPGKGLEWMGITYSGDSDTRYSPSFLGQVSISVDKSFTTAYLQWRSLKASDTAMYYCARRPGGQKPYDYWGQGTLVTVSS (SEQ ID NO: 34) |
| SAR352 | EVQLVESGGGLVKPGGSLRLSCAASGFTFNNAWMSWVRQAPGKGLEWVGRIKSETAGGTTDYAAPVKGRFSISRDDSRNTLYLEMNSLKTEDTAVYYCTTDSYTPLEEPCPNGVCYTYYYYGMDVWGQGTTVTVSS (SEQ ID NO: 36) |
| SAR372 | EVQLVESGGGLVQPGGSLRLSCAASGFIFNRYSMNWVRQAPGKGLEWVSYISSSSSPIYYADSVKGRFTISRDNAKNSLYLQMNSLRDEDTAVYCASRVTLGLEFDFWGQGTLVTVSS (SEQ ID NO: 38) |
| SAR510 | QVTLRESGPALVKPTQTLTLTCTFSGFSLSTSGMCVGWIRQPPGKALEWLALIEWDDDKYYNTSLKTRLSISKDTSKNQVVLTMTNMDPVDTGTYYCARHSSSSRGFDYWGQGALVTVSS (SEQ ID NO: 40) |
| SAR547 | EVQLVQSGAEVKKPGESLKISCKGSGYSFTTYWIAWVRQMPGKGLEWMGITYPGDSDTRYSPSFQGQVTISADKSTATAYLQWSSLNASDSAMYYCARQGGSHGYDAFHMWGQGTMVTVSS (SEQ ID NO: 42) |

-continued

| Antibody | VH Amino Acid Sequence (SEQ ID NO) |
|---|---|
| SAS1 | EVQLLESGGGLVQPGGSLRLSCTASGFTFSTYALNWVRQAPGKGLE WVAGINGTGYNTYYADSVRGRFTISRDNSKNTVTLEMNSLRVEDTA TYYCHKVPWWGQGTLVSVSS (SEQ ID NO: 44) |
| SAS19 | QVQLQESGPRLVKPSETLSLTCFVSGGSINNSYWTWIRQPPGQGLEWI GFVFSSGRTNYSPSLKSRVTISVDTSKNLFSLRLTSVTAADTAVYFCA RQVHYDFWSGYSLTKTNWFDPWGQGTLVTVSS (SEQ ID NO: 46) |
| SAS203 | QVQLQESGPGLVKPSETLSLTCVVSGGSINNSYWTWIRQPPGQGLEWI GFVYSSGRTYYSPSLKSRVTISVDTSKNFFSLRLNSVTAADTAVYFCA RQVHYDLWSGYSLTKTNWFDPWGQGTLVTVSS (SEQ ID NO: 48) |

In certain instances, an antibody or antigen-binding fragment thereof described herein binds to ClfA and/or AT and comprises the VL of an antibody listed in the following table, e.g., in combination with a VH, optionally the VH of the same antibody listed in the preceding table.

Variable Light Chain (VL) Amino Acid Sequence

| Antibody | VL Amino Acid Sequence (SEQ ID NO) |
|---|---|
| SAR114 | DIQMTQSPSSLSASVGDRVTITCRASQSITSYLNWYQQKPGKAPKLLI YASSSLQSGVPSRFSGSGSGTDFTLTISSLQPEDFATYYCQESYSTPPTF GQGTKVEIK (SEQ ID NO: 14) |
| MEDI4893 and MEDI4893* | DIQMTQSPSTLSASVGDRVTITCRASQSISSWLAWYQQKPGKAPKLLI YKASSLESGVPSRFSGSGSGTEFTLTISSLQPDDFATYYCKQYADYWT FGQGTKVEIK (SEQ ID NO: 16) |
| SAR72 | SYELTQPPSVSVSPGQTARITCSGDAVPKKYAYWYQQKSGQAPVLVI YEDKKRPSGIPERFSGSSSGTMATLTISGAQVEDEADYYCYSTDSSEG VFGGGTKLTVL (SEQ ID NO: 18) |
| SAR80 | SYELTQPPSVSVSPGQTARITCSGDALPKKYAYWYQQKSGQAPVLVI HEDTKRPSGIPERFSGSSSGTMATLTISGAQVEDEADYHCYSTDSSGV VFGGGTKLTVL (SEQ ID NO: 31) |
| SAR113 | DIVLTQSPDSLAVSLGERATINCKSSQGVLSRSNNKNYLAWYQQKPG QPPKLLIYWASTRESGVPDRFSGSGSGTDFTLTISSLQAEDVAVYYCQ QYYNNLRTFGQGTKVEIR (SEQ ID NO: 33) |
| SAR132 | DIQMTQSPSTLSASVGDRVTITCRASQRISNWLAWYQQKPGKAPKLLI YKASTLESEVPSRFSGSGSGTEFTLTISSLQPDDLATYYCHQYISYYTF GQGTKLEIK (SEQ ID NO: 35) |
| SAR352 | QSVLTQPPSVSAAPGEKVTISCSGSSSNIGANSVSWYQQFPGTAPKLLI YDNDKRPSGVPDRFSGSKSGTSATLGITGLQTGDEADYYCGTWVGIL SAGWVFGGGTKLTVL (SEQ ID NO: 37) |
| SAR372 | EIVLTQSPATLSLSPGERATLSCRASQSVSSNLAWYQQKPGQAPRLLI YDASNRATGIPDRFSGSGSGTDFTLTISSLKPEDFAVYYCQLRSNWAY TFGQGTKLEIK (SEQ ID NO: 39) |
| SAR510 | SYGLTQPPSVSVSPGQTARITCSGDALAKQYVYWYQQKPGQAPVLVI DKDRERPSGIPERFSGSSSGTTVTLTISGVQAEDEADYYCQSADSSRT YVFGTGTKVTVL (SEQ ID NO: 41) |
| SAR547 | DVVMTQSPLSLPVTLGQPASISCRSSQSLVHSDGNTYLNWFQQRPGQ SPRRLIYKVSNRDSGVPDRFSGSGSGTDFTLKISRVEAEDVGVYYCM QGTHLTWTFGQGTKVEIK (SEQ ID NO: 43) |
| SAS1 | DIVLTQSPESLAVSLGERATISCKSSQSLFFKSNNKNYLAWYQQKPGQ PPKVIIYWASTRESGVPARFSGSGSGTDFTLTISSLQAEDVAVYFCHQ YYSTQYSFGQGTKLEIK (SEQ ID NO: 45) |
| SAS19 | DIQMTQSPSSLSASVGDTVTITCRTSQSISNFLNWYQQKPGKAPKLLIY AASSLQSGVPSRVNGSTSGTEFTLTLSSLQPEDFATYYCQQSYSTPWT FGQGTKVEIK (SEQ ID NO: 47) |
| SAS203 | DIQMTQSPSSLSASVGDTVTITCRTSQSISNFLNWYQQKPGKAPKLLIY AASSLQSGVPSRFNGSTSGTDFTLTLSSLQPEDFATYYCQQSYSTPWT FGQGTKVEIK (SEQ ID NO: 49) |

In certain instances, an antibody or antigen-binding fragment thereof described herein binds to ClfA and/or AT and comprises the heavy chain of an antibody listed in the following table, e.g., in combination with a light chain.

Full-Length Heavy Chain Amino Acid Sequences

| Antibody | Full-Length Heavy Chain Amino Acid Sequence (SEQ ID NO) |
|---|---|
| SAR114 | QVQLQESGPGLVKPSETLSLTCTVSGGSIQNSYWSWIRQPPGKGLEW IGYLYSSGRTNYTPSLKSRVTISVDTSKNQFSLKLSSVTAADTAVYYC ARTHLGGFHYGGGFWFDPWGQGTLVTVSSASTKGPSVFPLAPSSKS TSGGTAALGCLVKDYFPEPVTVSWNSGALTSGVHTFPAVLQSSGLY SLSSVVTVPSSSLGTQTYICNVNHKPSNTKVDKRVEPKSCDKTHTCP PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSREEMTKNQVSLT CLVKGFYPSDIAVEWESNGQPENNYKTTPPVLDSDGSFFLYSKLTVD KSRWQQGNVFSCSVMHEALHNHYTQKSLSLSPGK (SEQ ID NO: 25) |
| SAR114 N3 | QVQLQESGPGLVKPSETLSLTCTVSGGSIQNSYWSWIRQPPGKGLEW IGYLYSSGRTNYTPSLKSRVTISVDTSKNQFSLKLSSVTAADTAVYYC ARTHLGGFHYGGGFWFDPWGQGTLVTVSSASTKGPSVFPLAPSSKS TSGGTAALGCLVKDYFPEPVTVSWNSGALTSGVHTFPAVLQSSGLY SLSSVVTVPSSSLGTQTYICNVNHKPSNTKVDKRVEPKSCDKTHTCP PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSREEMTKNQVSLT CLVKGFYPSDIAVEWESNGQPENNYKTTPPVLDSDGSFFLYSKLTVD KSRWQQGNVFSCSVMHEACSWHLCQKSLSLSPGK (SEQ ID NO: 52) |
| SAR114 N3Y | QVQLQESGPGLVKPSETLSLTCTVSGGSIQNSYWSWIRQPPGKGLEW IGYLYSSGRTNYTPSLKSRVTISVDTSKNQFSLKLSSVTAADTAVYYC ARTHLGGFHYGGGFWFDPWGQGTLVTVSSASTKGPSVFPLAPSSKS TSGGTAALGCLVKDYFPEPVTVSWNSGALTSGVHTFPAVLQSSGLY SLSSVVTVPSSSLGTQTYICNVNHKPSNTKVDKRVEPKSCDKTHTCP PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSREEMTKNQVSLT CLVKGFYPSDIAVEWESNGQPENNYKTTPPVLDSDGSFFLYSKLTVD KSRWQQGNVFSCSVMHEACSYHLCQKSLSLSPGK (SEQ ID NO: 50) |
| MEDI4893 | EVQLVESGGGLVQPGGSLRLSCAASGFTFSSHDMHWVRQATGKGL EWVSGIGTAGDTYYPDSVKGRFTISRENAKNSLYLQMNSLRAGDTA VYYCARDRYSPTGHYYGMDVWGQGTTVTVSSASTKGPSVFPLAPSS KSTSGGTAALGCLVKDYFPEPVTVSWNSGALTSGVHTFPAVLQSSG LYSLSSVVTVPSSSLGTQTYICNVNHKPSNTKVDKRVEPKSCDKTHT CPPCPAPELLGGPSVFLFPPKPKDTLYITREPEVTCVVVDVSHEDPEV KFNWYVDGVEVHNAKTKPREEQYNSTYRVVSVLTVLHQDWLNGK EYKCKVSNKALPAPIEKTISKAKGQPREPQVYTLPPSREEMTKNQVS LTCLVKGFYPSDIAVEWESNGQPENNYKTTPPVLDSDGSFFLYSKLT VDKSRWQQGNVFSCSVMHEALHNHYTQKSLSLSPGK (SEQ ID NO: 27) |
| MEDI4893* | EVQLVESGGGLVQPGGSLRLSCAASGFTFSSHDMHWVRQATGKGL EWVSGIGTAGDTYYPDSVKGRFTISRENAKNSLYLQMNSLRAGDTA VYYCARDRYSPTGHYYGMDVWGQGTTVTVSSASTKGPSVFPLAPSS KSTSGGTAALGCLVKDYFPEPVTVSWNSGALTSGVHTFPAVLQSSG LYSLSSVVTVPSSSLGTQTYICNVNHKPSNTKVDKRVEPKSCDKTHT CPPCPAPELLGGPSVFLFPPKPKDTLMISRTPEVTCVVVDVSHEDPEV KFNWYVDGVEVHNAKTKPREEQYNSTYRVVSVLTVLHQDWLNGK EYKCKVSNKALPAPIEKTISKAKGQPREPQVYTLPPSREEMTKNQVS LTCLVKGFYPSDIAVEWESNGQPENNYKTTPPVLDSDGSFFLYSKLT VDKSRWQQGNVFSCSVMHEALHNHYTQKSLSLSPGK (SEQ ID NO: 51) |

In certain instances, an antibody or antigen-binding fragment thereof described herein binds to ClfA and/or AT and comprises the light chain of an antibody listed in the following table, e.g., in combination with a heavy chain, optionally the heavy chain of the same antibody listed in the preceding table.

Full-Length Light Chain Amino Acid Sequences

| Antibody | Full-Length Light Chain Amino Acid Sequence (SEQ ID NO) |
|---|---|
| SAR114 | DIQMTQSPSSLSASVGDRVTITCRASQSITSYLNWYQQKPGKAPKLLI YASSSLQSGVPSRFSGSGSGTDFTLTISSLQPEDFATYYCQESYSTPPT FGQGTKVEIKRTVAAPSVFIFPPSDEQLKSGTASVVCLLNNFYPREAK VQWKVDNALQSGNSQESVTEQDSKDSTYSLSSTLTLSKADYEKHKV YACEVTHQGLSSPVTKSFNRGEC (SEQ ID NO: 26) |
| MEDI4893 and MEDI4893* | DIQMTQSPSTLSASVGDRVTITCRASQSISSWLAWYQQKPGKAPKLL IYKASSLESGVPSRFSGSGSGTEFTLTISSLQPDDFATYYCKQYADYW TFGQGTKVEIKRTVAAPSVFIFPPSDEQLKSGTASVVCLLNNFYPREA KVQWKVDNALQSGNSQESVTEQDSKDSTYSLSSTLTLSKADYEKHK VYACEVTHQGLSSPVTKSFNRGE (SEQ ID NO: 28) |

In certain aspects, the CDRs of an antibody or antigen-binding fragment thereof can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34).

In certain aspects, provided herein are antibodies and antigen-binding fragments thereof that comprise the Chothia VH and VL CDRs of the SAR114 and/or MEDI4893* antibodies. In certain embodiments, antibodies or antigen-binding fragments thereof comprise one or more CDRs, in which the Chothia and Kabat CDRs have the same amino acid sequence. In certain embodiments, provided herein are antibodies and antigen-binding fragments thereof comprise combinations of Kabat CDRs and Chothia CDRs.

In certain aspects, the CDRs of an antibody or antigen-binding fragment thereof can be determined according to the IMGT numbering system as described in Lefranc M-P, (1999) The Immunologist 7: 132-136 and Lefranc M-P et al., (1999) Nucleic Acids Res 27: 209-212. According to the IMGT numbering scheme, VH-CDR1 is at positions 26 to 35, VH-CDR2 is at positions 51 to 57, VH-CDR3 is at positions 93 to 102, VL-CDR1 is at positions 27 to 32, VL-CDR2 is at positions 50 to 52, and VL-CDR3 is at positions 89 to 97. In a particular embodiment, provided herein are antibodies and antigen-binding fragments thereof that comprise the IMGT VH and VL CDRs of the SAR114 and/or MEDI4893* antibodies, for example, as described in Lefranc M-P (1999) supra and Lefranc M-P et al., (1999) supra).

In certain aspects, the CDRs of an antibody or antigen-binding fragment thereof can be determined according to MacCallum R M et al., (1996) J Mol Biol 262: 732-745. See also, e.g., Martin A. "Protein Sequence and Structure Analysis of Antibody Variable Domains," in Antibody Engineering, Kontermann and Dtibel, eds., Chapter 31, pp. 422-439, Springer-Verlag, Berlin (2001). In a particular embodiment, provided herein are antibodies or antigen-binding fragments thereof comprise the VH and VL CDRs of the SAR114 and/or MEDI4893* antibodies determined by the method in MacCallum R M et al.

In certain aspects, the CDRs of an antibody or antigen-binding fragment thereof can be determined according to the AbM numbering scheme, which refers AbM hypervariable regions which represent a compromise between the Kabat CDRs and Chothia structural loops, and are used by Oxford Molecular's AbM antibody modeling software (Oxford Molecular Group, Inc.). In a particular embodiment, provided herein are antibodies or antigen-binding fragments that and comprise VH and VL CDRs of the SAR114 and/or MEDI4893* antibodies as determined by the AbM numbering scheme.

In another embodiment, the antibody or antigen-binding fragment thereof (e.g., monoclonal antibody or fragment) described herein may comprise a constant region (Fc) of any suitable class (IgG, IgA, IgD, IgM, and IgE) that has been modified in order to improve effector functions (e.g., opsonophagocytic bacterial killing (OPK)) or the half-life of the first and/or second antibody or antigen-binding fragment (e.g., monoclonal antibody or fragment) present in the composition. For example, the antibody or antigen-binding fragment thereof (e.g., monoclonal antibody or fragment) described herein may comprise an Fc that comprises a mutation that extends half-life relative to the same antibody without the mutation, and wherein the mutation does not inhibit OPK activity relative to the same antibody or antigen-binding fragment the mutation. Fc region engineering is widely used in the art to extend the half-life of therapeutic antibodies and protect from degradation in vivo. In some embodiments, the Fc region of an IgG antibody or antigen-binding fragment may be modified in order to increase the affinity of the IgG molecule for the Fc Receptor-neonate (FcRn), which mediates IgG catabolism and protects IgG molecules from degradation. The Fc region of any of the antibodies or antigen-binding fragments (e.g., monoclonal antibodies or fragments) described herein may comprise one or more amino acid substitutions or modifications which improve or extend antibody half-life or effector function, such as by increasing the affinity of an IgG molecule for the FcRn. Suitable Fc region amino acid substitutions or modifications are known in the art and include, for example, the triple substitution M252Y/S254T/T256E (referred to as "YTE") (see, e.g., U.S. Pat. No. 7,658,921; U.S. Patent Application Publication 2014/0302058; and Yu et al., *Antimicrob. Agents Chemother.*, 61(1): e01020-16 (2017)). In another embodiment, the Fc region may be derived from the high affinity FcRn-binding Fc variant N3E-YTE (see, e.g., Borrok et al., *J. Biol. Chem.*, 290(7): 4282-4290 (2015)), which comprises the YTE mutation in $C_H2$ and cysteine residues at positions 432 and 437. For example, the N3E-YTE variant may lack the YTE mutation (referred to as "N3E"), or may be substituted at Fc residue 432 (using Kabat numbering) with, for example, the sequence CSWHLC (referred to as "N3"; SEQ ID NO:19), CSFHLC (referred to as "N3F"; SEQ ID NO:20), or CSYHLC (referred to as "N3Y"; SEQ ID NO:21). The N3, N3F, and N3Y Fc variants, in particular, exhibit enhanced pharmacokinetic (PK) properties (e.g., serum persistence) and effector functions (e.g., opsonophagocytic bacterial killing (OPK)) as compared to the YTE variants.

Sequences of exemplary Fc variants are provided below.

binding fragment and the AT-binding antibody or antigen-binding fragment described above. Indeed, the present disclosure also separately provides a antibody or antigen-binding fragment thereof (e.g., a monoclonal antibody or fragment) comprising: (a) a heavy chain polypeptide comprising a CDR1 amino acid sequence of SEQ ID NO: 1, a CDR2 amino acid sequence of SEQ ID NO: 2, and a CDR3 amino acid sequence of SEQ ID NO: 3, and (b) a light chain polypeptide comprising a CDR1 amino acid sequence of SEQ ID NO: 4, a CDR2 amino acid sequence of SEQ ID NO: 5, and a CDR3 amino acid sequence of SEQ ID NO: 6.

The disclosure also provides a bispecific antibody or antigen-binding fragment that binds (e.g., simultaneously) both ClfA and AT. The term "bispecific monoclonal antibody" (also referred to as a "dual-specific" monoclonal antibody) refers to a monoclonal antibody that comprises two different antigen-recognition domains and therefore can simultaneously bind two different epitopes. Monoclonal antibodies that recognize and bind to more than two different epitopes are referred to in the art as "multi-specific monoclonal antibodies." The first bispecific antibodies were generated by somatic hybridization of two antibody-secreting cells, but produced poor yields due to random assembly of

| Fc Variant | Sequence (SEQ ID NO) |
| --- | --- |
| N3 (also referred to as N3W) | CSWHLC (SEQ ID NO: 19) |
| N3F | CSFHLC (SEQ ID NO: 20) |
| N3Y | CSYHLC (SEQ ID NO: 21) |
| N3 Fc starting from hinge | CPPCPAPELLGGPSVFLFPPKPKDTLMISRTPEVTCVVVDVSHEDPEV KFNWYVDGVEVHNAKTKPREEQYNSTYRVVSVLTVLHQDWLNGK EYKCKVSNKALPAPIEKTISKAKGQPREPQVYTLPPSREEMTKNQVS LTCLVKGFYPSDIAVEWESNGQPENNYKTTPPVLDSDGSFFLYSKLT VDKSRWQQGNVFSCSVMHEACSWHLCQKSLSLSPGK (SEQ ID NO: 29) |
| N3Y Fc starting from hinge | CPPCPAPELLGGPSVFLFPPKPKDTLMISRTPEVTCVVVDVSHEDPEV KFNWYVDGVEVHNAKTKPREEQYNSTYRVVSVLTVLHQDWLNGK EYKCKVSNKALPAPIEKTISKAKGQPREPQVYTLPPSREEMTKNQVS LTCLVKGFYPSDIAVEWESNGQPENNYKTTPPVLDSDGSFFLYSKLT VDKSRWQQGNVFSCSVMHEACSYHLCQKSLSLSPGK (SEQ ID NO: 24) |

The present disclosure provides antibodies and antigen-binding fragments thereof that bind to ClfA (e.g., antibodies and antigen-binding fragments comprising the CDR, VH and/or VL, heavy and or light, or Fc variant sequences listed in the tables above) and have IC50's for ClfA001, ClfA002, and ClfA004 in a fibrinogen binding inhibition assay that are within 2 μg/ml of each other. For example, the $IC_{50}$'s of the antibody or antigen-binding fragment thereof for ClfA001, ClfA002, and ClfA004 can all be between 1 μg/ml and 5 μg/ml. The binding affinities ($K_D$) of the antibody or antigen-binding fragment thereof for ClfA001, ClfA002, and ClfA004 can all be all between 200 and 350 pM.

The present disclosure provides antibodies and antigen-binding fragments thereof that bind to ClfA (e.g., antibodies and antigen-binding fragments comprising the CDR, VH and/or VL, heavy and or light, or Fc variant sequences listed in the tables above) and have a monomeric purity that decreases by no more than 5% after exposure to conventional white light at 2 kLux/hr at 23° C. for 14 days.

The present disclosure is not limited to a composition comprising both the ClfA-binding antibody or antigen-parental heavy and light chains (Milstein, C. and A. C. Cuello, *Immunol. Today*, 5: 299-304 (1984)). The discovery of single chain variable fragments (scFvs) and advances in antibody engineering have resulted in new methodologies for the development of bispecific antibodies (Orcutt et al., *Protein Eng. Des. Sel.*, 23: 221-228 (2010); and Coloma, M. J. and S. L. Morrison, *Nat. Biotechnol.*, 15: 159-163 (1997)). There are now at least 50 different bispecific antibody formats based on scFv numbers and fusion positions on the IgG scaffold (Kontermann, R. E., *MAbs*, 4: 182-197 (2012)). Bispecific and multispecific antibodies may be manufactured in several different structural formats, including, but not limited to, tandem scFv, diabodies, tandem diabodies, dual variable domain antibodies and heterodimerization using a motif such as CH1/Ck domain or the Dock and Lock motif (see, e.g., Chames, P. and D. Baty, *Curr. Opin. Drug. Discov. Devel.*, 12: 276-283 (2009)). In one embodiment, the disclosure provides an antibody or antigen-binding fragment thereof (e.g., a monoclonal antibody or fragment) which specifically binds to a *Staphylococcus aureus* ClfA protein and a *Staphylococcus aureus* alpha toxin (AT) protein (i.e., a bispecific antibody), which comprises: (a) a first heavy chain polypeptide comprising a CDR1 amino acid sequence of SEQ ID NO: 1, a CDR2 amino acid sequence of SEQ ID NO: 2, and a CDR3 amino acid sequence of SEQ ID NO: 3, (b) a first light chain polypeptide comprising a CDR1 amino acid sequence of SEQ ID NO: 4, a CDR2 amino acid sequence of SEQ ID NO: 5, and a CDR3 amino acid sequence of SEQ ID NO: 6, (c) a second heavy chain polypeptide comprising a CDR1 amino acid sequence of SEQ ID NO: 7, a CDR2 amino acid sequence of SEQ ID NO: 8, and a CDR3 amino acid sequence of SEQ ID NO: 9, and (d) a second light chain polypeptide comprising a CDR1 amino acid sequence of SEQ ID NO: 10, a CDR2 amino acid sequence of SEQ ID NO: 11, and a CDR3 amino acid sequence of SEQ ID NO: 12. In another embodiment, the first heavy chain polypeptide and the first light chain polypeptide of the aforementioned bispecific antibody or antigen-binding fragment thereof (e.g., monoclonal antibody or fragment) comprises variable region amino acid sequences of SEQ ID NO: 13 and SEQ ID NO: 14, respectively, and the second heavy chain polypeptide and the second light chain polypeptide of the aforementioned bispecific antibody or antigen-binding fragment thereof (e.g., monoclonal antibody or fragment) comprises variable region amino acid sequences of SEQ ID NO: 15 and SEQ ID NO: 16, respectively. Such bispecific (optionally monoclonal) antibodies (antibodies comprising SAR114 and MEDI4893 or MEDI4893* sequences) can have decreased AT-neutralization activity as compared to the AT-neutralization activity of MEDI4893 or MEDI4893* e.g., as a result of SAR114's strong binding to ClfA. This is in contrast to other bispecific (optionally monoclonal) antibodies that bind to *Staphylococcus aureus* ClfA and AT proteins (e.g., antibodies comprising 11H10 and MEDI4893 or MEDI4893* sequences) that do not have significantly decreased AT-neutralization activity as compared to the AT-neutralization activity of MEDI4893 or MEDI4893*. Methods for generating bispecific or multi-specific (optionally monoclonal) antibodies are known in the art and described in, for example, Holliger et al., *Proc. Natl. Acad. Sci. USA,* 90(14): 6444-6448 (1993); Brinkmann, U. and R. E. Kontermann, *MAbs,* 9(2): 182-212 (2017); and Segal, D. M. and Bast, B. J. 2001. Production of Bispecific Antibodies. *Current Protocols in Immunology.* 14:IV:2.13:2.13.1-2.13.16)

The antibody or antigen-binding fragment (e.g. monoclonal antibody or fragment) described herein may be, or may be obtained from, a human antibody, a humanized antibody, a non-human antibody, or a chimeric antibody. A "chimeric" antibody refers to an antibody or fragment thereof comprising both human and non-human regions. A "humanized" antibody is a antibody comprising a human antibody scaffold and at least one CDR obtained or derived from a non-human antibody. Non-human antibodies include antibodies isolated from any non-human animal, such as, for example, a rodent (e.g., a mouse or rat). A humanized antibody can comprise, one, two, or three CDRs obtained or derived from a non-human antibody. A fully human antibody does not contain any amino acid residues obtained or derived from a non-human animal. It will be appreciated that fully human and humanized antibodies carry a lower risk for inducing immune responses in humans than mouse or chimeric antibodies (see, e.g., Harding et al., *mAbs,* 2(3): 256-26 (2010)). In one embodiment, the antibody described herein, or antigen-binding fragment thereof, is a fully human antibody.

A human antibody, a non-human antibody, a chimeric antibody, or a humanized antibody can be obtained by any means, including via in vitro sources (e.g., a hybridoma or a cell line producing an antibody recombinantly) and in vivo sources (e.g., rodents, human tonsils). Methods for generating antibodies are known in the art and are described in, for example, Köhler and Milstein, *Eur. J. Immunol.,* 5: 511-519 (1976); Harlow and Lane (eds.), *Antibodies: A Laboratory Manual*, CSH Press (1988); and Janeway et al. (eds.), *Immunobiology, 5th Ed*., Garland Publishing, New York, N.Y. (2001)). In certain embodiments, a human antibody or a chimeric antibody can be generated using a transgenic animal (e.g., a mouse) wherein one or more endogenous immunoglobulin genes are replaced with one or more human immunoglobulin genes. Examples of transgenic mice wherein endogenous antibody genes are effectively replaced with human antibody genes include, but are not limited to, the Medarex HUMAB-MOUSE™, the Kirin TC MOUSE™, and the Kyowa Kirin KM-MOUSE™ (see, e.g., Lonberg, *Nat. Biotechnol.,* 23(9): 1117-25 (2005), and Lonberg, *Handb. Exp. Pharmacol.,* 181: 69-97 (2008)). A humanized antibody can be generated using any suitable method known in the art (see, e.g., An, Z. (ed.), *Therapeutic Monoclonal Antibodies: From Bench to Clinic*, John Wiley & Sons, Inc., Hoboken, N.J. (2009)), including, e.g., grafting of non-human CDRs onto a human antibody scaffold (see, e.g., Kashmiri et al., *Methods,* 36(1): 25-34 (2005); and Hou et al., *J. Biochem.,* 144(1): 115-120 (2008)). In one embodiment, a humanized antibody can be produced using the methods described in, e.g., U.S. Patent Application Publication 2011/0287485 A1.

The disclosure also provides one or more isolated nucleic acid sequences that encode the ClfA-binding antibody, the AT-binding antibody, or the antibody that binds both ClfA and AT as described herein, or an antigen-binding fragment thereof (optionally wherein the antibody or fragment is monoclonal). The term "nucleic acid sequence" is intended to encompass a polymer of DNA or RNA, i.e., a polynucleotide, which can be single-stranded or double-stranded and which can contain non-natural or altered nucleotides. The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to, methylated and/or capped polynucleotides. Nucleic acids are typically linked via phosphate bonds to form nucleic acid sequences or polynucleotides, though many other linkages are known in the art (e.g., phosphorothioates, boranophosphates, and the like).

The disclosure further provides one or more vectors comprising one or more nucleic acid sequences encoding the ClfA-binding antibody, the AT-binding antibody, or the antibody that binds both ClfA and AT as described herein, or an antigen-binding fragment thereof (optionally wherein the antibody or fragment is monoclonal). The vector can be, for example, a plasmid, episome, cosmid, viral vector (e.g., retroviral or adenoviral), or phage. Suitable vectors and methods of vector preparation are well known in the art (see, e.g., Sambrook et al., *Molecular Cloning, a Laboratory Manual,* 3*rd edition*, Cold Spring Harbor Press, Cold Spring Harbor, N.Y. (2001), and Ausubel et al., *Current Protocols in Molecular Biology*, Greene Publishing Associates and John Wiley & Sons, New York, N.Y. (1994)).

In addition to the nucleic acid sequence encoding the ClfA-binding antibody or antigen-binding fragment, the AT-binding antibody or antigen-binding fragment, or the antibody or antigen-binding fragment that binds both ClfA and AT as described herein (optionally wherein the antibody or fragment is monoclonal), the vector desirably comprises expression control sequences, such as promoters, enhancers, polyadenylation signals, transcription terminators, internal ribosome entry sites (IRES), and the like, that provide for the expression of the coding sequence in a host cell. Exemplary expression control sequences are known in the art and described in, for example, Goeddel, *Gene Expression Technology: Methods in Enzymology*, Vol. 185, Academic Press, San Diego, Calif. (1990).

The vector(s) comprising the nucleic acid(s) encoding the amino acid sequence(s) of the antibodies or antigen-binding fragments described herein (e.g., an amino acid sequence encoding the heavy chain and/or the light chain of a ClfA-binding antibody) (optionally a monoclonal antibody or fragment) can be introduced into a host cell that is capable of expressing the polypeptides encoded thereby, including any suitable prokaryotic or eukaryotic cell. As such, the present disclosure provides an isolated cell comprising the vector. Host cells that may be used include those that can be easily and reliably grown, have reasonably fast growth rates, have well characterized expression systems, and can be transformed or transfected easily and efficiently. Examples of suitable prokaryotic cells include, but are not limited to, cells from the genera *Bacillus* (such as *Bacillus subtilis* and *Bacillus brevis*), *Escherichia* (such as *E. coli*), *Pseudomonas, Streptomyces, Salmonella*, and *Erwinia*. Particularly useful prokaryotic cells include the various strains of *Escherichia coli* (e.g., K12, HB101 (ATCC No. 33694), DH5a, DH10, MC1061 (ATCC No. 53338), and CC102). Suitable eukaryotic cells are known in the art and include, for example, yeast cells, insect cells, and mammalian cells. In one embodiment, the vector is expressed in mammalian cells. A number of suitable mammalian host cells are known in the art, and many are available from the American Type Culture Collection (ATCC, Manassas, Va.). Examples of suitable mammalian cells include, but are not limited to, Chinese hamster ovary cells (CHO) (ATCC No. CCL61), CHO DHFR− cells (Urlaub et al, *Proc. Natl. Acad. Sci. USA*, 97: 4216-4220 (1980)), human embryonic kidney (HEK) 293 or 293T cells (ATCC No. CRL1573), and 3T3 cells (ATCC No. CCL92). Other suitable mammalian cell lines are the monkey COS-1 (ATCC No. CRL1650) and COS-7 cell lines (ATCC No. CRL1651), as well as the CV-1 cell line (ATCC No. CCL70). The mammalian cell desirably is a human cell. For example, the mammalian cell can be a human lymphoid or lymphoid derived cell line, such as a cell line of pre-B lymphocyte origin, a PER.C6® cell line (Crucell Holland B.V., The Netherlands), or human embryonic kidney (HEK) 293 or 293T cells (ATCC No. CRL1573).

A nucleic acid sequence encoding amino acids of any of the antibodies or antigen-binding fragments (optionally monoclonal antibodies or fragments) described herein may be introduced into a cell by "transfection," "transformation," or "transduction." "Transfection," "transformation," or "transduction," as used herein, refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.), *Methods in Molecular Biology*, Vol. 7, *Gene Transfer and Expression Protocols*, Humana Press (1991)); DEAE-dextran; electroporation; cationic liposome-mediated transfection; tungsten particle-facilitated microparticle bombardment (Johnston, *Nature*, 346: 776-777 (1990)); and strontium phosphate DNA co-precipitation (Brash et al, *Mol. Cell Biol.*, 7: 2031-2034 (1987)). Phage or viral vectors can be introduced into host cells, after growth of infectious particles in suitable packaging cells, many of which are commercially available.

The present disclosure provides a composition comprising an effective amount of any one or combination of the antibodies or antigen-binding fragments thereof described herein and a pharmaceutically acceptable carrier. In one embodiment, for example, the composition may comprise a first antibody or antigen-binding fragment thereof (optionally monoclonal) that specifically binds to *S. aureus* ClfA protein, as described above, and a second antibody or antigen-binding fragment thereof (optionally monoclonal) that specifically binds to *S. aureus* AT protein, as described above, and a pharmaceutically acceptable carrier. Alternatively, the composition may comprise either a antibody or antigen-binding fragment thereof that specifically binds to *S. aureus* ClfA protein, or a antibody or antigen-binding fragment thereof that specifically binds to *S. aureus* AT protein and a pharmaceutically acceptable carrier. In yet another embodiment, the composition may comprise the nucleic acid sequences encoding the ClfA-binding antibody or antigen-binding fragment, the AT-binding antibody or antigen-binding fragment, and/or the anti-ClfA/AT bispecific antibody or antigen-binding fragment, or one or more vectors comprising such nucleic acid sequences. In one embodiment, the composition is a pharmaceutically acceptable (e.g., physiologically acceptable) composition, which comprises a carrier, such as a pharmaceutically acceptable (e.g., physiologically acceptable) carrier, and the ClfA-binding antibody or antigen-binding fragment, the AT-binding antibody or antigen-binding fragment, the anti-ClfA/AT bispecific antibody or antigen-binding fragment, nucleic acid sequence(s), or vector(s). Any suitable carrier can be used within the context of the disclosure, and such carriers are well known in the art. The choice of carrier will be determined, in part, by the particular site to which the composition may be administered and the particular method used to administer the composition. The composition optionally can be sterile. The composition can be frozen or lyophilized for storage and reconstituted in a suitable sterile carrier prior to use. The compositions can be generated in accordance with conventional techniques described in, e.g., *Remington: The Science and Practice of Pharmacy*, 21st Edition, Lippincott Williams & Wilkins, Philadelphia, Pa. (2001).

The composition desirably comprises the ClfA-binding antibody and/or the AT-binding antibody, and/or the anti-ClfA/AT bispecific antibody, or antigen-binding fragments thereof (e.g., monoclonal antibody or fragment), in an amount that is effective to treat or prevent a *S. aureus* infection. Thus, the disclosure provides a method of treating or preventing a *Staphylococcus aureus* (*S. aureus*) infection in a subject (e.g., a human), which comprises administering the composition comprising any one or combination of the antibodies or antigen-binding fragments thereof (e.g. monoclonal antibodies or fragments) described herein to a subject in need thereof, whereupon the *S. aureus* infection is treated or prevented in the subject. The disclosure also provides use of the ClfA-binding antibody or antigen-binding fragment, the AT-binding antibody or antigen-binding fragment, and/or the anti-ClfA/AT bispecific antibody or antigen-binding fragment described herein, or the composition comprising any one or combination of the antibodies or fragments thereof described herein, in the manufacture of a medicament for treating or preventing a *S. aureus* infection. As discussed herein, *Staphylococcus aureus* is a major human pathogen that causes a wide range of clinical infections. *S. aureus* is a leading cause of bacteremia and infective endocarditis as well as osteoarticular, skin and soft tissue, pleuropulmonary, and device-related infections. Approximately 30% of the human population is colonized with *S. aureus* (Wertheim et al., *Lancet Infect. Dis.*, 5: 751-762 (2005)). The symptoms of *S. aureus* skin infections include, for example, boils, cellulits, and impetigo. *S. aureus* also may cause food poisoning, blood poisoning (also known as bacteremia), toxic shock syndrome, and septic arthritis. The epidemiology, pathophysiology, and clinical manifestations of *S. aureus* infections are described in detail in, e.g., Tong et al., *Clin. Microbiol. Rev.*, 28(3): 603-661 (2015), and the genomes of several different *S. aureus* strains have been sequenced (see, e.g., GenBank/EMBL Accession Nos. BX571856, BX571857, BX571858, FN433596, FN433597, FN433598, HE681097, FR821777, FR821778, FR821779, and FR821780). As discussed herein, the subject (e.g., human subject) can have diabetes.

As used herein, the terms "treatment," "treating," and the like, refer to obtaining a desired pharmacologic and/or physiologic effect. In one embodiment, the effect is therapeutic, i.e., the effect partially or completely cures a disease and/or adverse symptom attributable to the disease. To this end, the disclosed method comprises administering a "therapeutically effective amount" of the ClfA-binding antibody, the AT-binding antibody, and/or the anti-ClfA/AT bispecific antibody, or antigen-binding fragments thereof, or the composition comprising any one or combination of the aforementioned antibodies or fragments (including monoclonal antibodies or fragments). A "therapeutically effective amount" refers to an amount effective, at dosages and for periods of time necessary, to achieve a desired therapeutic result. The therapeutically effective amount may vary according to factors such as the disease state, age, sex, and weight of the individual, and the ability of the antibody or antigen-binding fragment to elicit a desired response in the individual. For example, a therapeutically effective amount of a ClfA-binding antibody or antigen-binding fragment thereof, an AT-binding antibody or antigen-binding fragment thereof, or a ClfA/AT bispecific antibody or antigen-binding fragment thereof is an amount which inhibits *S. aureus*-associated sepsis, inhibits *S. aureus* agglutination, inhibits thromboembolic lesion formation, neutralizes alpha toxin, induces opsonophagocytosis, inhibits *S. aureus* fibrinogen binding, inhibits *S. aureus* agglutination, or any combination of the foregoing, in a human.

Alternatively, the pharmacologic and/or physiologic effect may be prophylactic, i.e., the effect completely or partially prevents a disease or symptom thereof. In this respect, the disclosed method comprises administering a "prophylactically effective amount" of the ClfA-binding antibody, the AT-binding antibody, and/or the anti-ClfA/AT bispecific antibody, or antigen-binding fragments thereof (including monoclonal antibodies or fragments). A "prophylactically effective amount" refers to an amount effective, at dosages and for periods of time necessary, to achieve a desired prophylactic result (e.g., prevention of *S. aureus* infection or disease onset).

Therapeutic or prophylactic efficacy can be monitored by periodic assessment of treated patients. For repeated administrations over several days or longer, depending on the condition, the treatment can be repeated until a desired suppression of disease symptoms occurs. However, other dosage regimens may be useful and are within the scope of the present disclosure. The desired dosage can be delivered by a single bolus administration of the composition, by multiple bolus administrations of the composition, or by continuous infusion administration of the composition.

The method of treating or preventing a *S. aureus* infection may comprise administering the ClfA-binding antibody described herein, the AT-binding described herein, both the ClfA-binding and AT-binding antibodies described herein, or the ClfA-AT bispecific antibody described herein, or antigen-binding fragments thereof. In embodiments where both the ClfA-binding and AT-binding antibodies or fragments (e.g., monoclonal antibodies or fragments) are administered to a subject, each antibody or fragment may be present in the same composition or in separate compositions. When separate compositions are administered to the subject, each of the compositions can be administered simultaneously or sequentially in any order.

The composition(s) comprising an effective amount of any one or combination of the antibodies described herein, or antigen-binding fragments thereof, the nucleic acid sequence(s) encoding any of the foregoing, or the vector comprising the nucleic acid sequence may be administered to a subject, such as a human, using standard administration techniques, including intravenous, intraperitoneal, subcutaneous, and intramuscular administration routes. The composition may be suitable for parenteral administration. The term "parenteral," as used herein, includes intravenous, intramuscular, subcutaneous, and intraperitoneal administration. In some embodiments, the composition is administered to a subject using peripheral systemic delivery by intravenous, intraperitoneal, or subcutaneous injection.

The ClfA-binding antibody or antigen-binding fragment, the AT-binding antibody or antigen-binding fragment, the and/or the anti-ClfA/AT bispecific antibody or antigen-binding fragment, or composition(s) comprising same, may be administered alone or in combination with other drugs (e.g., as an adjuvant) conventionally used for treating *S. aureus* infections. The composition(s) comprising the ClfA-binding antibody or antigen-binding fragment, the AT-binding antibody or antigen-binding fragment, or the ClfA-AT bispecific antibody or antigen-binding fragment may be used in combination with, for example, one or more antibiotics, such as a penicillinase-resistant β-lactam antibiotic (e.g., oxacillin or flucloxacillin). Gentamicin may be used to treat serious infections, such as endocarditis. Most strains of *S. aureus*, however, are now resistant to penicillin, and two in 100 people carry methicillin-resistant strains of *S. aureus* (MRSA). MRSA infections typically are treated with vancomycin, and minor skin infections may be treated with triple antibiotic ointment.

In addition to therapeutic uses, any one or combination of the antibodies described herein can be used in diagnostic or research applications. In this respect, the ClfA-binding antibody or antigen-binding fragment, the AT-binding antibody or antigen-binding fragment, or the ClfA-AT bispecific antibody or antigen-binding fragment may be used in an assay to monitor *S. aureus* infection in a subject. Research applications include, for example, methods that utilize the ClfA-binding antibody or antigen-binding fragment, the AT-binding antibody or antigen-binding fragment, or the ClfA-AT bispecific antibody or antigen-binding fragment and a label to detect *S. aureus* in a sample, e.g., in a human body fluid or in a cell or tissue extract. The ClfA-binding antibody or antigen-binding fragment, the AT-binding antibody or antigen-binding fragment, or the ClfA-AT bispecific antibody or antigen-binding fragment may be used with or without modification, such as covalent or non-covalent labeling with a detectable moiety. For example, the detectable moiety can be a radioisotope (e.g., $^3$H, $^{14}$C, $^{32}$P, $^{35}$S, or $^{125}$I), a fluorescent or chemiluminescent compound (e.g., fluorescein isothiocyanate, rhodamine, or luciferin), an enzyme (e.g., alkaline phosphatase, beta-galactosidase, or horseradish peroxidase), or prosthetic groups. Any method known in the art for separately conjugating an antibody or antigen-binding fragment thereof to a detectable moiety may be employed in the context of the present disclosure (see, e.g., Hunter et al., Nature, 194: 495-496 (1962); David et al., Biochemistry, 13: 1014-1021 (1974); Pain et al., J. Immunol. Meth., 40: 219-230 (1981); and Nygren, J., Histochem. And Cytochem., 30: 407-412 (1982)).

Any one or combination of the antibodies described herein, or antigen-binding fragments thereof (e.g., monoclonal antibodies or fragments), the nucleic acid sequence(s) encoding any of the foregoing, the vector(s) comprising the nucleic acid sequence(s), or the composition(s) comprising any of the foregoing, can be provided in a kit, i.e., a packaged combination of reagents in predetermined amounts with instructions for performing a diagnostic assay. If the ClfA-binding antibody or antigen-binding fragment, the AT-binding antibody or antigen-binding fragment, or the ClfA-AT bispecific antibody or antigen-binding fragment is labeled with an enzyme, the kit desirably includes substrates and cofactors required by the enzyme (e.g., a substrate precursor which provides a detectable chromophore or fluorophore). In addition, other additives may be included in the kit, such as stabilizers, buffers (e.g., a blocking buffer or lysis buffer), and the like. The relative amounts of the various reagents can be varied to provide for concentrations in solution of the reagents which substantially optimize the sensitivity of the assay. The reagents may be provided as dry powders (typically lyophilized), including excipients which on dissolution will provide a reagent solution having the appropriate concentration.

The following examples further illustrate the invention but, of course, should not be construed as in any way limiting its scope.

Example 1

This example demonstrates the selection and characterization of a monoclonal antibody that specifically binds to *S. aureus* ClfA protein.

Enhanced protective capacity and isolate coverage afforded by prophylaxis with an anti-*S. aureus* alpha toxin (AT) monoclonal antibody (mAb) (referred to as "MEDI4893*") described in International Patent Application Publications WO 2012/109285 and WO 2014/074540 as "LC10") in combination with an anti-ClfA mAb (referred to as "11H10") relative to the individual mAbs in a *S. aureus* lethal bacteremia model has been previously reported (Tkaczyk et al., MBio., 7(3). pii: e00528-16 (2016)). (Note that MEDI4893, which contains a YTE mutation not present in MEDI4893* was not used in mice because, although the YTE mutation increases IgG half-life in humans, it reduces serum exposure in mice.) Although 11H10 showed potent anti-ClfA activity, it exhibited a greater than 1000-fold reduced affinity ($K_{on}$ was below limit of detection, ND in Table 1) and about a 40-fold increase in $IC_{50}$ for the ClfA founder sequence ClfA002 in a fibrinogen binding inhibition assay relative to the other ClfA founder sequences ClfA001 and ClfA004, as shown in FIG. 1A and Table 1. ClfA002 is expressed by a prominent *S. aureus* hospital acquired MRSA (HA-MRSA; USA100 or sequence type 5 (ST5)) (Sharma-Kuinkel et al., J. Clin. Microbiol., 53: 227-236 (2015); and Mendes et al., J. Clin. Microbiol., 50: 3694-3702 (2012)).

TABLE 1

Anti-ClfA mAbs: Correlation between affinity and in vitro activity

| | | Kon ($M^{-1}s^{-1}$) | Affinity Koff ($s^{-1}$) | Kd | CHI$^2$ | Fibrinogen binding IC$_{50}$ (µg/ml) |
|---|---|---|---|---|---|---|
| SAR114 | ClfA001 | 2.41E+06 | 6.01E-06 | 2.493 pM | 0.206 | 1.166 |
| | ClfA002 | 2.13E+06 | 9.53E-05 | 44.77 pM | 0.383 | 1.161 |
| | ClfA004 | 5.62E+06 | 6.46E-06 | 1.15 pM | 0.330 | 1.627 |
| 11H10 | ClfA001 | 1.092E+06 | 6.80E-03 | 6.22 nM | 0.214 | 0.881 |
| | ClfA002 | | | 27.6 µM | | 9.772 |
| | ClfA004 | 8.457E+5 | 6.390E-3 | 7.555 nM | 0.502 | 0.662 |

To increase potential clinical isolate coverage, a human tonsillar B-cell library was screened to search for more broadly reactive anti-ClfA mAbs. Specifically, memory B cells were isolated from cryopreserved lymphocytes isolated from tonsils using phycoerythrin (PE)-Cy7-labelled CD19 microbeads (BD Biosciences, San Jose, Calif.), followed by staining with anti-PE-beads (Miltenyi Biotec, Inc., San Diego, Calif.), and by depletion of cells carrying IgM, IgD, and IgA by cell sorting on a FACSAria (BD Biosciences, San Jose, Calif.). Cells were immortalized under clonal condition with Epstein Barr Virus (EBV) as described in Traggiai et al., Nat. Med., 10: 871-875 (2004). After two weeks, the culture supernatants were screened for the presence of ClfA001-specific monoclonal antibodies using a 384-well based ELISA assay. Briefly, serial dilutions (1:2 or 1:600) of the anti-ClfA mAbs were added to ClfA coated plates, followed by addition of biotinylated 11H10 (1:600). Percent competition was calculated as 100* ($OD_{mAb+11H10biot}$)/($OD_{11H10biot}$)). Positive cultures were expanded in complete RPMI medium and selected for their ability to bind to ClfA genotypes 001, 002, and 004 with high affinity. The VH and VL sequences were retrieved by RT-PCR.

Figure 4:
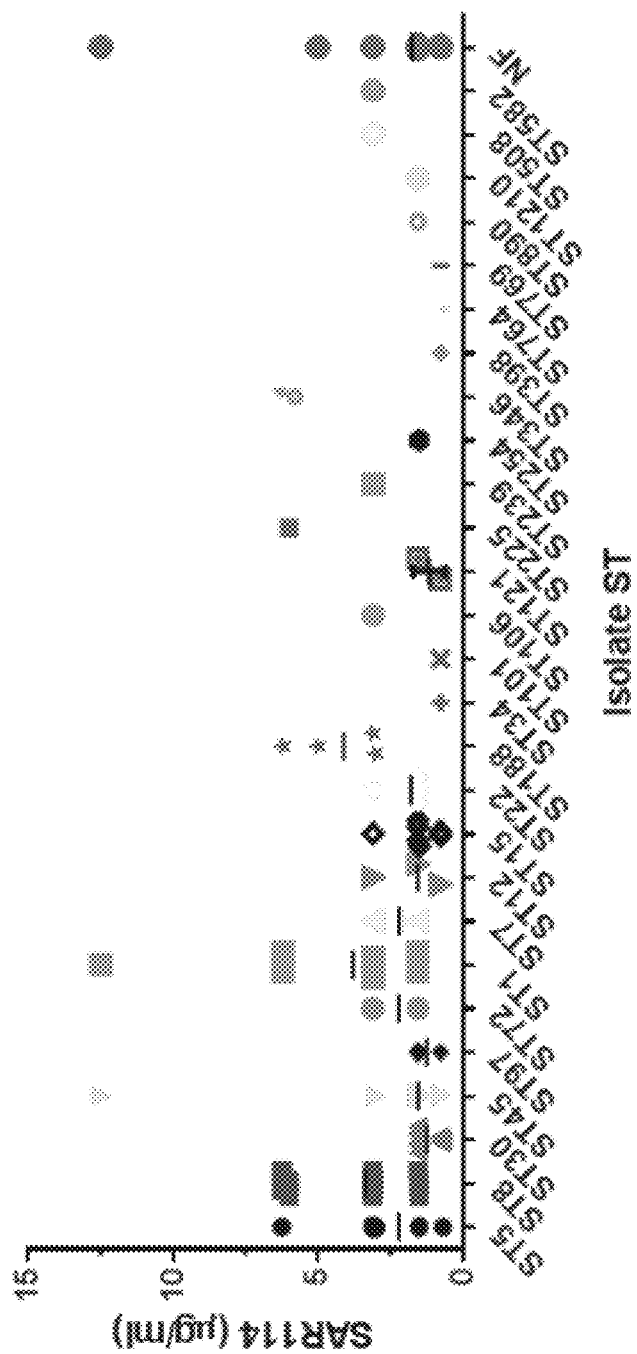

From this effort, a monoclonal antibody was identified (referred to as "SAR114") that exhibited high affinity for ClfA001, 002, and 004 (KD=1.15-44.7 pM, Table 1) and potent inhibition of fibrinogen binding by the three prominent founder ClfA genotypes ($IC_{50}$~20 µM), as shown in FIG. 1B. SAR114 also exhibited opsonophagocytic killing (OPK) activity against several *S. aureus* clinical isolates, as shown in FIGS. 3A-3F (see, e.g., Tkaczyk et al., supra for methods of measuring OPK killing) and improved inhibition of bacterial agglutination in human plasma compared to 11H10, as shown in FIG. 2, FIG. 4, and Table 2, below). Agglutination inhibition in human plasma was measured by culturing 112 *S. aureus* clinical isolates overnight in tryptic soy broth (TSB), washing in PBS, and suspending to one tenth of the original volume in ice-cold PBS. Anti-ClfA monoclonal antibodies were serially diluted (two-fold) in 30 µl PBS starting at 200 µg/ml and mixed with 30 µl of citrated human plasma in a 96-well U bottom plate (ThermoFisher Scientific, Waltham, Mass.). Bacteria were added (30 µl) and incubated for 5 minutes at 37° C. Each well was evaluated visually, and the lowest monoclonal antibody concentration where bacteria agglutinated was recorded. R347, a human anti-gp120 monoclonal antibody was utilized as an isotype control human IgG1 (c-IgG). Human negative control monoclonal antibody (c-IgG) did not show any inhibitory effect up to 200 µg/ml.

TABLE 2

Minimal concentration of SAR114 required
to inhibit bacterial agglutination.

| Strain | CC | µg/ml | Strain | CC | µg/ml |
|---|---|---|---|---|---|
| 2784 | 1 | 3 | NRS383 | 8 | 1.5 |
| 801 | 5 | 3 | 3691 | 8 | 0.7 |
| 4211 | 5 | 1.5 | 3406 | 8 | 25 |
| ARC634 | 5 | 1.5 | 3691 | 8 | 3 |
| ARC635 | 5 | 0.7 | 3527 | 8 | 6 |
| ARC797 | 5 | 6 | ARC2081 | 30 | 0.7 |
| NRS382 | 5 | 3 | NRS383 | 30 | 6 |
| 9105 | 5 | 1.5 | UAMS-1 | 30 | 1.5 |
| 9057 | 8 | 6 | 484 | 30 | 0.35 |
| ARC2464 | 8 | 3 | 9048 | 45 | 3 |
| BAA1556 | 8 | 6 | NRS22 | 45 | 1.5 |
| NRS384 | 8 | 6 | 9112 | 45 | 1.5 |

Data are representative of three independent experiments with the same donor as a plasma source.

Figure 5:
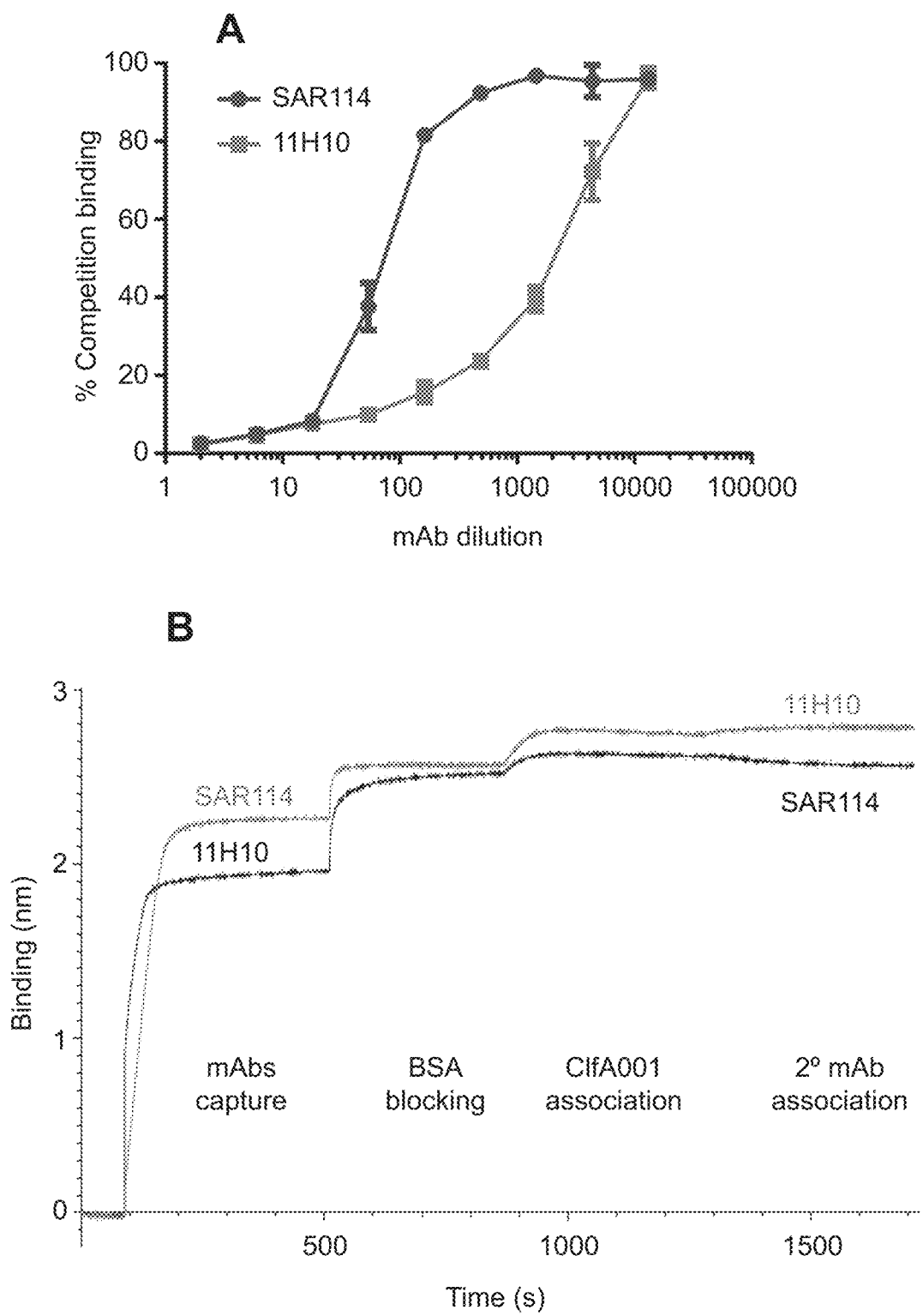

The heavy chain polypeptide of the SAR114 antibody was determined to comprise a variable region amino acid sequence of SEQ ID NO: 13, with a CDR1 amino acid sequence of SEQ ID NO: 1, a CDR2 amino acid sequence of SEQ ID NO: 2, and a CDR3 amino acid sequence of SEQ ID NO: 3. The light chain polypeptide of the SAR114 antibody was determined to comprise a variable region amino acid sequence of SEQ ID NO: 14, with a CDR1 amino acid sequence of SEQ ID NO: 4, a CDR2 amino acid sequence of SEQ ID NO: 5, and a CDR3 amino acid sequence of SEQ ID NO: 6. 11H10 and SAR114 were found to compete for binding to ClfA001 by ELISA and in an Octet-based competition assay, as shown in FIGS. 5A and 5B. Briefly, mAbs diluted at 5 µg/ml in PBS were captured on a aminopropylsilane (APS) biosensors for 7 min. Coated biosensors were moved into blocking buffer-containing wells (PBS, 1 mg/ml BSA (Sigma Aldrich, St. Louis, Mo.)) for 6 minutes to block free sensor binding sites, incubated for 7 minutes with 2.5 µg/ml ClfA001 diluted in blocking buffer, and finally moved into wells containing the competing mAbs diluted at 5 µg/ml in blocking buffer. Data were analyzed using the OCTET® Data Acquisition and Analysis Software (Pall ForteBio LLC, Fremont, Calif.). Absence of association of the competing mAb resulted in competition, and thus recognition of the same antigenic site, while non-competition was observed when association of the second mAb was detected.

The results of this example indicate that the anti-ClfA monoclonal antibodies 11H10 and SAR114 bind an overlapping epitope on ClfA001, which suggests that their difference in activity against ClfA002 may result from different binding affinities.

Example 2

This example describes the generation of SAR114-N3, which has an increased half-life as compared to SAR114.

It is well known that Fc regions of antibodies play a role in their half-life, and Fc engineering has been used to manipulate the half-life of therapeutic biologics. For example, a triple amino acid substitution M252Y/S254T/T256E (called the "YTE" substitution), has been engineered into the Fc regions of antibodies, including the anti-S. aureus MEDI4893 antibody, and it can lead to a 3-4 fold increase in half-life. However, the YTE mutation has also been shown to result in decreased binding to C1q and FcγRs and to reduce effector functions such as ADCC and CDC activity. (Monnet C., et al., Front Immunol. 6: 39 (2015).) The YTE mutation also reduces opsonophagocytic killing (OPK) of anti-bacterial antibodies. (See FIG. 6 showing that the YTE substitution reduces OPK of the anti-pseudomonas antibody Cam004.) Thus, although half-life extension was desirable for an anti-ClfA antibody, the YTE mutation was not suitable for SAR114.

Borrok et al., (J. Biol. Chem., 290(7): 4282-4290 (2015).) studied the effects of other Fc alterations, including the "N3" variant. The "N3" variant contains the sequence CSWHLC (SEQ ID NO:19) in the CH3 domain instead of the wild-type sequence (LHNHYT; SEQ ID NO:22) at those same positions. This Fc variant also increases half-life (see FIG. 9, top panel), but as shown in FIG. 6, does not reduce OPK killing of the anti-bacterial antibodies Cam004 (top panel) or 2F4 (bottom panel).

Therefore, the effect of the N3 mutation on binding of SAR114 was evaluated. In these experiments, the Biacore platform was used to determine the kinetic rate/affinity ($K_D$) constants for binding of parental and Fc-variant antibodies, SAR-114 and SAR114-N3, respectively, against CLFA001, CLFA002, and CLFA004 proteins. The results are shown in Table 3 below.

TABLE 3

SAR-114 and SAR114-N3 binding affinities for the three
main ClfA genotypes

| Capture | Sample | Ka(M$^{-1}$s$^{-1}$) | Kd (s$^{-1}$) | KD (pM) |
|---|---|---|---|---|
| SAR114-N3 | CLFA001 | 3.383E+6 | 7.725E−4 | 228 |
| SAR114-N3 | CLFA002 | 3.921E+6 | 10.41E−4 | 265 |
| SAR114-N3 | CLFA004 | 2.387E+6 | 7.558E−4 | 316 |
| SAR114 | CLFA001 | 3.911E+6 | 6.013E−5 | 15.4 |
| SAR114 | CLFA002 | 3.816E+6 | 1.821E−4 | 47.7 |
| SAR114 | CLFA004 | 2.968E+6 | 6.210E−5 | 20.9 |

The kinetic fit to a 1:1 binding model were adequate. SAR114 and SAR114-N3 both bind to CLFA001, CLFA002, and CLFA004 with similar affinities. However, the binding ($K_D$) of SAR114 to all CLFA proteins was about 10-fold tighter than that of SAR114-N3. The weaker binding of SAR114-N3 is attributable to faster off-rates.

The ability of SAR114-N3 to inhibit fibrinogen binding was also assessed. In these assays, ClfA binding to fibrinogen was measured in the presence of serially diluted (200 to 0.5 µg/ml) of SAR114, SAR114-N3, or a control IgG antibody. The results are shown in FIG. 7 and Table 4 below.

TABLE 4

SAR-114 and SAR114-N3 inhibition of fibrinogen binding

| IC50 (µg/ml) | SAR114 | SAR114-N3 |
|---|---|---|
| ClfA001 | 2.576 | 2.134 |
| ClfA002 | 2.910 | 3.108 |
| ClfA004 | 1.720 | 2.516 |

These data demonstrate that SAR114-N3 inhibits the binding of the three main ClfA genotypes to fibrinogen.

Example 3

This example describes the generation of SAR114-N3Y, which has improved stability as compared to SAR114-N3.

However, the "N3" variant contains a tryptophan (W434) that contributes to enhanced FcRn affinity, but also resulted in light sensitivity such that normal light conditions resulted in about 20% monomer loss over the course of one week, and intense light conditions resulted in more than 60% monomer loss in the same time period. Non-oxidizable hydrophobic residues (F, Y, L, I, V, A, and S) were substituted for the tryptophan (W434) and their effect on SAR114 half-life, OPK, and light sensitivity were evaluated. The F and Y substitutions were most similar to SAR114 N3 in terms of binding, and both had similar half-life extensions as the N3 alteration (see FIG. 9, top panel). A photostability assessment was conducted on SAR114 antibodies with the F ("N3F"; SEQ ID NO:20) and Y ("N3Y; SEQ ID NO:21) alterations. In this assessment, the mAbs were exposed to CWL (conventional white light) at 2 kLux/hr (intensity measure) at 23° C. for 14 days, and the monomer purities observed are summarized in Table 5 below.

TABLE 5

SAR114-N3F and SAR114-N3Y stability

| Clone | Monomer purity at T0 | Monomer purity at 7 days | Monomer purity at 14 days |
|---|---|---|---|
| N3F | 95.9% | 91.8% | 86.2% |
| N3Y | 98.9% | 97.6% | 95.3% |

The results demonstrate that N3Y has superior light stability. Agglutination and fibrinogen potency assays also indicated that N3Y had better activity than N3F as shown in FIG. 8. Measurements of antibody levels in mice demonstrated that both N3Y and N3F had similar pK values to N3 mutant (FIG. 9, top panel), and OPK killing of the N3Y variant was unchanged (FIG. 9, bottom panel).

Example 4

This example describes the effects of SAR114 or SAR114 N3Y anti-ClfA monoclonal antibody, alone or in combination with an anti-alpha toxin (AT) monoclonal antibody, in a murine bacteremia model.

Groups of ten 6-8 week old female BALB/c mice (Envigo, Huntingdon, Cambridgeshire, United Kingdom) were passively immunized by intra-peritoneal (IP) injection of an isotype control IgG (c-IgG), the SAR114 anti-ClfA monoclonal antibody, and/or the MEDI4893* anti-AT monoclonal antibody. Mice were challenged 24 hours later by intravenous (IV) injection of an $LD_{90}$ of *S. aureus* clinical isolates. Survival was monitored over two weeks. Statistical analysis of specific anti-staphylococcal antigen versus c-IgG was performed with a Log Rank (Mantel Cox) test. Data were considered statistically different if $p<0.05$.

SAR114 (15 mg/kg (mpk)) prophylaxis resulted in increased survival compared to an isotype control IgG (c-IgG) following challenge with *S. aureus* isolates representing sequence types (ST) ST8, ST5 or ST30, which were confirmed to encode ClfA genotypes ClfA001, 002, and 004 respectively, as shown in FIG. 10. Similar to the combination of the 11H10 and MEDI4893* antibodies, prophylaxis with the combination of SAR114 and MEDI4893* (7.5 mg/kg (mpk) each) significantly increased survival relative to c-IgG following challenge with all strains tested, and provided a benefit over the corresponding individual monoclonal antibodies against some strains (Tkaczyk et al., supra).

The results of this experiment demonstrate that the anti-ClfA SAR114 monoclonal antibody is functional in vivo and suggests that the combination of SAR114 and an anti-AT monoclonal antibody provides broader strain coverage for *S. aureus* prophylaxis.

Example 5

This example describes the effects of SAR114 anti-ClfA monoclonal antibody, alone or in combination with an anti-alpha toxin (AT) monoclonal antibody, in a diabetic murine lethal bacteremia model.

Groups of 6-week old diabetic BKS.Cg-Dock7$^{m}$+/+Lepr$^{db}$/J male mice were immunized by intra-peritoneal (IP) injection of an isotype control IgG (c-IgG), the SAR114 anti-ClfA monoclonal antibody, and/or the MEDI4893* anti-AT monoclonal antibody. Mice were challenged 24 hours later by intravenous (IV) injection of $LD_{90}$ (5e7CFU) of *S. aureus* clinical isolates SF8300. Survival was monitored over two weeks. FIG. 11, top panel. Ten animals were euthanized after 48 hours for bacterial enumeration in the kidneys (FIG. 11, middle panel) and liver (FIG. 11, bottom panel). Statistical analysis of specific anti-staphylococcal antigen versus c-IgG was performed with a Log Rank (Mantel Cox) test. Data were considered statistically different if $p<0.05$.

SAR114 (15 mg/kg (mpk)) prophylaxis resulted in increased survival compared to an isotype control IgG (c-IgG) following the challenge, and prophylaxis with the combination of SAR114 and MEDI4893* (7.5 mg/kg (mpk) each) significantly increased survival relative to c-IgG following the challenge. FIG. 11, top panel. The combination of SAR114 and MEDI4893* (7.5 mg/kg (mpk) each) also significantly decreased bacteria in the kidneys (FIG. 11, middle panel) and liver (FIG. 11, bottom panel).

The results of this experiment demonstrate that the anti-ClfA SAR114 monoclonal antibody is functional in vivo and suggests that the combination of SAR114 and an anti-AT monoclonal antibody provides protection against CA-MRSA SF8300 induced lethal bacteremia in diabetic db/db mice.

Example 6

This example describes the effects of SAR114 anti-ClfA monoclonal antibody, alone or in combination with an anti-alpha toxin (AT) monoclonal antibody on pro-inflammatory cytokine levels in murine bacteremia models.

Groups of 6-week old diabetic (db) BKS.Cg-Dock7$^{m}$+/+Lepr$^{db}$/J male mice (n=20) and non-diabetic C57/B6 (B6) male mice (n=20) were immunized by intra-peritoneal (IP) injection of an isotype control IgG (c-IgG), the SAR114 anti-ClfA monoclonal antibody, and/or the MEDI4893* anti-AT monoclonal antibody. Mice were challenged 24 hours later by intravenous (IV) injection of $LD_{90}$ of *S. aureus* clinical isolates SF8300. Ten animals per group were euthanized after 8 hours or 24 hours, and blood was collected from cardiac punctures. Pro-inflammatory cytokines were measured from plasma using a Mesoscale Multiplex pro-inflammatory cytokine kit. Statistical differences between group were analyzed with a Mann-Whitney U test, and considered statistically different if $p<0.05$.

The combination of SAR114 and MEDI4893* significantly decreased IL-6, TNF-α, and KC levels at 24 hours in diabetic db/db mice as shown in Table 6.

TABLE 6

SAR114 and MEDI4893* decreases pro-inflammatory cytokines

| Cytokine | Time | Mice | MEDI4893* | SAR114 | MEDI4893* and SAR114 |
|---|---|---|---|---|---|
| IL-6 | 8 hrs | B6 | | 0.004 | |
| IL-6 | 8 hrs | db | | | |
| IL-6 | 24 hrs | B6 | 0.0156 | 0.0041 | 0.008 |
| IL-6 | 24 hrs | db | 0.0034 | 0.043 | 0.011 |
| TNF-α | 8 hrs | B6 | | 0.0017 | 0.0002 |

TABLE 6-continued

SAR114 and MEDI4893* decreases pro-inflammatory cytokines

| Cytokine | Time | Mice | MEDI4893* | SAR114 | MEDI4893* and SAR114 |
|---|---|---|---|---|---|
| TNF-α | 8 hrs | db | 0.0503 | 0.076 | 0.0015 |
| TNF-α | 24 hrs | B6 | 0.028 | | 0.0014 |
| TNF-α | 24 hrs | db | | 0.0055 | 0.038 |
| KC | 8 hrs | B6 | | <0.0001 | |
| KC | 8 hrs | db | 0.032 | 0.0127 | 0.0008 |
| KC | 24 hrs | B6 | | 0.0006 | 0.0002 |
| KC | 24 hrs | db | 0.008 | 0.028 | 0.014 |

The data are representative of three independent experiments.

The combination also significantly decreased IL-6, TNF-α, and KC levels at 24 hours in non-diabetic C57/B6 mice.

Example 7

This example describes the effects of SAR114 anti-ClfA monoclonal antibody, alone or in combination with an anti-alpha toxin (AT) monoclonal antibody, on liver damage in a diabetic murine bacteremia model.

Figure 12:
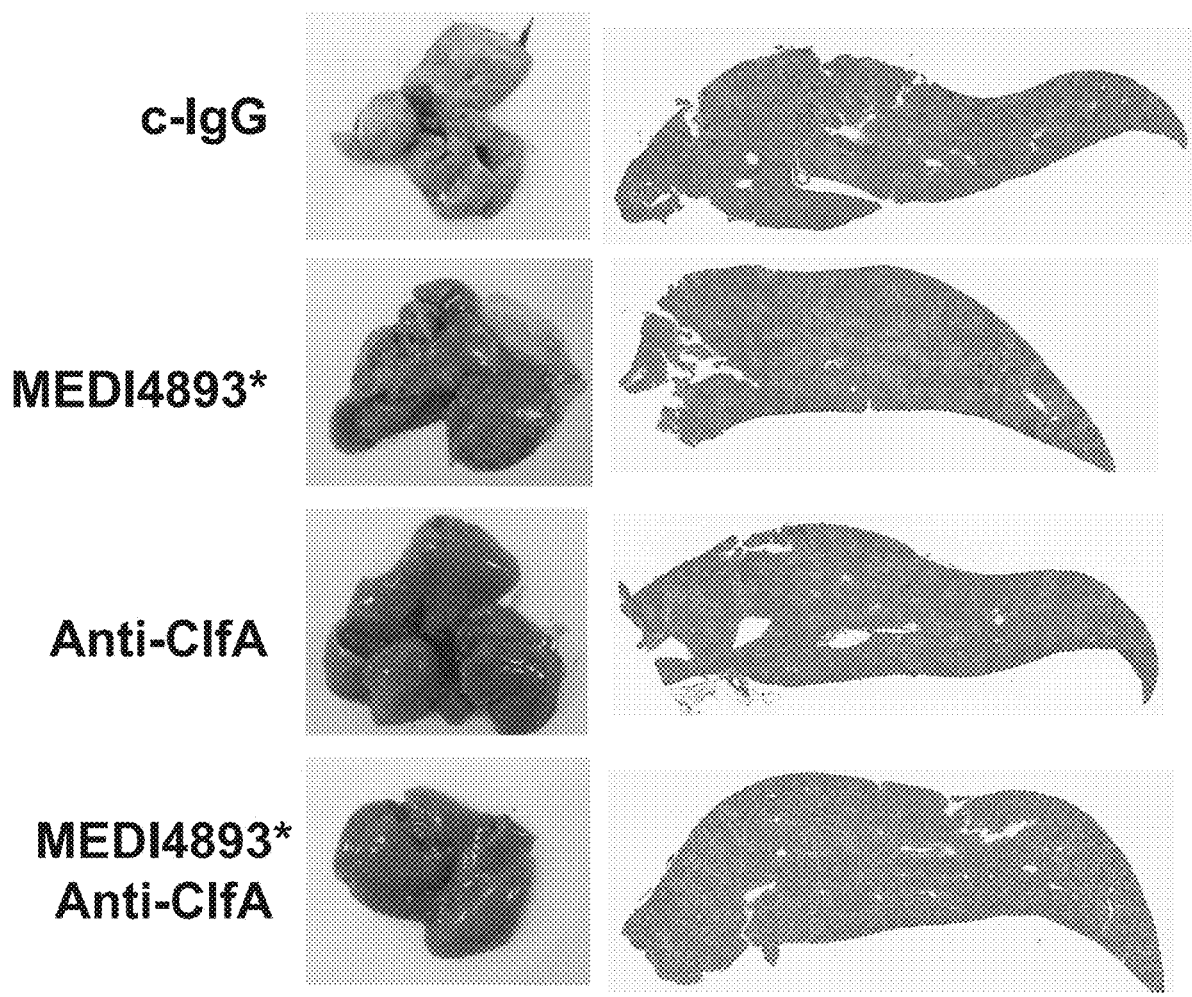

Groups of 6-week old diabetic BKS.Cg-Dock7$^m$+/+Lep-r$^{db}$/J male mice (n=10) were immunized by intra-peritoneal (IP) injection of an isotype control IgG (c-IgG), the SAR114 anti-ClfA monoclonal antibody (15 mg/kg (mpk)), the MEDI4893* anti-AT monoclonal antibody (15 mpk), or a combination of SAR114+MEDI4893* (15 mpk each). Mice were challenged 24 hours later by intravenous (IV) injection of LD$_{90}$ of S. aureus clinical isolates SF8300. Mice were euthanized 48 h after infection, and livers harvested. Gross pathology was recorded photographically (FIG. 12, left panel), and liver section stained with hematoxylin/eosin after fixation with 10% formalin (FIG. 12, right panel). The SAR114 antibody, the MEDI4893* antibody, and the combination of SAR114+MEDI4893* all prevented liver damage in diabetic mice exposed to S. aureus.

Example 8

This example describes the effects of SAR114 anti-ClfA monoclonal antibody, alone or in combination with an anti-alpha toxin (AT) monoclonal antibody, in a murine diabetic bacteremia model.

Figure 13:
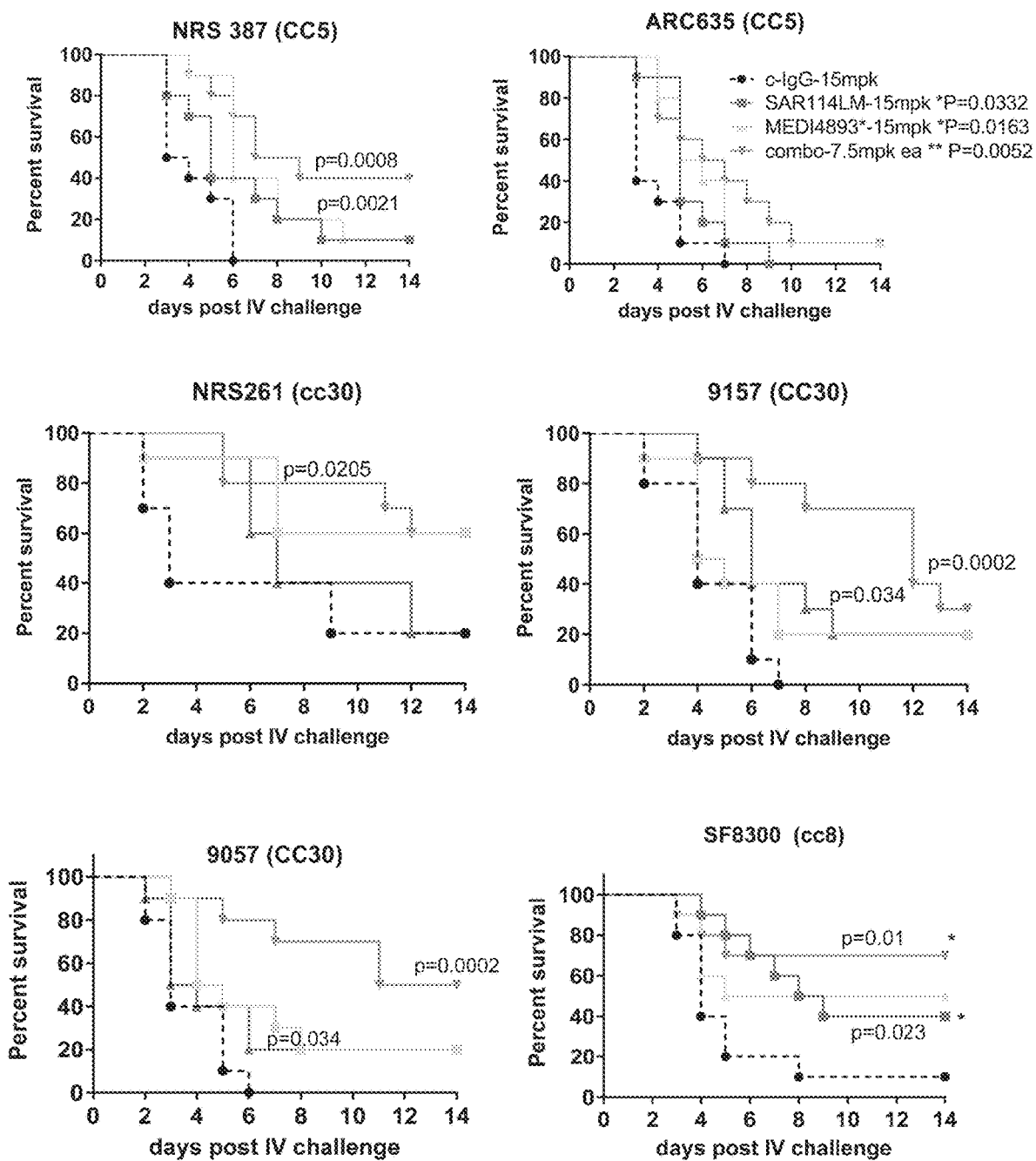

Groups of 6-week old diabetic BKS.Cg-Dock7$^m$+/+Lep-r$^{db}$/J male mice (n=10) were immunized by intra-peritoneal (IP) injection of an isotype control IgG (c-IgG), the SAR114 anti-ClfA monoclonal antibody, and/or the MEDI4893* anti-AT monoclonal antibody. Mice were challenged 24 hours later by intravenous (IV) injection of an LD$_{90}$ of S. aureus clinical isolates. Survival was monitored over two weeks. FIG. 13.

The combination of SAR114 and MEDI4893* (7.5 mg/kg (mpk) each) increased survival relative to c-IgG following challenge with most strains tested, and also provided a benefit over the corresponding individual monoclonal antibodies in most strains.

The results of this experiment demonstrate that the anti-ClfA SAR114 monoclonal antibody is functional in vivo and suggests that the combination of SAR114 and an anti-AT monoclonal antibody provides broader strain coverage for S. aureus prophylaxis in diabetic mice.

Example 9

This example describes the generation of a bispecific monoclonal antibody that specifically binds to both ClfA and AT and its efficacy in vitro.

Because passive immunization with the combination of an anti-ClfA monoclonal antibody and an anti-AT monoclonal antibody provided a benefit for strain coverage in lethal bacteremia and retained the anti-AT protective capacity in murine dermonecrosis and pneumonia models (Tkaczyk et al., supra), a bispecific antibody (BiSAb) directed against ClfA and AT was generated to determine if such a bispecific antibody provided a benefit over the combination of the corresponding individual antibodies. To this end, BiSAbs were engineered as previously described (see, e.g., Dimasi et al., J. Mol. Biol., 393: 672-692 (2009); and Coloma, M. J. and S. L. Morrison, Nat. Biotechnol., 15: 159-163 (1997)). Briefly, anti-ClfA mAbs 11H10 or SAR114 were used as IgG scaffold, and MEDI4893* was grafted in scFv format. MEDI4893* scFv was synthesized in the VL-VH format with a 20-amino acid (GGGGSx4) linker between the light and heavy variable domains (GeneArt, ThermoFisher Scientific, Waltham, Mass.). "BiS$_2$" antibodies were constructed by fusing MEDI893* scFv sequences to the N-terminus of the heavy chains of 11H10 or SAR114 anti-ClfA IgG1. "BiS$_3$" constructs were generated by appending the linker-scFv of MEDI4893* to the C terminus of the heavy chain of 11H10 or SAR114. The BiS$_2$ and BiS$_3$ constructs are illustrated schematically in FIG. 14. BiS$_2$ and BiS$_3$ molecules were expressed by transient transfection in 293 cells, purified by protein A affinity chromatography, and polished by size exclusion chromatography. The integrity of each molecule was assessed by mass spectrophotometry and by intact mass and peptide mapping to verify proper formation of engineered and endogenous disulfide bounds. The BiS$_2$ and BiS$_3$ formats were selected because the scFv is located in disparate locations on the IgG and the only way to determine if one format has an advantage over another is to test them empirically for the antibody specificities of interest.

To understand if the BiSAbs retained the functional activities of the corresponding individual monoclonal antibodies, the ability of each BiSAb to inhibit AT-dependent rabbit red blood cell (RBC) lysis and inhibit fibrinogen binding to ClfA001, ClfA002 and ClfA004 was assessed. The rabbit RBC hemolytic assay was performed by mixing serial dilutions of the BiS Abs and MEDI4893* (500 to 1.7 nM) with AT (0.1 μg/ml=3 nM) and incubating with 50 μl of washed rabbit RBC (Peel Freeze) for 1 hour at 37° C. In some assays, anti-AT scFv of BisAb was saturated with 10M excess of ClfA (5 μM). Plates were then centrifuged at 1200 rpm for 3 minutes, and 50 μl of supernatant was transferred to new plates. Non-specific human IgG1 R347 was used as negative control (c-IgG) (see, e.g., Tkaczyk et al., Clin. Vaccine Immunol., 19: 377-385 (2012)). OD450 nm was measured with a spectrophotometer (Molecular Devices, Sunnyvale, Calif.). Inhibition of hemolysis was calculated using the following equation:

100−(100*[ODAT+mAb]/[ODAT]).

For the fibrinogen-binding assay, NUNC MAXISORP™ plates (ThermoFisher Scientific, Waltham, Mass.) were coated overnight at 4° C. with 2 μg/ml human fibrinogen (Sigma Aldrich, St. Louis, Mo.), washed 3 times with PBS containing 0.1% Tween 20 (wash buffer) and blocked for 1 hour at room temperature (RT) with 200 μl/well casein (ThermoFisher Scientific, Waltham, Mass.). Following 3 washes, the plates were incubated for 1 hour at RT with a mix of 50 μl Avi-tag ClfA221-559 (2 μg/ml) and serial dilutions of anti-ClfA monoclonal antibody or BiS antibody in 100 μl final volume PBS. In some assays, the anti-ClfA IgG1 of the BiSAb was saturated with 10M excess of AT (6.6 mM). After washes, bound ClfA was detected using horseradish peroxidase (HRP)-conjugated streptavidin (1:20000, GE Healthcare, Chicago, Ill.) and 100 µl 3,3',5,5'-tetramethylbenzidine (TMB) substrate (KPL). The reaction was stopped after 10 minutes with 100 µl 0.2 M $H_2SO_4$. Plates were read on a spectrophotometer at OD450 nm. Percentage inhibition of ClfA binding to fibrinogen was calculated using the following formula: 100−(100* $[OD_{ClfA+mAb}]/[OD_{ClfA,no\ mAb}]$).

Figure 15:
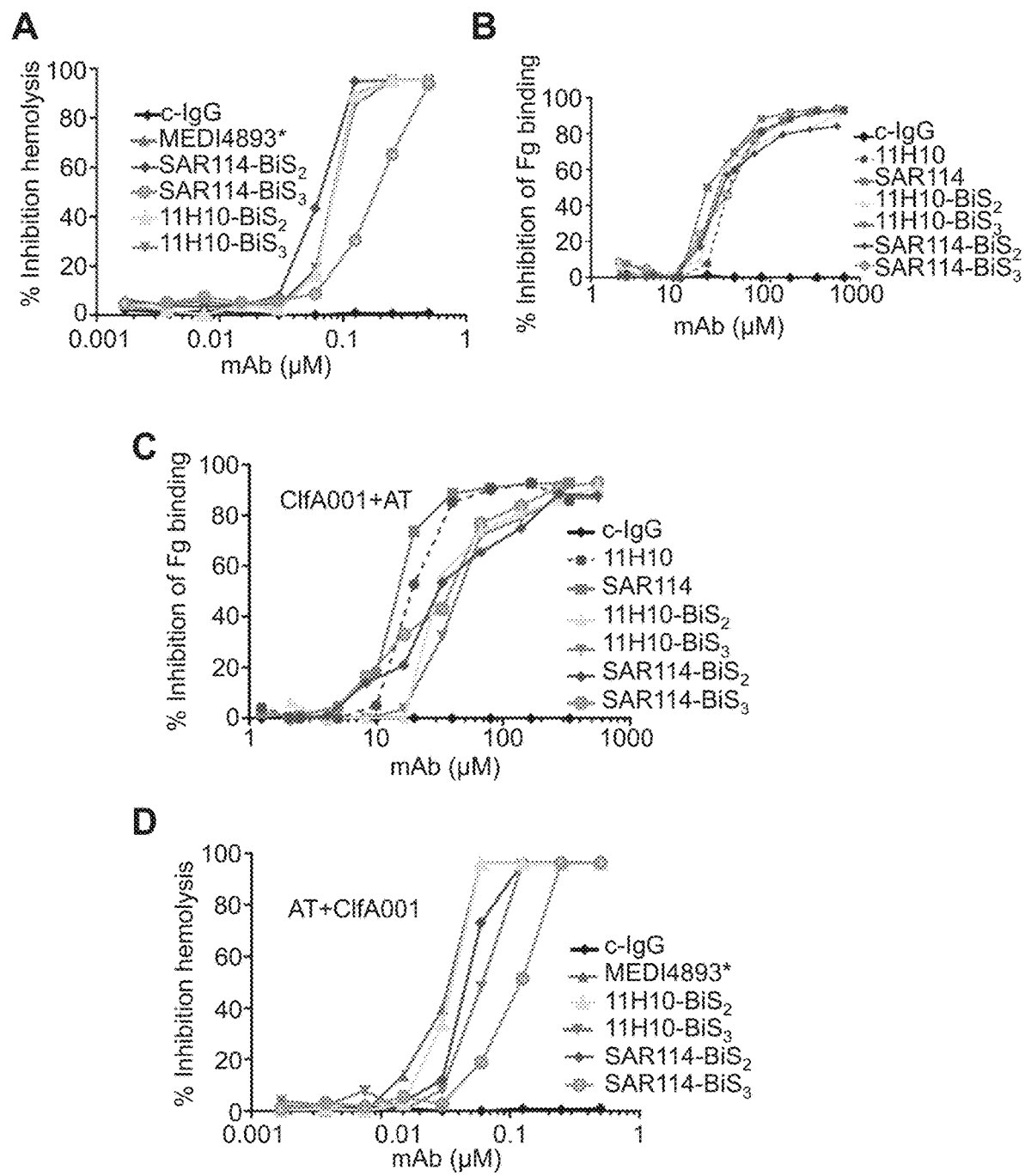
Figure 16:
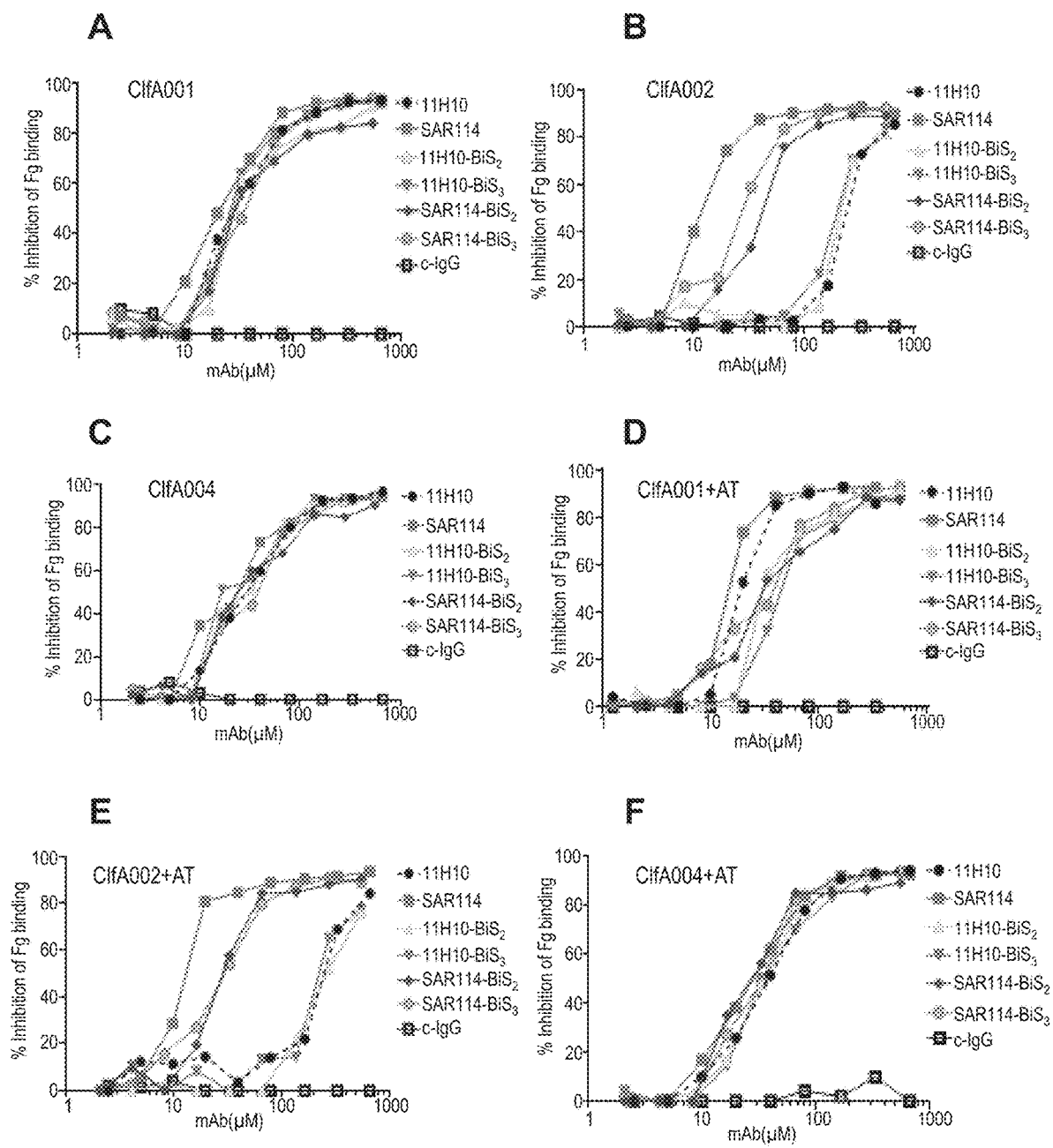

The 11H10-$BiS_2$ and $BiS_3$ antibodies and the SAR114-$BiS_2$ antibody exhibited $IC_{50}$ values similar to MEDI4893* in an AT hemolytic assay, whereas SAR114-$BiS_3$ exhibited reduced AT neutralization activity, as shown in FIG. 15A. Both 11H10 BiSAbs and the SAR114 $BiS_3$Ab exhibited $IC_{50}$ values similar to the respective parental anti-ClfA IgG in the fibrinogen binding inhibition assay, whereas the SAR114 $BiS_2$Ab lost some activity against ClfA002 but was still superior to 11H10, as shown in FIG. 15B, FIG. 16, and Table 7. The BiSAbs also mediated similar opsonophagocytic bacterial killing (OPK) as the parental anti-ClfA IgG, as shown in FIG. 17. Importantly, saturation of the anti-AT scFv in the presence of 10 M excess of AT did not interfere with anti-ClfA activity in the fibrinogen binding assay, as shown in FIG. 15C. Similarly, saturation of ClfA binding with a 10 M ClfA excess did not decrease AT neutralizing activity of the BiSAbs in the hemolytic assay, as shown in FIG. 15D.

TABLE 7

$IC_{50}$ for SAR114 and 11H10-BiS2 and BiS3 molecules in fibrinogen binding assay

| $IC_{50}$ (nM) | SAR114 | $BiS_2$ | $BiS_3$ |
| --- | --- | --- | --- |
| ClfA001 | 19.16 | 90.31 | 41.78 |
| ClfA002 | 14.26 | 40.48 | 27.52 |
| ClfA004 | 8.083 | 34.69 | 20.93 |
| ClfA001 | 12.67 | 124.3 | 57.75 |
| ClfA002 | 493.7 | 3023 | 1530 |
| ClfA004 | 3.094 | 1.504 | 0.9786 |

The results of this example demonstrate that the anti-ClfA/AT BiS molecules retain in vitro functional activity that in most cases was similar to the parental IgG, and this activity was not diminished in the presence of a 10-fold molar excess of the other antigen recognized by the BiSAb.

Example 10

This example describes the protective effects of an anti-ClfA/AT bispecific antibody in an *S. aureus* lethal bacteremia model.

Figure 10:
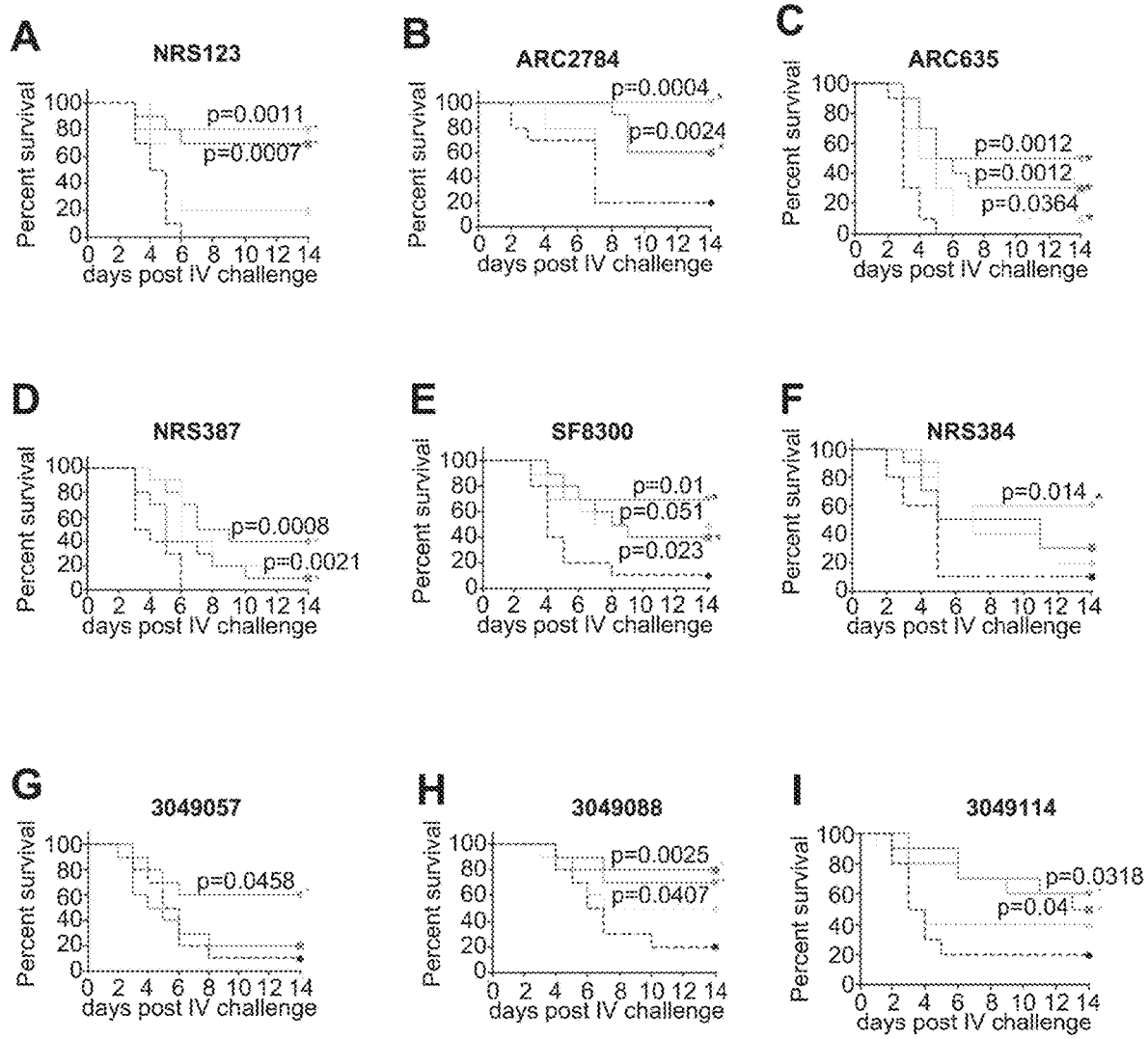
Figure 10:
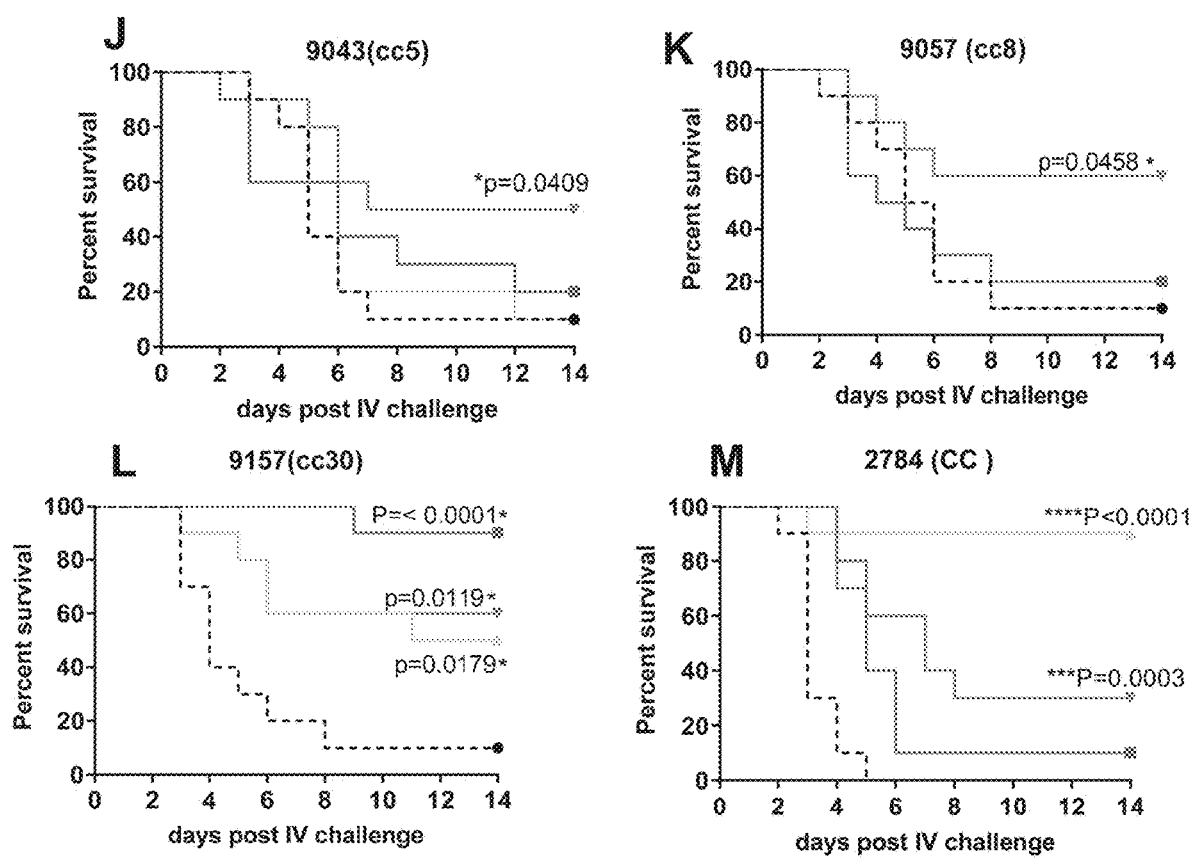
Figure 11:
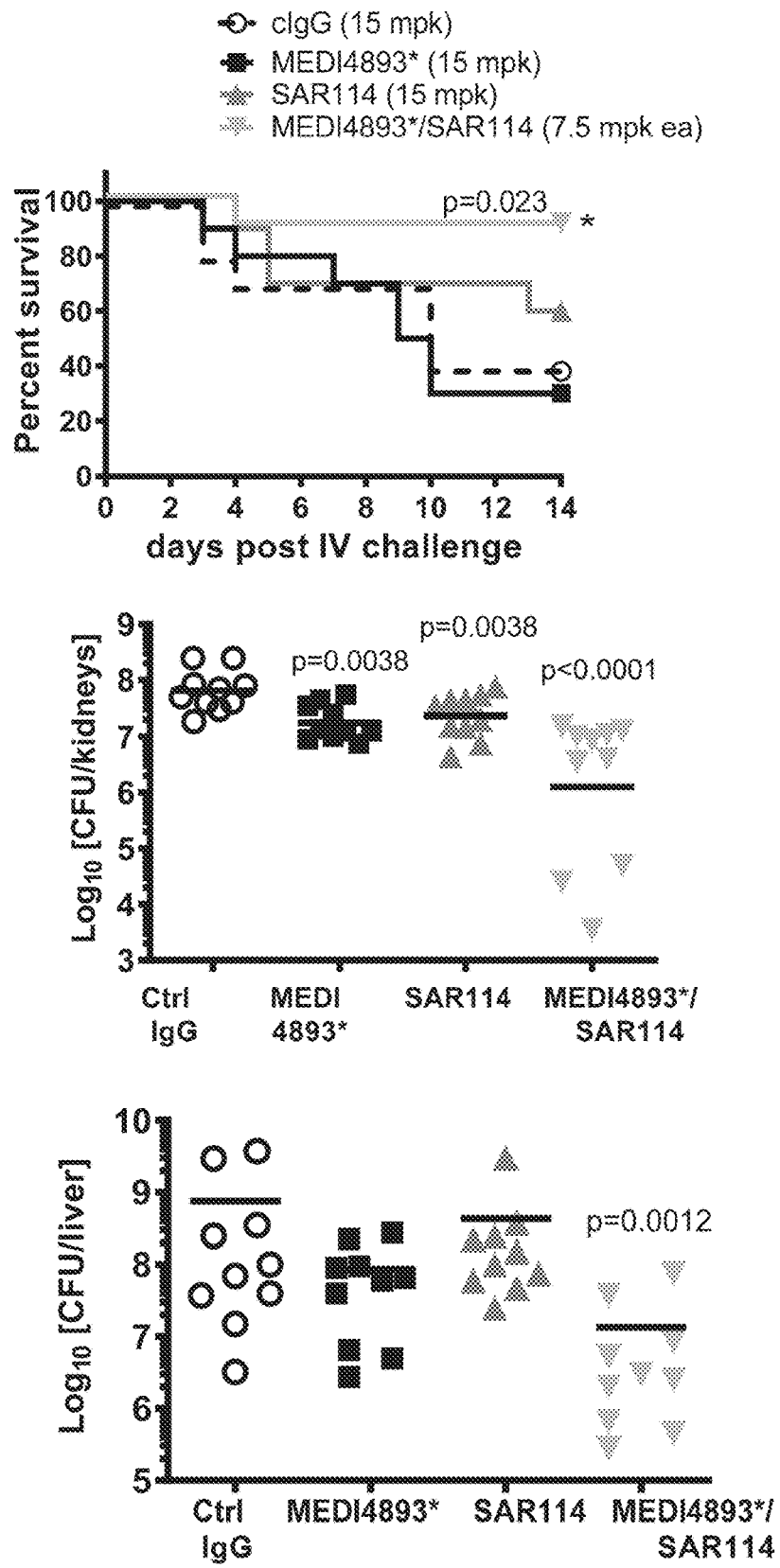
Figure 18:
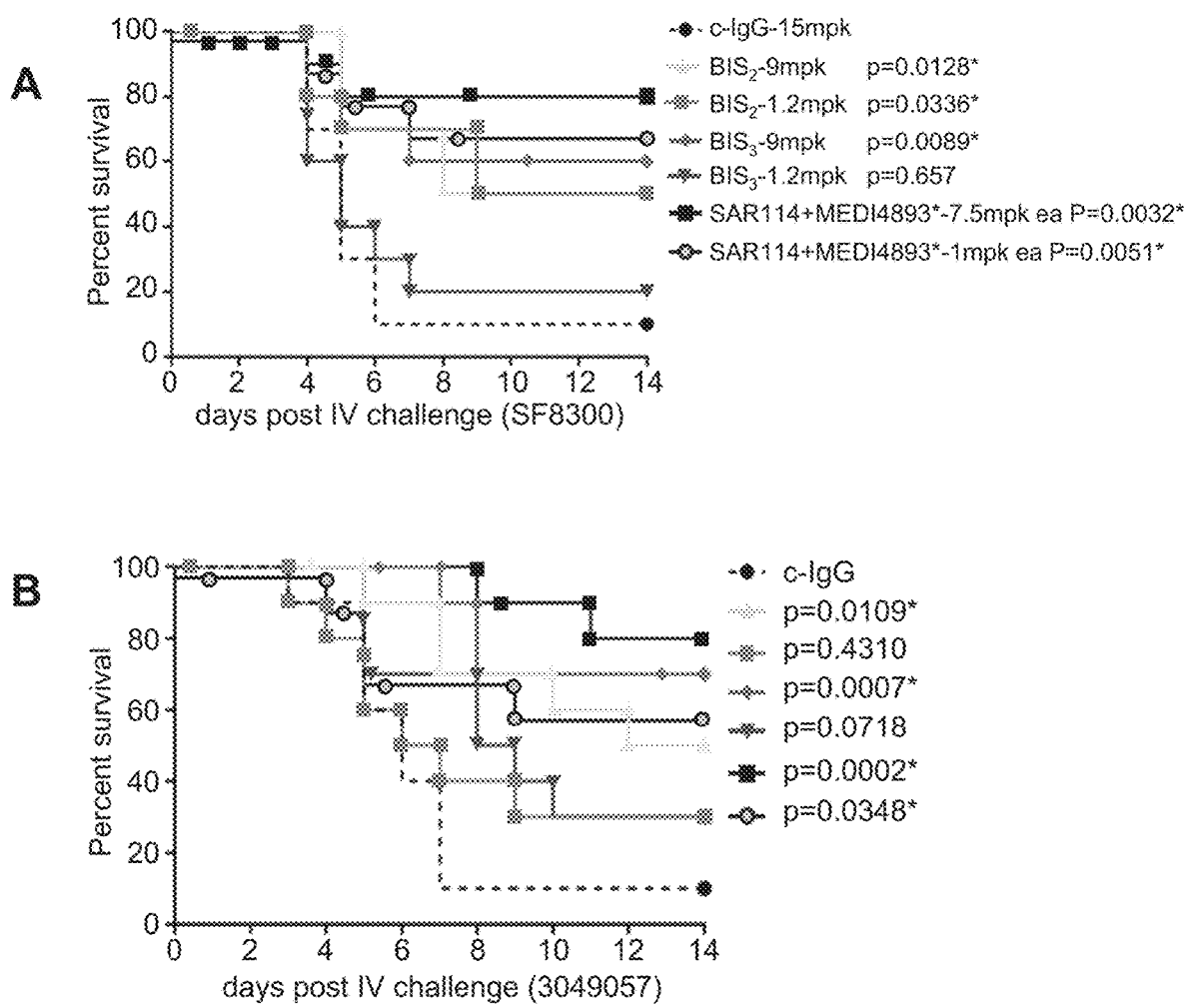
Figure 18:
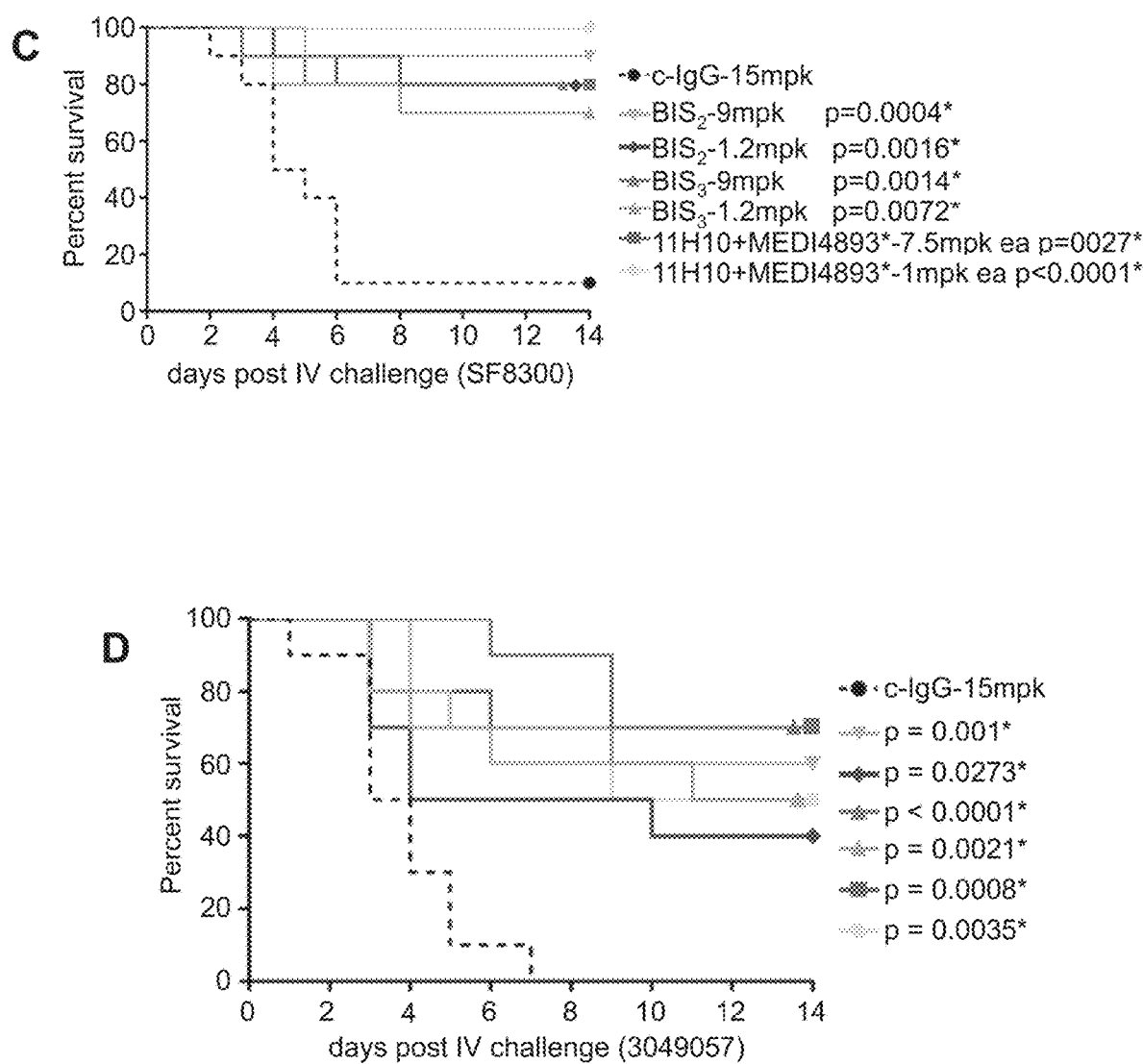

Mice were passively immunized with the anti-ClfA SAR114 antibody and MEDI4893* monoclonal antibody combination (7.5 mpk or 1 mpk each) or equimolar doses of the BiSAbs (9 or 1.2 mpk, respectively) 24 hours prior to IV infection with *S. aureus* strain SF8300 as described in Example 4, and survival was monitored for 14 days. Both SAR114-BiSAbs at 9 mpk exhibited reduced but not significantly different protection (p=0.234 for $BiS_2$ and p=0.412 for $BiS_3$) compared to the monclonal antibody combination at 7.5 mpk each, as shown in FIG. 18A. The monoclonal antibody combination at 1 mpk (p=0.0051 vs c-IgG) and SAR114-$BiS_2$ at 1.2 mpk (p=0.0336 vs c-IgG) significantly increased survival relative to c-IgG. Consistent with the observed loss of AT neutralization activity in vitro (see FIG. 15A), SAR114-$BiS_3$ did not significantly increase survival when administered at 1.2 mpk (p=0.657, FIG. 18A). When tested against *S. aureus* strain 3049057 (MRSA, ST8), a strain where neither monoclonal alone is sufficient for significant protection (see FIG. 10), the SAR114-BiS molecules at 1.2 mpk did not significantly increase survival relative to c-IgG (p=0.4310), whereas an equimolar concentration (1 mpk) of the monoclonal antibody combination did increase survival, as shown in FIG. 18B (p=0.0348 vs c-IgG). This result suggested a defect in the SAR114-$BiS_2$ antibody in vivo. Interestingly, passive immunization with the 11H10-BiSAbs resulted in protection similar to the monoclonal combination at both doses tested (9 mpk and 1.2 mpk) and provided a significant increase in survival relative to c-IgG against both ClfA001 expressing strains, SF8300 and 3049057, as shown in FIGS. 18C and 18D.

The results of this example demonstrate that the anti-ClfA/AT BiSAbs do not provide a benefit over the combination of corresponding individual antibodies. Rather, the SAR114/MEDI4893* bispecific antibody exhibited a loss in protection at lower doses against a strain where the corresponding individual monoclonal antibodies were not sufficient to provide protection.

Example 11

This example describes experiments examining the efficacy of the SAR114/MEDI4893* bispecific antibody in a lethal pneumonia model.

Since SAR114 binds ClfA001 with approximately 1000-fold greater affinity than 11H10 (Table 1), it was hypothesized that SAR114 binding to ClfA sequesters the SAR114/MEDI4893* BiSAb on the bacterial surface, leading to poorer capture and neutralization of AT as it is secreted. AT is a key virulence factor in *S. aureus* pneumonia (Bubeck Wardenburg, J. and O. Schneewind, *J. Exp. Med.*, 205: 287-294 (2008)), and passive immunization with an anti-AT monoclonal antibody alone protects mice from lethal *S. aureus* pneumonia (Foletti et al., *J. Mol. Biol.*, 425(10): 1641-1654 (2013); Hua et al., *Antimicrob. Agents Chemother.*, 58:1108-1117 (2014); and Ragle, B. E., and J. Bubeck Wardenburg, *Infect. Immun.*, 77: 2712-2718 (2009)). Moreover, the anti-ClfA monoclonal antibody does not impact survival in the pneumonia model and the combination of anti-ClfA and anti-AT monoclonal antibodies provides protection similar to an anti-AT mAb alone (Tkaczyk et al., supra). Therefore, to determine if the decreased protection observed with the SAR114-$BiS_2$Abs in the lethal bacteremia model may have resulted from inadequate AT neutralization, female C57/B6 mice (Jackson Laboratory, Bar Harbor, Me.) were injected IP with MEDI4893* alone or in combination with SAR114, or with the SAR114 $BiS_2$ or $BiS_3$ molecules. Pneumonia was induced by intranasal infection with SF8300 ($1e^8$ CFU) as described in Hua et al., supra. Animal survival was monitored for 6 days. Statistical analysis versus c-IgG versus was performed with a Log Rank (Mantel Cox) test. Data were considered statistically different if p<0.05.

Passive immunization with MEDI4893* (15 mpk) alone or in combination with SAR114 resulted in 100% protection following challenge with SF8300. However, passive immunization with SAR114-$BiS_2$ or $BiS_3$ resulted in 30% and 0% survival, respectively, as shown in FIG. 19A. Interestingly, passive immunization with the 11H10$BiS_2$, which has approximately 1000-fold reduced affinity for ClfA (Table 1), provided 100% survival. These results support the conclusion that binding to ClfA on the bacterial surface sequesters SAR114-BiSAbs, thus impairing AT neutralization. To further test this hypothesis, mice were passively immunized with the BiS₂ molecules prior to intranasal (IN) infection with a ClfA isogenic mutant SF8300Δclfa. Prophylaxis with SAR114-BiSAb provided protection against SF8300Δclfa similar to MEDI4893*, as shown in FIG. 19B.

The results of this example provide further evidence that SAR114-BiSAb binding to surface-localized ClfA prevents effective neutralization of soluble AT.

Example 12

Figure 20:
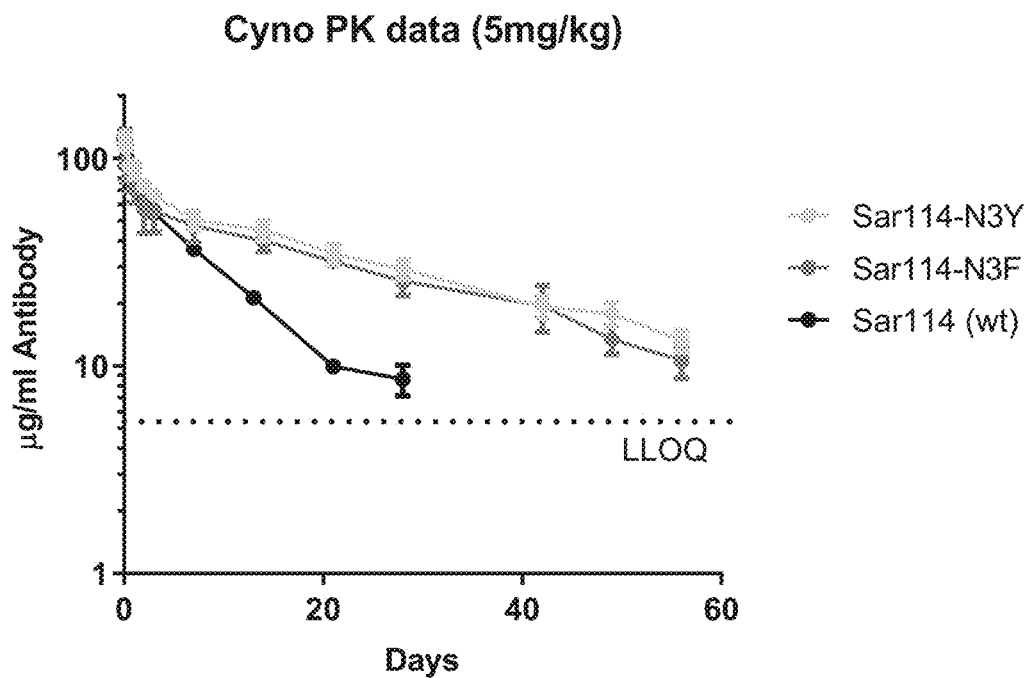
FIG. 20 shows the levels of SAR114, SAR114 N3F, and SAR114 N3Y is cynomolgus monkeys over a period of 60 days after administration of 5 mg/kg of the antibodies.

This example describes experiments examining the pharmacokinetics (pK) of SAR114 antibodies in cynomolgus monkeys. The monkeys were treated by intravenous (IV) administration with 5 mg/kg of SAR114, SAR114 N3F, or SAR114 N3Y, and antibody levels were measured in the blood over 60 days. The results are shown in FIG. 20 and reported in Table 8 below.

TABLE 8

| Sar114 Construct | Clearance (mL/day/kg) | β-phase $t_{1/2}$ (days) | $AUC_{last}$ (μg*day/ml) |
|---|---|---|---|
| Wild-type | 5.69 ± 0.27 | 10.1 ± 1.5 | 754 ± 21 |
| N3Y | 2.14 ± 0.17 | 23.7 ± 2.4 | 1900 ± 170 |
| N3F | 2.54 ± 0.46 | 20.3 ± 4.1 | 1690 ± 254 |

Cynomolgus monkey PK parameters.

The data above demonstrates that the modified versions of SAR114, and in particular SAR114 N3Y, exhibit an increased half-life in primates. The data above are consistent with what would be predicted from the half life extension studies in mice transgenic for human FcRN. The effective extension of half-life in primates indicates that the half-life of SAR114 N3Y will be appropriately extended and important for proper administration, treatment, and prevention of S. aureus-related disease in humans.

Example 13

This example describes experiments examining the immunogenicity of the N3Y Fc.

The immunogenicity of therapeutic proteins can cause problems including neutralization, accelerated clearance of the therapeutic, and/or adverse events. While human proteins such as antibody framework regions are mostly non-immunogenic, mutations in the Fc regions of antibodies present a potential risk of an immune response. Functional activation assays using human CD4 T-cells are now considered a hallmark of immunogenicity prediction as a result of the chief role of helper T cells in immunogenicity responses. Therefore, the effect of the N3Y in the Fc region of IgG1 on T cell activation was analyzed.

Figure 21:
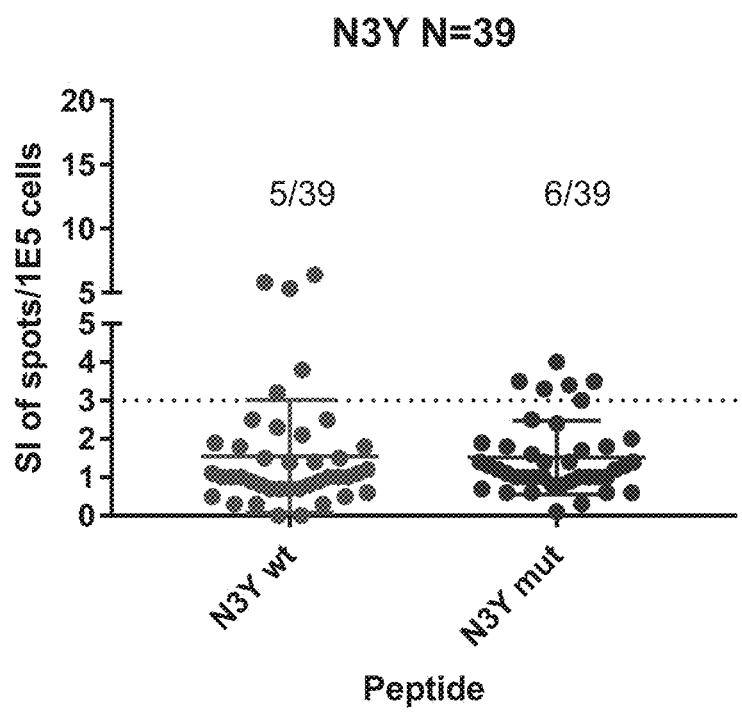
FIG. 21 is a graph illustrating the immunogenicity of wild-type and N3Y Fc regions using an ex vivo PBMC stimulation assay.

In these experiments, PMBCs were isolated from 39 human whole blood collections using Ficole gradients. CD8 cells were then extracted using positive selection, and the cells were enriched by stimulation with 5 different peptide pools and 10 days in vitro expansion with IL-2. The cells were then re-stimulated with an individual peptide library in ELIspot plates for CD4. The results shown in FIG. 21 demonstrate that the NY3 mutation dose not significantly increase immunogenicity as compared to the wildtype Fc region.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An antibody or antigen-binding fragment thereof that specifically binds to a *Staphylococcus aureus* (*S. aureus*) clumping factor A (ClfA) protein, wherein said antibody or antigen-binding fragment comprises a variable heavy chain (VH) comprising the amino acid sequence of SEQ ID NO: 13 and a variable light chain (VL) comprising the amino acid sequence of SEQ ID NO: 14, and wherein said antibody or antigen-binding fragment comprises a heavy chain constant domain comprising the amino acid sequence of CSYHLC (SEQ ID NO: 21).

2. A composition comprising the antibody or antigen-binding fragment thereof of claim 1 and a pharmaceutically-acceptable carrier.

3. The antibody or antigen-binding fragment thereof of claim 1, wherein the antibody or antigen-binding fragment thereof comprises a heavy chain constant region comprising a YTE mutation.

4. The antibody or antigen-binding fragment thereof of claim 1, wherein the antibody is a full-length antibody.

5. The antibody or antigen-binding fragment thereof of claim 1, wherein the antibody is an IgG antibody.

6. The antibody or antigen-binding fragment thereof of claim 5, wherein the antibody is an IgG1 antibody.

7. A composition comprising the antibody of claim 6 and a pharmaceutically acceptable carrier.

8. A composition comprising the antibody of claim 5 and a pharmaceutically-acceptable carrier.

9. The antibody or antigen-binding fragment thereof of claim 1, wherein the heavy chain constant domain comprises the amino acid sequence of MHEACSYHLCQKSLSLS (SEQ ID NO:23).

10. The antibody or antigen-binding fragment thereof of claim 9, wherein the antibody is an IgG antibody.

11. The antibody or antigen-binding fragment thereof of claim 10, wherein the antibody is an IgG1 antibody.

12. The antibody or antigen-binding fragment thereof of claim 1, wherein the heavy chain constant domain comprises the amino acid sequence of SEQ ID NO:24.

13. The antibody or antigen-binding fragment thereof of claim 12, wherein the antibody is an IgG antibody.

14. The antibody or antigen-binding fragment thereof of claim 13, wherein the antibody is an IgG1 antibody.

15. A composition comprising the antibody of claim 14 and a pharmaceutically acceptable carrier.

16. A composition comprising the antibody of claim 13 and a pharmaceutically acceptable carrier.

17. An antibody that specifically binds to a *S. aureus* ClfA protein, wherein the antibody comprises a heavy chain comprising the amino acid sequence set forth in SEQ ID NO: 50 and a light chain comprising the amino acid sequence set forth in SEQ ID NO: 26.

18. A composition comprising the antibody of claim 17 and a pharmaceutically-acceptable carrier.

* * * * *

SEQUENCE LISTING

```
<160> NUMBER OF SEQ ID NOS: 52

<210> SEQ ID NO 1
<211> LENGTH: 5
<212> TYPE: PRT
<213> ORGANISM: Artificial Sequence
<220> FEATURE:
<223> OTHER INFORMATION: SAR114 VH CDR1
```

```
<400> SEQUENCE: 1

Asn Ser Tyr Trp Ser
1               5

<210> SEQ ID NO 2
<211> LENGTH: 16
<212> TYPE: PRT
<213> ORGANISM: Artificial Sequence
<220> FEATURE:
<223> OTHER INFORMATION: SAR114 VH CDR2

<400> SEQUENCE: 2

Tyr Leu Tyr Ser Ser Gly Arg Thr Asn Tyr Thr Pro Ser Leu Lys Ser
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: SAR114 VH CDR3

<400> SEQUENCE: 3

Thr His Leu Gly Gly Phe His Tyr Gly Gly Gly Phe Trp Phe Asp Pro
1               5                   10                  15

<210> SEQ ID NO 4
<211> LENGTH: 11
<212> TYPE: PRT
<213> ORGANISM: Artificial Sequence
<220> FEATURE:
<223> OTHER INFORMATION: SAR114 VL CDR1

<400> SEQUENCE: 4

Arg Ala Ser Gln Ser Ile Thr Ser Tyr Leu Asn
1               5                   10

<210> SEQ ID NO 5
<211> LENGTH: 7
<212> TYPE: PRT
<213> ORGANISM: Artificial Sequence
<220> FEATURE:
<223> OTHER INFORMATION: SAR114 VL CDR2

<400> SEQUENCE: 5

Ala Ser Ser Ser Leu Gln Ser
1               5

<210> SEQ ID NO 6
<211> LENGTH: 9
<212> TYPE: PRT
<213> ORGANISM: Artificial Sequence
<220> FEATURE:
<223> OTHER INFORMATION: SAR114 VL CDR3

<400> SEQUENCE: 6

Gln Glu Ser Tyr Ser Thr Pro Pro Thr
1               5

<210> SEQ ID NO 7
<211> LENGTH: 5
<212> TYPE: PRT
<213> ORGANISM: Artificial Sequence
<220> FEATURE:
<223> OTHER INFORMATION: MEDI4893 and MEDI4893* VH CDR1
```

```
<400> SEQUENCE: 7

Ser His Asp Met His
1               5

<210> SEQ ID NO 8
<211> LENGTH: 16
<212> TYPE: PRT
<213> ORGANISM: Artificial Sequence
<220> FEATURE:
<223> OTHER INFORMATION: MEDI4893 and MEDI4893* VH CDR2

<400> SEQUENCE: 8

Gly Ile Gly Thr Ala Gly Asp Thr Tyr Tyr Pro Asp Ser Val Lys Gly
1               5                   10                  15

<210> SEQ ID NO 9
<211> LENGTH: 14
<212> TYPE: PRT
<213> ORGANISM: Artificial Sequence
<220> FEATURE:
<223> OTHER INFORMATION: MEDI4893 and MEDI4893* VH CDR3

<400> SEQUENCE: 9

Asp Arg Tyr Ser Pro Thr Gly His Tyr Tyr Gly Met Asp Val
1               5                   10

<210> SEQ ID NO 10
<211> LENGTH: 11
<212> TYPE: PRT
<213> ORGANISM: Artificial Sequence
<220> FEATURE:
<223> OTHER INFORMATION: MEDI4893 and MEDI4893* VL CDR1

<400> SEQUENCE: 10

Arg Ala Ser Gln Ser Ile Ser Ser Trp Leu Ala
1               5                   10

<210> SEQ ID NO 11
<211> LENGTH: 7
<212> TYPE: PRT
<213> ORGANISM: Artificial Sequence
<220> FEATURE:
<223> OTHER INFORMATION: MEDI4893 and MEDI4893* VL CDR2

<400> SEQUENCE: 11

Lys Ala Ser Ser Leu Glu Ser
1               5

<210> SEQ ID NO 12
<211> LENGTH: 8
<212> TYPE: PRT
<213> ORGANISM: Artificial Sequence
<220> FEATURE:
<223> OTHER INFORMATION: MEDI4893 and MEDI4893* VL CDR3

<400> SEQUENCE: 12

Lys Gln Tyr Ala Asp Tyr Trp Thr
1               5

<210> SEQ ID NO 13
<211> LENGTH: 124
<212> TYPE: PRT
<213> ORGANISM: Artificial Sequence
<220> FEATURE:
<223> OTHER INFORMATION: SAR114 Variable Heavy Chain

<400> SEQUENCE: 13
```

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Gln Asn Ser
            20                  25                  30

Tyr Trp Ser Trp Ile Arg Gln Pro Pro Gly Lys Gly Leu Glu Trp Ile
        35                  40                  45

Gly Tyr Leu Tyr Ser Ser Gly Arg Thr Asn Tyr Thr Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Thr His Leu Gly Gly Phe His Tyr Gly Gly Gly Phe Trp Phe Asp
            100                 105                 110

Pro Trp Gly Gln Gly Thr Leu Val Thr Val Ser Ser
        115                 120

<210> SEQ ID NO 14
<211> LENGTH: 107
<212> TYPE: PRT
<213> ORGANISM: Artificial Sequence
<220> FEATURE:
<223> OTHER INFORMATION: SAR114 Variable Light Chain

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Thr Ser Tyr
            20                  25                  30

Leu Asn Trp Tyr Gln Gln Lys Pro Gly Lys Ala Pro Lys Leu Leu Ile
        35                  40                  45

Tyr Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Glu Ser Tyr Ser Thr Pro Pro
                85                  90                  95

Thr Phe Gly Gln Gly Thr Lys Val Glu Ile Lys
            100                 105

<210> SEQ ID NO 15
<211> LENGTH: 122
<212> TYPE: PRT
<213> ORGANISM: Artificial Sequence
<220> FEATURE:
<223> OTHER INFORMATION: MEDI4893 and MEDI4893* Variable Heavy Chain

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Asp Ser Val Lys
    50                  55                  60

Gly Arg Phe Thr Ile Ser Arg Glu Asn Ala Lys Asn Ser Leu Tyr Leu

```
                65                  70                  75                  80
Gln Met Asn Ser Leu Arg Ala Gly Asp Thr Ala Val Tyr Tyr Cys Ala
                    85                  90                  95

Arg Asp Arg Tyr Ser Pro Thr Gly His Tyr Tyr Gly Met Asp Val Trp
            100                 105                 110

Gly Gln Gly Thr Thr Val Thr Val Ser Ser
        115                 120

<210> SEQ ID NO 16
<211> LENGTH: 106
<212> TYPE: PRT
<213> ORGANISM: Artificial Sequence
<220> FEATURE:
<223> OTHER INFORMATION: MEDI4893 and MEDI4893* Variable Light Chain

<400> SEQUENCE: 16

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Lys Gln Tyr Ala Asp Tyr Trp Thr
                85                  90                  95

Phe Gly Gln Gly Thr Lys Val Glu Ile Lys
            100                 105

<210> SEQ ID NO 17
<211> LENGTH: 126
<212> TYPE: PRT
<213> ORGANISM: Artificial Sequence
<220> FEATURE:
<223> OTHER INFORMATION: SAR72 Variable Heavy Chain

<400> SEQUENCE: 17

Glu Val Gln Leu Val Glu Ser Gly Gly Gly Leu Val Lys Pro Gly Gly
1               5                   10                  15

Ser Leu Arg Val Ser Cys Ala Ala Ser Gly Phe Ser Phe Arg Asn Ala
            20                  25                  30

Leu Met Ser Trp Val Arg Gln Ala Pro Gly Lys Gly Leu Glu Trp Val
        35                  40                  45

Gly Arg Ser Lys Thr Asp Gly Thr Thr Asp Tyr Ala Ala Pro Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Thr Thr Gly Pro Gly Gly Gly Pro Pro Gly Asp Tyr Tyr Tyr Asp Gly
            100                 105                 110

Met Asp Val Trp Gly Gln Gly Thr Thr Val Thr Val Ser Ser
        115                 120                 125

<210> SEQ ID NO 18
<211> LENGTH: 106
```

```
<212> TYPE: PRT
<213> ORGANISM: Artificial Sequence
<220> FEATURE:
<223> OTHER INFORMATION: SAR72 Variable Light Chain

<400> SEQUENCE: 18

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Val Pro Lys Lys Tyr Ala
            20                  25                  30

Tyr Trp Tyr Gln Gln Lys Ser Gly Gln Ala Pro Val Leu Val Ile Tyr
        35                  40                  45

Glu Asp Lys Lys Arg Pro Ser Gly Ile Pro Glu Arg Phe Ser Gly Ser
    50                  55                  60

Ser Ser Gly Thr Met Ala Thr Leu Thr Ile Ser Gly Ala Gln Val Glu
65                  70                  75                  80

Asp Glu Ala Asp Tyr Tyr Cys Tyr Ser Thr Asp Ser Ser Glu Gly Val
                85                  90                  95

Phe Gly Gly Gly Thr Lys Leu Thr Val Leu
            100                 105

<210> SEQ ID NO 19
<211> LENGTH: 6
<212> TYPE: PRT
<213> ORGANISM: Artificial Sequence
<220> FEATURE:
<223> OTHER INFORMATION: N3 Fc Variant

<400> SEQUENCE: 19

Cys Ser Trp His Leu Cys
1               5

<210> SEQ ID NO 20
<211> LENGTH: 6
<212> TYPE: PRT
<213> ORGANISM: Artificial Sequence
<220> FEATURE:
<223> OTHER INFORMATION: N3F Fc Variant

<400> SEQUENCE: 20

Cys Ser Phe His Leu Cys
1               5

<210> SEQ ID NO 21
<211> LENGTH: 6
<212> TYPE: PRT
<213> ORGANISM: Artificial Sequence
<220> FEATURE:
<223> OTHER INFORMATION: N3Y Fc Variant

<400> SEQUENCE: 21

Cys Ser Tyr His Leu Cys
1               5

<210> SEQ ID NO 22
<211> LENGTH: 6
<212> TYPE: PRT
<213> ORGANISM: Artificial Sequence
<220> FEATURE:
<223> OTHER INFORMATION: Wild-type Fc CH3

<400> SEQUENCE: 22

Leu His Asn His Tyr Thr
1               5
```

<210> SEQ ID NO 23
<211> LENGTH: 17
<212> TYPE: PRT
<213> ORGANISM: Artificial Sequence
<220> FEATURE:
<223> OTHER INFORMATION: heavy chain constant domain

<400> SEQUENCE: 23

Met His Glu Ala Cys Ser Tyr His Leu Cys Gln Lys Ser Leu Ser Leu
1               5                   10                  15

Ser

<210> SEQ ID NO 24
<211> LENGTH: 222
<212> TYPE: PRT
<213> ORGANISM: Artificial Sequence
<220> FEATURE:
<223> OTHER INFORMATION: N3Y Fc starting from hinge

<400> SEQUENCE: 24

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Glu Glu Met Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Cys Ser
        195                 200                 205

Tyr His Leu Cys Gln Lys Ser Leu Ser Leu Ser Pro Gly Lys
    210                 215                 220

<210> SEQ ID NO 25
<211> LENGTH: 454
<212> TYPE: PRT
<213> ORGANISM: Artificial Sequence
<220> FEATURE:
<223> OTHER INFORMATION: SAR114 Full-Length Heavy Chain

<400> SEQUENCE: 25

Gln Val Gln Leu Gln Glu Ser Gly Pro Gly Leu Val Lys Pro Ser Glu

```
  1               5                  10                    15
Thr Leu Ser Leu Thr Cys Thr Val Ser Gly Gly Ser Ile Gln Asn Ser
                20                  25                  30

Tyr Trp Ser Trp Ile Arg Gln Pro Gly Lys Gly Leu Glu Trp Ile
            35                  40                  45

Gly Tyr Leu Tyr Ser Ser Gly Arg Thr Asn Tyr Thr Pro Ser Leu Lys
            50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Thr His Leu Gly Gly Phe His Tyr Gly Gly Phe Trp Phe Asp
            100                 105                 110

Pro Trp Gly Gln Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Arg Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
            290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
            355                 360                 365

Gln Val Ser Leu Thr Cys Leu Val Lys Gly Phe Tyr Pro Ser Asp Ile
            370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430
```

```
Ser Val Met His Glu Ala Leu His Asn His Tyr Thr Gln Lys Ser Leu
        435                 440                 445

Ser Leu Ser Pro Gly Lys
    450

<210> SEQ ID NO 26
<211> LENGTH: 214
<212> TYPE: PRT
<213> ORGANISM: Artificial Sequence
<220> FEATURE:
<223> OTHER INFORMATION: SAR114 Full-Length Light Chain

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Thr Ser Tyr
            20                  25                  30

Leu Asn Trp Tyr Gln Gln Lys Pro Gly Lys Ala Pro Lys Leu Leu Ile
        35                  40                  45

Tyr Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Glu Ser Tyr Ser Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 27
<211> LENGTH: 452
<212> TYPE: PRT
<213> ORGANISM: Artificial Sequence
<220> FEATURE:
<223> OTHER INFORMATION: MEDI4893 Full-Length Heavy Chain

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Asp Ser Val Lys
```

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
            85                  90                  95

Arg Asp Arg Tyr Ser Pro Thr Gly His Tyr Tyr Gly Met Asp Val Trp
        100                 105                 110

Gly Gln Gly Thr Thr Val Thr Val Ser Ser Ala Ser Thr Lys Gly Pro
    115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Tyr Ile Thr Arg Glu Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 28

<211> LENGTH: 212
<212> TYPE: PRT
<213> ORGANISM: Artificial Sequence
<220> FEATURE:
<223> OTHER INFORMATION: MEDI4893 and MEDI4893* Full-Length Light Chain

<400> SEQUENCE: 28

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Lys Gln Tyr Ala Asp Tyr Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu
    210

<210> SEQ ID NO 29
<211> LENGTH: 222
<212> TYPE: PRT
<213> ORGANISM: Artificial Sequence
<220> FEATURE:
<223> OTHER INFORMATION: N3 Fc starting from hinge

<400> SEQUENCE: 29

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser

```
                100                 105                 110
Lys Ala Lys Gly Gln Pro Arg Glu Pro Gln Val Tyr Thr Leu Pro Pro
            115                 120                 125

Ser Arg Glu Glu Met Thr Lys Asn Gln Val Ser Leu Thr Cys Leu Val
        130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Cys Ser
        195                 200                 205

Trp His Leu Cys Gln Lys Ser Leu Ser Leu Ser Pro Gly Lys
210                 215                 220

<210> SEQ ID NO 30
<211> LENGTH: 127
<212> TYPE: PRT
<213> ORGANISM: Artificial Sequence
<220> FEATURE:
<223> OTHER INFORMATION: SAR80 Variable Heavy Chain

<400> SEQUENCE: 30

Glu Val Gln Leu Val Glu Ser Gly Gly Asp Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Thr Trp Val Arg Gln Ala Pro Gly Lys Gly Leu Glu Trp Val
        35                  40                  45

Gly Arg Ile Arg Ser Lys Thr Ala Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Thr Ser Leu Lys Ile Glu Asp Thr Ala Leu Tyr
                85                  90                  95

Tyr Cys Met Thr Asp Gly Leu Gly Leu Leu Asn Phe Gly Asp Ser Asp
            100                 105                 110

Pro His His Tyr Trp Gly Gln Gly Thr Arg Val Thr Val Ser Ser
        115                 120                 125

<210> SEQ ID NO 31
<211> LENGTH: 106
<212> TYPE: PRT
<213> ORGANISM: Artificial Sequence
<220> FEATURE:
<223> OTHER INFORMATION: SAR80 Variable Light Chain

<400> SEQUENCE: 31

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Tyr Trp Tyr Gln Gln Lys Ser Gly Gln Ala Pro Val Leu Val Ile His
        35                  40                  45

Glu Asp Thr Lys Arg Pro Ser Gly Ile Pro Glu Arg Phe Ser Gly Ser
    50                  55                  60
```

Ser Ser Gly Thr Met Ala Thr Leu Thr Ile Ser Gly Ala Gln Val Glu
 65                  70                  75                  80

Asp Glu Ala Asp Tyr His Cys Tyr Ser Thr Asp Ser Ser Gly Val Val
                 85                  90                  95

Phe Gly Gly Gly Thr Lys Leu Thr Val Leu
            100                 105

<210> SEQ ID NO 32
<211> LENGTH: 122
<212> TYPE: PRT
<213> ORGANISM: Artificial Sequence
<220> FEATURE:
<223> OTHER INFORMATION: SAR113 Variable Heavy Chain
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid

<400> SEQUENCE: 32

Glu Val Gln Leu Val Gln Ser Gly Ala Glu Val Lys Lys Pro Gly Glu
1               5                   10                  15

Ser Leu Lys Ile Ser Cys Lys Ala Xaa Gly Tyr Xaa Phe Thr Ser Tyr
            20                  25                  30

Trp Ile Gly Trp Val Arg Gln Val Pro Gly Lys Gly Leu Glu Trp Met
        35                  40                  45

Gly Ile Ile Tyr Pro Gly Asp Ser Asp Thr Arg His Ser Pro Ser Phe
    50                  55                  60

Gln Gly Gln Val Thr Ile Ser Val Asp Lys Ser Ile Ser Thr Ala Tyr
65                  70                  75                  80

Leu Gln Trp Ser Ser Leu Lys Ala Ser Asp Ser Ala Met Tyr Tyr Cys
                85                  90                  95

Ala Arg His Gln Ser Gly Ser His Gly Phe Asp Ala Phe Glu Ile Trp
            100                 105                 110

Gly Gln Gly Thr Met Val Thr Val Ser Ser
        115                 120

<210> SEQ ID NO 33
<211> LENGTH: 113
<212> TYPE: PRT
<213> ORGANISM: Artificial Sequence
<220> FEATURE:
<223> OTHER INFORMATION: SAR113 Variable Light Chain

<400> SEQUENCE: 33

Asp Ile Val Leu Thr Gln Ser Pro Asp Ser Leu Ala Val Ser Leu Gly
1               5                   10                  15

Glu Arg Ala Thr Ile Asn Cys Lys Ser Ser Gln Gly Val Leu Ser Arg
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

```
Tyr Tyr Asn Asn Leu Arg Thr Phe Gly Gln Gly Thr Lys Val Glu Ile
                100                 105                 110

Arg

<210> SEQ ID NO 34
<211> LENGTH: 119
<212> TYPE: PRT
<213> ORGANISM: Artificial Sequence
<220> FEATURE:
<223> OTHER INFORMATION: SAR132 Variable Heavy Chain

<400> SEQUENCE: 34

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Asn Phe Thr Asn Tyr
            20                  25                  30

Trp Ile Ala Trp Val Arg Gln Met Pro Gly Lys Gly Leu Glu Trp Met
        35                  40                  45

Gly Ile Ile Tyr Ser Gly Asp Ser Asp Thr Arg Tyr Ser Pro Ser Phe
    50                  55                  60

Leu Gly Gln Val Ser Ile Ser Val Asp Lys Ser Phe Thr Thr Ala Tyr
65                  70                  75                  80

Leu Gln Trp Arg Ser Leu Lys Ala Ser Asp Thr Ala Met Tyr Tyr Cys
                85                  90                  95

Ala Arg Arg Pro Gly Gly Gln Lys Pro Tyr Asp Tyr Trp Gly Gln Gly
            100                 105                 110

Thr Leu Val Thr Val Ser Ser
        115

<210> SEQ ID NO 35
<211> LENGTH: 106
<212> TYPE: PRT
<213> ORGANISM: Artificial Sequence
<220> FEATURE:
<223> OTHER INFORMATION: SAR132 Variable Light Chain

<400> SEQUENCE: 35

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Arg Ile Ser Asn Trp
            20                  25                  30

Leu Ala Trp Tyr Gln Lys Pro Gly Lys Ala Pro Lys Leu Leu Ile
        35                  40                  45

Tyr Lys Ala Ser Thr Leu Glu Ser Glu Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Leu Ala Thr Tyr Tyr Cys His Gln Tyr Ile Ser Tyr Tyr Thr
                85                  90                  95

Phe Gly Gln Gly Thr Lys Leu Glu Ile Lys
            100                 105

<210> SEQ ID NO 36
<211> LENGTH: 136
<212> TYPE: PRT
<213> ORGANISM: Artificial Sequence
<220> FEATURE:
<223> OTHER INFORMATION: SAR352 Variable Heavy Chain

<400> SEQUENCE: 36
```

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Asn Ala
            20                  25                  30

Trp Met Ser Trp Val Arg Gln Ala Pro Gly Lys Gly Leu Glu Trp Val
        35                  40                  45

Gly Arg Ile Lys Ser Glu Thr Ala Gly Gly Thr Thr Asp Tyr Ala Ala
    50                  55                  60

Pro Val Lys Gly Arg Phe Ser Ile Ser Arg Asp Asp Ser Arg Asn Thr
65                  70                  75                  80

Leu Tyr Leu Glu Met Asn Ser Leu Lys Thr Asp Thr Ala Val Tyr
                85                  90                  95

Tyr Cys Thr Thr Asp Ser Tyr Thr Pro Leu Glu Glu Pro Cys Pro Asn
            100                 105                 110

Gly Val Cys Tyr Thr Tyr Tyr Tyr Gly Met Asp Val Trp Gly Gln
            115                 120                 125

Gly Thr Thr Val Thr Val Ser Ser
        130                 135
```

```
<210> SEQ ID NO 37
<211> LENGTH: 111
<212> TYPE: PRT
<213> ORGANISM: Artificial Sequence
<220> FEATURE:
<223> OTHER INFORMATION: SAR352 Variable Light Chain

<400> SEQUENCE: 37

Gln Ser Val Leu Thr Gln Pro Pro Ser Val Ser Ala Ala Pro Gly Glu
1               5                   10                  15

Lys Val Thr Ile Ser Cys Ser Gly Ser Ser Ser Asn Ile Gly Ala Asn
            20                  25                  30

Ser Val Ser Trp Tyr Gln Gln Phe Pro Gly Thr Ala Pro Lys Leu Leu
        35                  40                  45

Ile Tyr Asp Asn Asp Lys Arg Pro Ser Gly Val Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Val Gly Ile Leu
                85                  90                  95

Ser Ala Gly Trp Val Phe Gly Gly Gly Thr Lys Leu Thr Val Leu
            100                 105                 110
```

```
<210> SEQ ID NO 38
<211> LENGTH: 119
<212> TYPE: PRT
<213> ORGANISM: Artificial Sequence
<220> FEATURE:
<223> OTHER INFORMATION: SAR372 Variable Heavy Chain

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Asn Arg Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Ser Pro Ile Tyr Tyr Ala Asp Ser Val
```

-continued

```
                50                  55                  60
Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                 85                  90                  95

Ala Ser Arg Val Thr Leu Gly Leu Glu Phe Asp Phe Trp Gly Gln Gly
                100                 105                 110

Thr Leu Val Thr Val Ser Ser
        115

<210> SEQ ID NO 39
<211> LENGTH: 107
<212> TYPE: PRT
<213> ORGANISM: Artificial Sequence
<220> FEATURE:
<223> OTHER INFORMATION: SAR372 Variable Light Chain

<400> SEQUENCE: 39

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Asn
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Asp Arg Phe Ser Gly
 50                  55                  60

Ser Gly Ser Gly Thr Asp Phe Thr Leu Thr Ile Ser Ser Leu Lys Pro
 65                  70                  75                  80

Glu Asp Phe Ala Val Tyr Tyr Cys Gln Leu Arg Ser Asn Trp Ala Tyr
                 85                  90                  95

Thr Phe Gly Gln Gly Thr Lys Leu Glu Ile Lys
            100                 105

<210> SEQ ID NO 40
<211> LENGTH: 120
<212> TYPE: PRT
<213> ORGANISM: Artificial Sequence
<220> FEATURE:
<223> OTHER INFORMATION: SAR510 Variable Heavy Chain

<400> SEQUENCE: 40

Gln Val Thr Leu Arg Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ser
                 20                  25                  30

Gly Met Cys Val Gly Trp Ile Arg Gln Pro Pro Gly Lys Ala Leu Glu
             35                  40                  45

Trp Leu Ala Leu Ile Glu Trp Asp Asp Lys Tyr Tyr Asn Thr Ser
 50                  55                  60

Leu Lys Thr Arg Leu Ser Ile Ser Lys Asp Thr Ser Lys Asn Gln Val
 65                  70                  75                  80

Val Leu Thr Met Thr Asn Met Asp Pro Val Asp Thr Gly Thr Tyr Tyr
                 85                  90                  95

Cys Ala Arg His Ser Ser Ser Arg Gly Phe Asp Tyr Trp Gly Gln
            100                 105                 110

Gly Ala Leu Val Thr Val Ser Ser
        115                 120
```

<210> SEQ ID NO 41
<211> LENGTH: 107
<212> TYPE: PRT
<213> ORGANISM: Artificial Sequence
<220> FEATURE:
<223> OTHER INFORMATION: SAR510 Variable Light Chain

<400> SEQUENCE: 41

```
Ser Tyr Gly Leu Thr Gln Pro Pro Ser Val Ser Val Ser Pro Gly Gln
1               5                   10                  15

Thr Ala Arg Ile Thr Cys Ser Gly Asp Ala Leu Ala Lys Gln Tyr Val
            20                  25                  30

Tyr Trp Tyr Gln Gln Lys Pro Gly Gln Ala Pro Val Leu Val Ile Asp
        35                  40                  45

Lys Asp Arg Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Arg Thr Tyr
                85                  90                  95

Val Phe Gly Thr Gly Thr Lys Val Thr Val Leu
            100                 105
```

<210> SEQ ID NO 42
<211> LENGTH: 121
<212> TYPE: PRT
<213> ORGANISM: Artificial Sequence
<220> FEATURE:
<223> OTHER INFORMATION: SAR547 Variable Heavy Chain

<400> SEQUENCE: 42

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Thr Tyr
            20                  25                  30

Trp Ile Ala Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Thr Ala Thr Ala Tyr
65                  70                  75                  80

Leu Gln Trp Ser Ser Leu Asn Ala Ser Asp Ser Ala Met Tyr Tyr Cys
                85                  90                  95

Ala Arg Gln Gly Gly Ser His Gly Tyr Asp Ala Phe His Met Trp Gly
            100                 105                 110

Gln Gly Thr Met Val Thr Val Ser Ser
        115                 120
```

<210> SEQ ID NO 43
<211> LENGTH: 112
<212> TYPE: PRT
<213> ORGANISM: Artificial Sequence
<220> FEATURE:
<223> OTHER INFORMATION: SAR547 Variable Light Chain

<400> SEQUENCE: 43

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
```

```
            20                  25                  30

Asp Gly Asn Thr Tyr Leu Asn Trp Phe Gln Gln Arg Pro Gly Gln Ser
            35                  40                  45

Pro Arg Arg Leu Ile Tyr Lys Val Ser Asn Arg Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Leu Thr Trp Thr Phe Gly Gln Gly Thr Lys Val Glu Ile Lys
            100                 105                 110

<210> SEQ ID NO 44
<211> LENGTH: 112
<212> TYPE: PRT
<213> ORGANISM: Artificial Sequence
<220> FEATURE:
<223> OTHER INFORMATION: SAS1 Variable Heavy Chain

<400> SEQUENCE: 44

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Ser Thr Tyr
            20                  25                  30

Ala Leu Asn Trp Val Arg Gln Ala Pro Gly Lys Gly Leu Glu Trp Val
            35                  40                  45

Ala Gly Ile Asn Gly Thr Gly Tyr Asn Thr Tyr Tyr Ala Asp Ser Val
        50                  55                  60

Arg Gly Arg Phe Thr Ile Ser Arg Asp Asn Ser Lys Asn Thr Val Thr
65                  70                  75                  80

Leu Glu Met Asn Ser Leu Arg Val Glu Asp Thr Ala Thr Tyr Tyr Cys
                85                  90                  95

His Lys Val Pro Trp Trp Gly Gln Gly Thr Leu Val Ser Val Ser Ser
            100                 105                 110

<210> SEQ ID NO 45
<211> LENGTH: 113
<212> TYPE: PRT
<213> ORGANISM: Artificial Sequence
<220> FEATURE:
<223> OTHER INFORMATION: SAS1 Variable Light Chain

<400> SEQUENCE: 45

Asp Ile Val Leu Thr Gln Ser Pro Glu Ser Leu Ala Val Ser Leu Gly
1               5                   10                  15

Glu Arg Ala Thr Ile Ser Cys Lys Ser Ser Gln Ser Leu Phe Phe Lys
            20                  25                  30

Ser Asn Asn Lys Asn Tyr Leu Ala Trp Tyr Gln Gln Lys Pro Gly Gln
            35                  40                  45

Pro Pro Lys Val Ile Ile Tyr Trp Ala Ser Thr Arg Glu Ser Gly Val
        50                  55                  60

Pro Ala Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Phe Cys His Gln
                85                  90                  95

Tyr Tyr Ser Thr Gln Tyr Ser Phe Gly Gln Gly Thr Lys Leu Glu Ile
            100                 105                 110
```

Lys

```
<210> SEQ ID NO 46
<211> LENGTH: 128
<212> TYPE: PRT
<213> ORGANISM: Artificial Sequence
<220> FEATURE:
<223> OTHER INFORMATION: SAS19 Variable Heavy Chain

<400> SEQUENCE: 46
```

Gln Val Gln Leu Gln Glu Ser Gly Pro Arg Leu Val Lys Pro Ser Glu
1               5                   10                  15

Thr Leu Ser Leu Thr Cys Phe Val Ser Gly Gly Ser Ile Asn Asn Ser
            20                  25                  30

Tyr Trp Thr Trp Ile Arg Gln Pro Pro Gly Gln Gly Leu Glu Trp Ile
        35                  40                  45

Gly Phe Val Phe Ser Ser Gly Arg Thr Asn Tyr Ser Pro Ser Leu Lys
    50                  55                  60

Ser Arg Val Thr Ile Ser Val Asp Thr Ser Lys Asn Leu Phe Ser Leu
65                  70                  75                  80

Arg Leu Thr Ser Val Thr Ala Ala Asp Thr Ala Val Tyr Phe Cys Ala
                85                  90                  95

Arg Gln Val His Tyr Asp Phe Trp Ser Gly Tyr Ser Leu Thr Lys Thr
            100                 105                 110

Asn Trp Phe Asp Pro Trp Gly Gln Gly Thr Leu Val Thr Val Ser Ser
        115                 120                 125

```
<210> SEQ ID NO 47
<211> LENGTH: 107
<212> TYPE: PRT
<213> ORGANISM: Artificial Sequence
<220> FEATURE:
<223> OTHER INFORMATION: SAS19 Variable Light Chain

<400> SEQUENCE: 47
```

Asp Ile Gln Met Thr Gln Ser Pro Ser Ser Leu Ser Ala Ser Val Gly
1               5                   10                  15

Asp Thr Val Thr Ile Thr Cys Arg Thr Ser Gln Ser Ile Ser Asn Phe
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Val Asn Gly
    50                  55                  60

Ser Thr Ser Gly Thr Glu Phe Thr Leu Thr Leu Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Glu Ile Lys
            100                 105

```
<210> SEQ ID NO 48
<211> LENGTH: 128
<212> TYPE: PRT
<213> ORGANISM: Artificial Sequence
<220> FEATURE:
<223> OTHER INFORMATION: SAS203 Variable Heavy Chain

<400> SEQUENCE: 48
```

Gln Val Gln Leu Gln Glu Ser Gly Pro Gly Leu Val Lys Pro Ser Glu
1               5                   10                  15

-continued

```
Thr Leu Ser Leu Thr Cys Val Ser Gly Gly Ser Ile Asn Asn Ser
            20                  25                  30

Tyr Trp Thr Trp Ile Arg Gln Pro Gly Gln Gly Leu Glu Trp Ile
        35                  40                  45

Gly Phe Val Tyr Ser Ser Gly Arg Thr Tyr Tyr Ser Pro Ser Leu Lys
 50                  55                  60

Ser Arg Val Thr Ile Ser Val Asp Thr Ser Lys Asn Phe Phe Ser Leu
 65                  70                  75                  80

Arg Leu Asn Ser Val Thr Ala Ala Asp Thr Ala Val Tyr Phe Cys Ala
                 85                  90                  95

Arg Gln Val His Tyr Asp Leu Trp Ser Gly Tyr Ser Leu Thr Lys Thr
                100                 105                 110

Asn Trp Phe Asp Pro Trp Gly Gln Gly Thr Leu Val Thr Val Ser Ser
            115                 120                 125
```

<210> SEQ ID NO 49
<211> LENGTH: 107
<212> TYPE: PRT
<213> ORGANISM: Artificial Sequence
<220> FEATURE:
<223> OTHER INFORMATION: SAS203 Variable Light Chain

<400> SEQUENCE: 49

```
Asp Ile Gln Met Thr Gln Ser Pro Ser Ser Leu Ser Ala Ser Val Gly
 1               5                  10                  15

Asp Thr Val Thr Ile Thr Cys Arg Thr Ser Gln Ser Ile Ser Asn Phe
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Asn Gly
 50                  55                  60

Ser Thr Ser Gly Thr Asp Phe Thr Leu Thr Leu Ser Ser Leu Gln Pro
 65                  70                  75                  80

Glu Asp Phe Ala Thr Tyr Tyr Cys Gln Gln Ser Tyr Ser Thr Pro Trp
                 85                  90                  95

Thr Phe Gly Gln Gly Thr Lys Val Glu Ile Lys
                100                 105
```

<210> SEQ ID NO 50
<211> LENGTH: 454
<212> TYPE: PRT
<213> ORGANISM: Artificial Sequence
<220> FEATURE:
<223> OTHER INFORMATION: SAR114 N3Y Full-Length Heavy Chain

<400> SEQUENCE: 50

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Gln Asn Ser
            20                  25                  30

Tyr Trp Ser Trp Ile Arg Gln Pro Pro Gly Lys Gly Leu Glu Trp Ile
        35                  40                  45

Gly Tyr Leu Tyr Ser Ser Gly Arg Thr Asn Tyr Thr Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
```

```
            85                  90                  95
Arg Thr His Leu Gly Gly Phe His Tyr Gly Gly Phe Trp Phe Asp
            100                 105                 110

Pro Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Cys Ser Tyr His Leu Cys Gln Lys Ser Leu
        435                 440                 445

Ser Leu Ser Pro Gly Lys
    450

<210> SEQ ID NO 51
<211> LENGTH: 452
<212> TYPE: PRT
<213> ORGANISM: Artificial Sequence
<220> FEATURE:
<223> OTHER INFORMATION: MEDI4893* Full-Length Heavy Chain
```

<400> SEQUENCE: 51

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Asp Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Arg Tyr Ser Pro Thr Gly His Tyr Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415
```

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
        450

<210> SEQ ID NO 52
<211> LENGTH: 454
<212> TYPE: PRT
<213> ORGANISM: Artificial Sequence
<220> FEATURE:
<223> OTHER INFORMATION: SAR114 N3 Full-Length Heavy Chain

<400> SEQUENCE: 52

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Gln Asn Ser
            20                  25                  30

Tyr Trp Ser Trp Ile Arg Gln Pro Pro Gly Lys Gly Leu Glu Trp Ile
        35                  40                  45

Gly Tyr Leu Tyr Ser Ser Gly Arg Thr Asn Tyr Thr Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Thr His Leu Gly Gly Phe His Tyr Gly Gly Phe Trp Phe Asp
            100                 105                 110

Pro Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

```
                                    -continued

Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Cys Ser Trp His Leu Cys Gln Lys Ser Leu
            435                 440                 445

Ser Leu Ser Pro Gly Lys
    450
```